US010894823B2

(12) United States Patent
Sheng et al.

(10) Patent No.: US 10,894,823 B2
(45) Date of Patent: Jan. 19, 2021

(54) TRISPECIFIC INHIBITORS FOR CANCER TREATMENT

(71) Applicant: GENSUN BIOPHARMA INC., Newbury Park, CA (US)

(72) Inventors: Jackie Sheng, Thousand Oaks, CA (US); Bo Liu, Thousand Oaks, CA (US); Haiqun Jia, Thousand Oaks, CA (US)

(73) Assignee: GENSUN BIOPHARMA INC., Newbury Park (CA)

( * ) Notice: Subject to any disclaimer, the term of this patent is extended or adjusted under 35 U.S.C. 154(b) by 246 days.

(21) Appl. No.: 15/467,744

(22) Filed: Mar. 23, 2017

(65) Prior Publication Data

US 2017/0275353 A1 Sep. 28, 2017

Related U.S. Application Data

(60) Provisional application No. 62/312,965, filed on Mar. 24, 2016.

(51) Int. Cl.
| | | |
|---|---|---|
| *C07K 16/22* | (2006.01) | |
| *C07K 16/46* | (2006.01) | |
| *C07K 16/28* | (2006.01) | |
| *A61K 38/18* | (2006.01) | |
| *A61P 35/00* | (2006.01) | |

(52) U.S. Cl.
CPC .......... *C07K 16/22* (2013.01); *A61K 38/1891* (2013.01); *A61P 35/00* (2018.01); *C07K 16/2818* (2013.01); *C07K 16/2863* (2013.01); *C07K 16/468* (2013.01); *C07K 2317/24* (2013.01); *C07K 2317/31* (2013.01); *C07K 2317/60* (2013.01); *C07K 2317/622* (2013.01); *C07K 2317/64* (2013.01); *C07K 2317/66* (2013.01); *C07K 2317/76* (2013.01); *C07K 2317/92* (2013.01); *C07K 2318/20* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,837,243 A | 11/1998 | Deo et al. | |
| 5,869,046 A | 2/1999 | Presta et al. | |
| 5,922,845 A | 7/1999 | Deo et al. | |
| 6,054,297 A | 4/2000 | Carter et al. | |
| 6,111,090 A | 8/2000 | Gorman et al. | |
| 6,121,022 A | 9/2000 | Presta et al. | |
| 6,528,959 B2 | 3/2003 | Kitano et al. | |
| 6,703,020 B1 | 3/2004 | Thorpe et al. | |
| 6,884,879 B1 | 4/2005 | Baca et al. | |
| 7,025,962 B1 | 4/2006 | Gorman et al. | |
| 7,060,269 B1 | 6/2006 | Baca et al. | |
| 7,169,901 B2 | 1/2007 | Baca et al. | |
| 7,227,004 B2 | 6/2007 | Kim | |
| 7,338,660 B2 | 3/2008 | Bedian et al. | |
| 7,365,166 B2 | 4/2008 | Baca et al. | |
| 7,618,632 B2 | 11/2009 | Collins et al. | |
| 7,691,977 B2 | 4/2010 | Fuh et al. | |
| 7,758,859 B2 | 7/2010 | Fuh et al. | |
| 7,811,785 B2 | 10/2010 | Fuh et al. | |
| 7,812,135 B2 | 10/2010 | Smith et al. | |
| 8,367,805 B2 | 2/2013 | Chamberlain et al. | |
| 8,388,967 B2 | 3/2013 | Smith et al. | |
| 8,389,692 B2 | 3/2013 | Takayama et al. | |
| 8,475,798 B2 | 7/2013 | Patti et al. | |
| 8,574,577 B2* | 11/2013 | Barbas, III ........... | C12N 9/0002 424/134.1 |
| 8,586,023 B2 | 11/2013 | Shiku et al. | |
| 8,591,886 B2 | 11/2013 | Ponath et al. | |
| 8,992,913 B2 | 3/2015 | Mader et al. | |
| 9,079,965 B2 | 7/2015 | Zhou et al. | |
| 9,200,079 B2 | 12/2015 | Chamberlain et al. | |
| 9,676,863 B2 | 6/2017 | Lo | |
| 9,764,038 B2 | 9/2017 | Dennler et al. | |
| 9,890,204 B2 | 2/2018 | Brinkmann et al. | |
| 9,987,500 B2* | 6/2018 | Papadopoulos .... | A61K 39/3955 |
| 9,994,632 B2 | 6/2018 | Kim et al. | |
| 10,112,997 B2 | 10/2018 | Gurney et al. | |

(Continued)

FOREIGN PATENT DOCUMENTS

| | | |
|---|---|---|
| EP | 0090505 | 2/1984 |
| EP | 1947183 | 7/2008 |

(Continued)

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Hinton, et al., "An Engineered Human IgG1 Antibody with Longer Serum Half-Life", Journal of Immunology, 2006, 176:346-356.
Hinton, et al., "Engineered Human IgG Antibodies with Longer Serum Half-lives in Primates", Journal of Biological Chemistry, 2004, 279(8): 6213-6216.
Shields, et al., "High Resolution Mapping of the Binding Site on Human IgG1 for FcyRI, FcyRII, FcyRIII, and FcRn and Design of IgG1 Variants with Improved Binding to the FcyR", Journal of Biological Chemistry, 2001, 276 (9):6591-6604.

(Continued)

*Primary Examiner* — Meera Natarajan
(74) *Attorney, Agent, or Firm* — Michael X. Ye; Morris, Manning & Martin, LLP

(57) ABSTRACT

A trispecific inhibitor for treating cancer includes a first targeting domain having a binding specificity conferred by a VEGF binding antagonist; a second targeting domain having a binding specificity conferred by an immune checkpoint regulator binding antagonist; and a third targeting domain having a binding specificity conferred by a Tie2 tyrosine kinase receptor binding antagonist. The targeting domains may contain one or more antibody variable regions, peptide inhibitors, dominant negative proteins, small molecule drugs or combinations thereof.

7 Claims, 23 Drawing Sheets

Specification includes a Sequence Listing.

(56) References Cited

U.S. PATENT DOCUMENTS

| | | |
|---|---|---|
| 10,189,902 B2 | 1/2019 | Maurer et al. |
| 2003/0206899 A1 | 11/2003 | Ferrara et al. |
| 2005/0186208 A1 | 8/2005 | Fyfe et al. |
| 2006/0099150 A1 | 5/2006 | Houston et al. |
| 2014/0308285 A1* | 10/2014 | Yan ............ C07K 16/468 424/136.1 |
| 2016/0355589 A1 | 12/2016 | Williams et al. |
| 2017/0044256 A1 | 2/2017 | Grogan et al. |
| 2017/0275353 A1 | 9/2017 | Sheng et al. |
| 2018/0185482 A1 | 7/2018 | Sheng et al. |

FOREIGN PATENT DOCUMENTS

| | | |
|---|---|---|
| EP | 1866339 | 5/2013 |
| WO | 9920758 | 4/1999 |
| WO | 9940196 | 8/1999 |
| WO | 200103720 | 1/2001 |
| WO | 2005007190 | 1/2005 |
| WO | 2005055808 | 6/2005 |
| WO | 2006083289 | 8/2006 |
| WO | 2007133822 | 11/2007 |
| WO | 2010003118 | 1/2010 |
| WO | 2011028683 | 3/2011 |
| WO | 2005115451 | 5/2011 |
| WO | 2011051726 | 5/2011 |
| WO | 2011090754 | 7/2011 |
| WO | 2013039954 | 3/2013 |
| WO | 2014062659 | 4/2014 |
| WO | 2016187594 | 11/2016 |
| WO | 2017218707 | 6/2017 |
| WO | 2017161976 | 9/2017 |
| WS | 20181283939 | 7/2018 |

OTHER PUBLICATIONS

Ahmadzadeh, M. et al., "Tumor antigen-specific CD8 T cells infiltrating the tumor express high levels of PD-1 and are functionally impaired", Blood, Aug. 20, 2009, 114(8):1537.

Dall'acqua, et al., "Increasing the Affinity of a Human IgG1 for the Neonatal Fc Receptor: Biological Consequences", The Journal of Immunology, 2002, 169:5171-5180.

Dall'acqua, et al., "Properties of Human IgG1s Engineered for Enhanced Binding to the Neonatal Fc Receptor (FcRn)", Journal of Biological Chemistry, 2006, 281:23514-23524.

Dranoff, G. et al., "Vaccination with irradiated tumor cells engineered to secrete murine granulocyte-macrophage colony-stimulating factor stimulates potent, specific, and long-lasting antitumor immunity", Proc. Natl. Acad. Sci. U.S.A., Apr. 15, 1993, 90(8):3539-3543.

Greenberg, P.D. et al., "Deficient Cellular Immunit—Finding and Fixing the Defects", Science Jul. 23, 1999, 23:285 (546-551).

Harlow, E. et al., "Antibodies, A Laboratory Manual", (1988), Cold Spring Harbor Publications, New York.

He, Y. et al., "Blocking Programmed Death-1 Ligand-PD-1 Interactions by Local Gene Therapy Results in Enhancement of Antitumor Effect of Secondary Lymphoid Tissue Chemokine", The Journal of Immunology, 2004, 173:4919-4928.

Hutloff, A et al., "ICOS is an inducible T-cell co-stimulator structurally and functionally related to CD28", Nature, Jan. 21, 1999, 397:263-266.

International Search Report and Written Opinion of the International Searching Authority dated May 10, 2018 in PCT Application No. PCT/US17/69072.

Karyampudi, L. et al., "Accumulation of memory precursor CD8 T cells in regressing tumors following combination therapy with vaccine and anti-PD-1 antibody", Jun. 2014, 74:2974-2985.

Kim, N.W., et al., "Specific Association of Human Telomerase Activity with Immortal Cells and Cancer", Dec. 1994, vol. 266, pp. 2011-2013.

Kugler, A. et al., "Regression of human metastatic renal cell carcinoma after vaccination with tumor cell-dendritic cell hybrids", Nature Medicine, Mar. 6, 2000, 3:332-336.

Kyi, C. et al., "Checkpoint blocking antibodies in cancer immunotherapy", FEBS Letters, 2014, 588:368-376.

Le Mercier, I. et al., "Beyond CTLA-4 and PD-1, the Generation Z of Negative Checkpoint Regulators", Front. Immunol., Aug. 2015, (6), Article 418.

Lo, B.K.C., "Antibody engineering: Methods and Protocols, Methods in molecular biology", (2004) vol. 248. Humana Press, Clifton, N.J.

Melero, I et al., "Monoclonal antibodies against the 4-1BB T-cell activation molecule eradicate established tumors", Nature Medicine, Jun. 1997, 3(6):682-685.

Mokyr, M.B. et al., "Relization of the Therapeutic Potential of CTLA-4 Blockage in Low-Dose Chemotherpahy-treated Tumor-bearing Mice", Cancer Research (1998), 58:5301-5304.

Nestle, F.O. et al., "Vaccination of melanoma patients with peptide- or tumor lysate-pulsed dendritic cells", Nature Medicine, Mar. 1998, 4(3):328-332.

Petkova, S.B. et al., "Enhanced half-life of genetically engineered human IgG1 antibodies in a humanized FcRn mouse model: potential application in humorally mediated autoimmune disease," Int. Immunol., Dec. 2006, 18 (12):1759-1769.

Ridge, J.P. et al., "A conditioned dendritic cell can be a temporal bridge between a CD4+ T-helper and a T-killer cell", Nature, Jun. 4, 1998, 393:474-478.

Rosenberg, S.A. et al., "A New Era for Cancer Immunotherapy Based on the Genes that Encode Cancer Antigens", Immunity, Mar. 1999, vol. 10, pp. 281-287.

Tansey, M.G et al., "The TNF superfamily in 2009: new pathways, new indications, and new drugs", Drug Discovery Today, Dec. 2009, 14(23-24):1082-1088.

Thompson, R.H. et al., "Tumor B7-H1 Is Associated with Poor Prognosis in Renal Cell Carcinoma Patients with Long-term Follow-up", (2006), 66(7):3381.

Weinberg, A.D. et al., "Engagement of the OX-40 receptor in vivo enhances antitumor immunity", Journal of Immunology, Feb. 15, 2000, 15:164(4):2160-2169.

Wranik, et al., "LUZ-Y, a Novel Platform for the Mammalian Cell Production of Full-length IgG-bispecific Antibodies", Journal of Biological Chemistry, 2012, 287(52):43331-43339.

Yeung, et al., "Engineering Human IgG1 Affinity to Human Neonatal Fc Receptor: Impact of Affinity Improvement of Pharmacokinetics in Primates", The Journal of Immunology, 2009, 182:7663.

Zalevsky, J. et al., "Enhanced antibody half-life improves in vivo activity", Nat. Biotechnol., Feb. 2010, 28 (2):157-159.

International Search Report and the Written Opinion of the International Searching Authority issued in International Application No. PCT/US19/39979, dated Nov. 12, 2019.

International Search Report and the Written Opinion of the International Searching Authority issued in International Application No. PCT/US19/39982, dated Dec. 3, 2019.

International Search Report and the Written Opinion of the International Searching Authority issued in International Application No. PCT/US19/39994, dated Nov. 21, 2019.

* cited by examiner

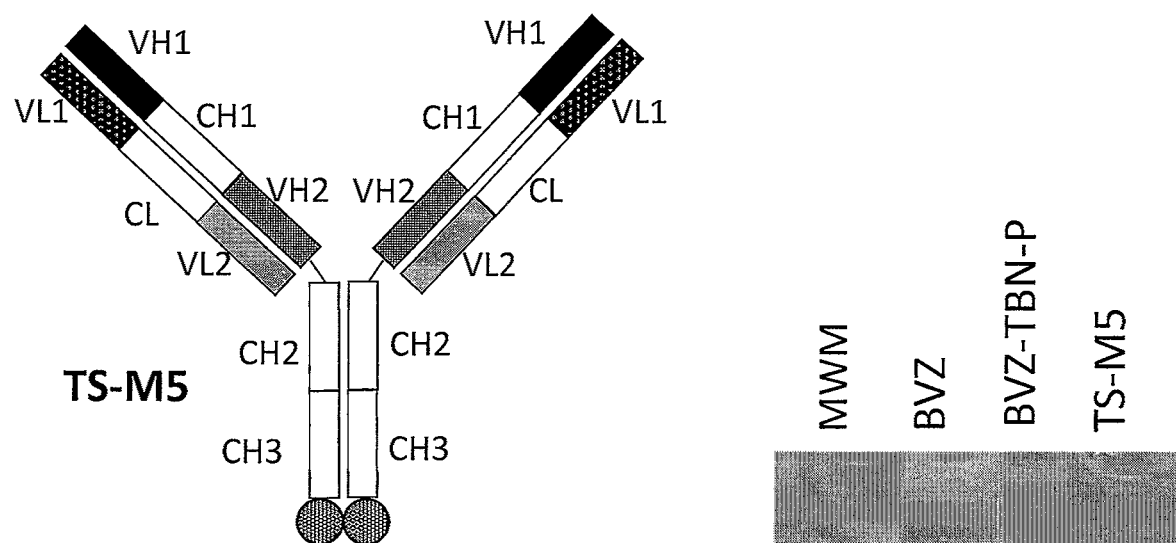
FIG. 8A
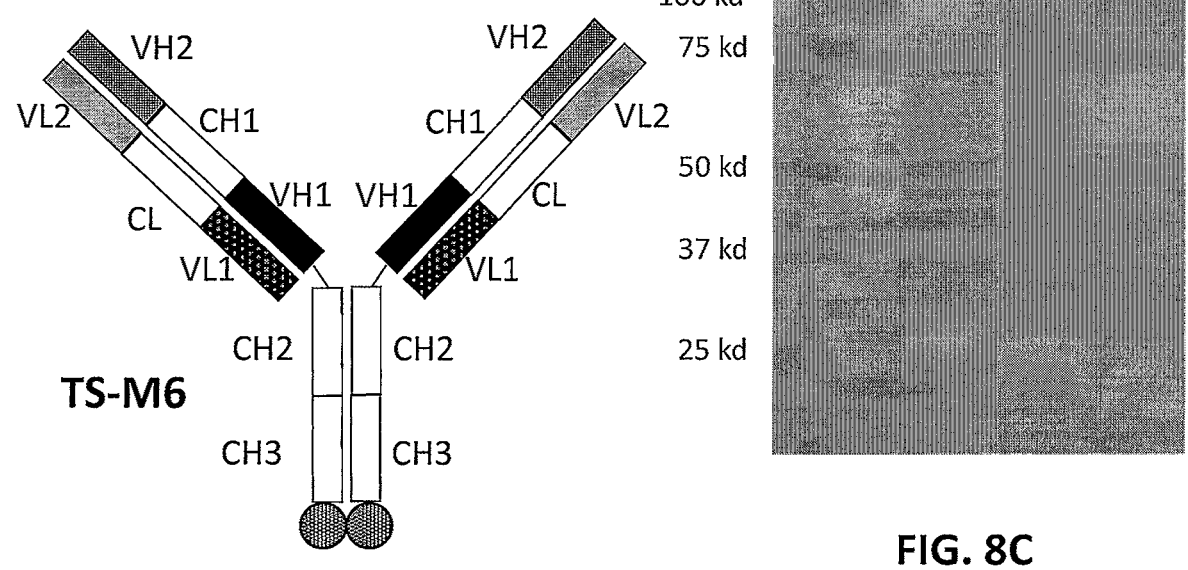
FIG. 8B
FIG. 8C

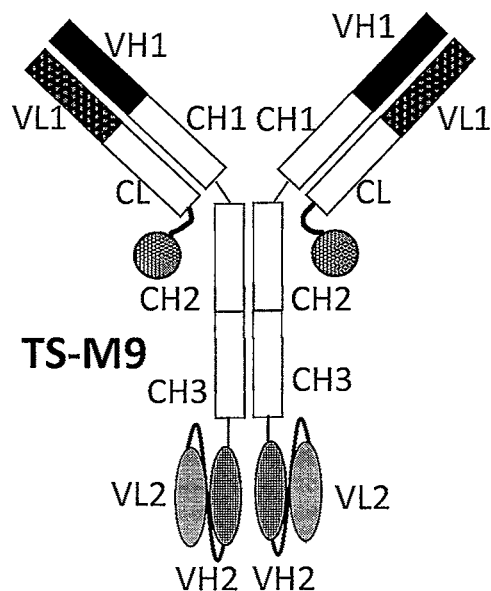
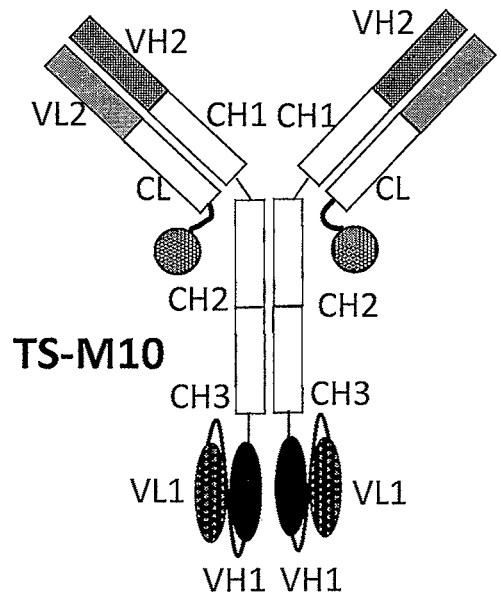
FIG. 10A
FIG. 10B
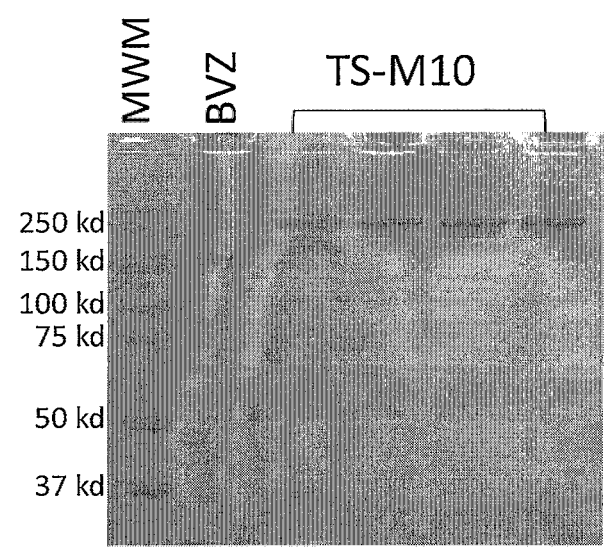
FIG. 10C

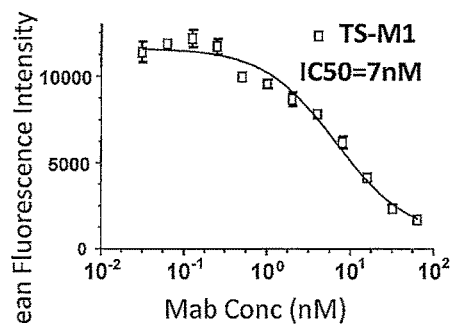
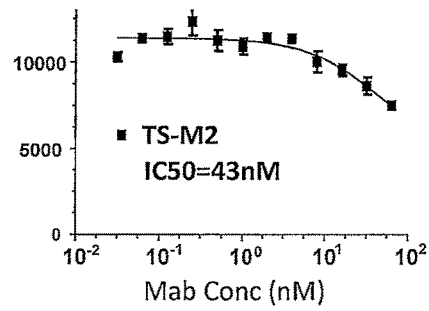
FIG. 12A  FIG. 12B
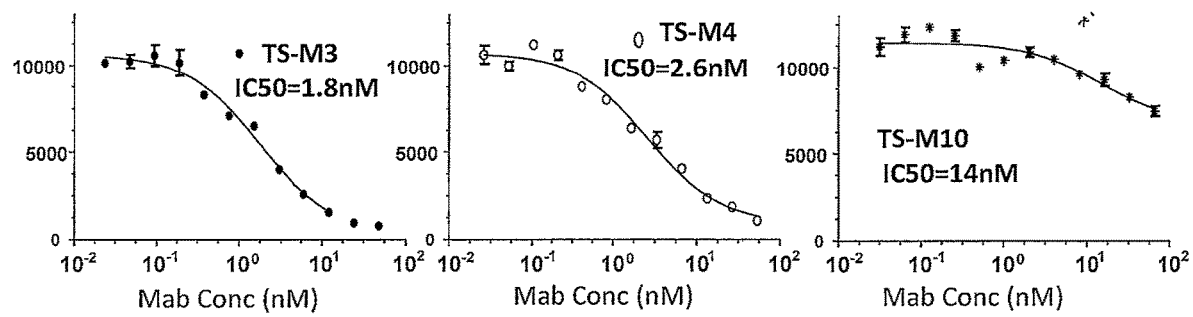
FIG. 12C  FIG. 12D  FIG. 12E
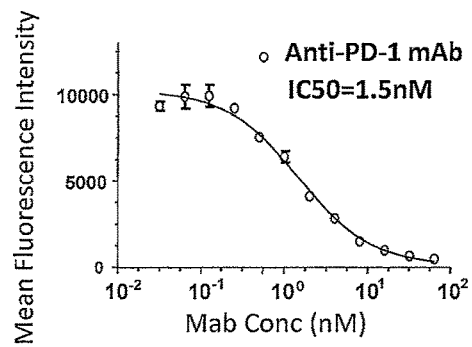
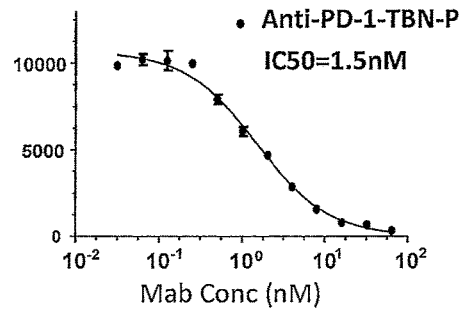
FIG. 12F  FIG. 12G

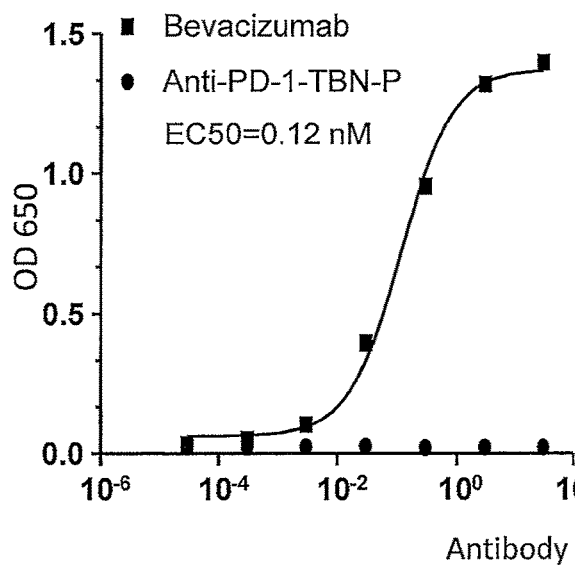
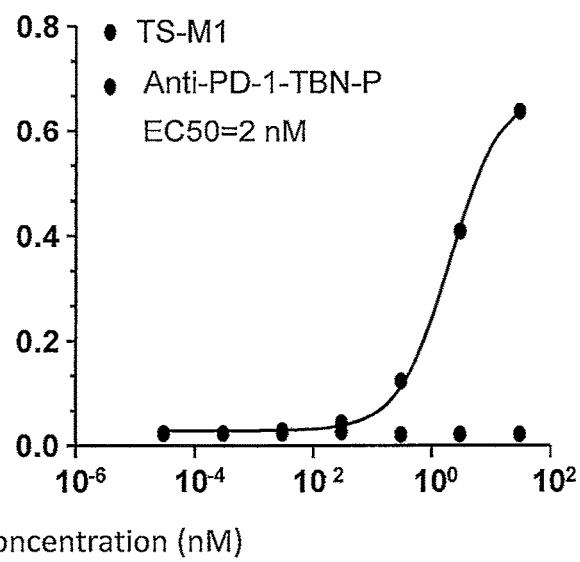
FIG. 18A   FIG. 18B
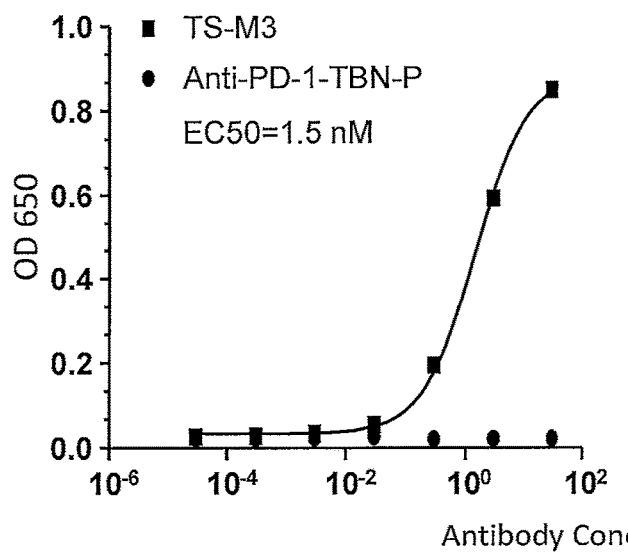
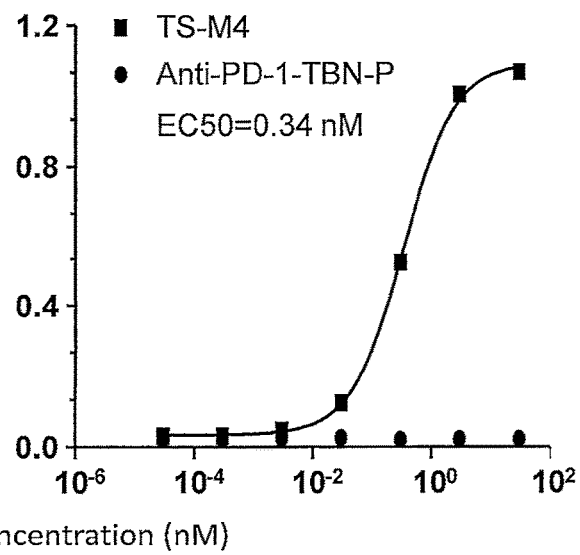
FIG. 18C   FIG. 18D

SEQUENCE LISTING

<160> NUMBER OF SEQ ID NOS: 49

<210> SEQ ID NO 1
<211> LENGTH: 54
<212> TYPE: PRT
<213> ORGANISM: Artificial Sequence
<220> FEATURE:
<223> OTHER INFORMATION: Synthetic

<400> SEQUENCE: 1

Ala Gln Gln Glu Glu Cys Glu Trp Asp Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Trp Asp Pro Trp Thr
        35                  40                  45

Cys Glu His Met Leu Glu
    50

<210> SEQ ID NO 2
<211> LENGTH: 286
<212> TYPE: PRT
<213> ORGANISM: Artificial Sequence
<220> FEATURE:
<223> OTHER INFORMATION: Synthetic

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ala Gln Gln Glu Glu Cys Glu Trp
225                 230                 235                 240

```
Asp Pro Trp Thr Cys Glu His Met Gly Ser Gly Ala Thr Gly Gly
                245                 250                 255

Ser Gly Ser Thr Ala Ser Ser Gly Ser Gly Ser Ala Thr His Gln Glu
        260                 265                 270

Glu Cys Glu Trp Asp Pro Trp Thr Cys Glu His Met Leu Glu
        275                 280                 285

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Glu Thr Phe Leu Ser Thr Asn Lys Leu Glu Asn Gln
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: ACETYLATION
<220> FEATURE:
<221> NAME/KEY: MOD_RES
<222> LOCATION: (9)..(9)
<223> OTHER INFORMATION: ACETYLATION
<220> FEATURE:
<221> NAME/KEY: misc_feature
<222> LOCATION: (11)..(12)
<223> OTHER INFORMATION: 0P: no PEG unit between peptide and the AZD
      linker

<400> SEQUENCE: 4

Gln Lys Tyr Gln Pro Leu Asp Glu Lys Asp Lys Thr Leu Tyr Asp Gln
1               5                   10                  15

Phe Met Leu Gln Gln Gly
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: DFB: 1,5-difluorobenzoyl
<220> FEATURE:
<221> NAME/KEY: misc_feature
<222> LOCATION: (11)..(12)
<223> OTHER INFORMATION: 0P: no PEG unit between peptide and the AZD
      linker

<400> SEQUENCE: 5

Thr Asn Phe Met Pro Met Asp Asp Leu Glu Lys Arg Leu Tyr Glu Gln
1               5                   10                  15

Phe Ile Leu Gln Gln Gly
            20

<210> SEQ ID NO 6
<211> LENGTH: 112
```

<212> TYPE: PRT
<213> ORGANISM: Artificial Sequence
<220> FEATURE:
<223> OTHER INFORMATION: Synthetic

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110
```

<210> SEQ ID NO 7
<211> LENGTH: 98
<212> TYPE: PRT
<213> ORGANISM: Artificial Sequence
<220> FEATURE:
<223> OTHER INFORMATION: Synthetic

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe
```

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

```
Gly Tyr Thr Phe Thr Asn Tyr Gly Met Asn
1               5                   10
```

<210> SEQ ID NO 9
<211> LENGTH: 17
<212> TYPE: PRT
<213> ORGANISM: Artificial Sequence
<220> FEATURE:
<223> OTHER INFORMATION: Synthetic

```
<400> SEQUENCE: 9

Trp Ile Asn Thr Tyr Thr Gly Glu Pro Thr Tyr Ala Ala Asp Phe Lys
1               5                   10                  15

Arg

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Tyr Pro His Tyr Tyr Gly Ser Ser His Trp Tyr Phe Asp Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Ser Ala Ser Gln Asp Ile Ser Asn Tyr Leu Asn
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Gln Gln Tyr Ser Thr Val Pro Trp Thr Phe
1               5                   10

<210> SEQ ID NO 13
<211> LENGTH: 440
<212> TYPE: PRT
<213> ORGANISM: Artificial Sequence
<220> FEATURE:
<223> OTHER INFORMATION: Synthetic

<400> SEQUENCE: 13

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125
```

-continued

```
Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```

```
<210> SEQ ID NO 14
<211> LENGTH: 113
<212> TYPE: PRT
<213> ORGANISM: Artificial Sequence
<220> FEATURE:
<223> OTHER INFORMATION: Synthetic

<400> SEQUENCE: 14
```

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45
```

Ala Val Ile Trp Tyr Asp Gly Ser Lys Arg Tyr Tyr Ala Asp Ser Val
            50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser

<210> SEQ ID NO 15
<211> LENGTH: 214
<212> TYPE: PRT
<213> ORGANISM: Artificial Sequence
<220> FEATURE:
<223> OTHER INFORMATION: Synthetic

<400> SEQUENCE: 15

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 17
<211> LENGTH: 448
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

```
Glu Val Lys Phe Asn Trp Tyr Val Asp Gly Val Glu His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 18
<211> LENGTH: 227
<212> TYPE: PRT
<213> ORGANISM: Artificial Sequence
<220> FEATURE:
<223> OTHER INFORMATION: Synthetic

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 19
<211> LENGTH: 107
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 20
<211> LENGTH: 628
<212> TYPE: PRT
<213> ORGANISM: Artificial Sequence
<220> FEATURE:
<223> OTHER INFORMATION: Synthetic: TS-M1, Heavy Chain

<400> SEQUENCE: 20

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Tyr Thr Phe Thr Asn Tyr Gly Met Asn Trp Val Arg Gln Ala Pro
```

```
            145                 150                 155                 160
        Gly Lys Gly Leu Glu Trp Val Gly Trp Ile Asn Thr Tyr Thr Gly Glu
                        165                 170                 175

Pro Thr Tyr Ala Ala Asp Phe Lys Arg Arg Phe Thr Phe Ser Leu Asp
                        180                 185                 190

Thr Ser Lys Ser Thr Ala Tyr Leu Gln Met Asn Ser Leu Arg Ala Glu
                        195                 200                 205

Asp Thr Ala Val Tyr Tyr Cys Ala Lys Tyr Pro His Tyr Tyr Gly Ser
                210                 215                 220

Ser His Trp Tyr Phe Asp Val Trp Gly Gln Gly Thr Leu Val Thr Val
        225                 230                 235                 240

Ser Ser Ala Ser Thr Lys Gly Pro Ser Val Phe Pro Leu Ala Pro Cys
                        245                 250                 255

Ser Arg Ser Thr Ser Glu Ser Thr Ala Ala Leu Gly Cys Leu Val Lys
                        260                 265                 270

Asp Tyr Phe Pro Glu Pro Val Thr Val Ser Trp Asn Ser Gly Ala Leu
                        275                 280                 285

Thr Ser Gly Val His Thr Phe Pro Ala Val Leu Gln Ser Ser Gly Leu
                        290                 295                 300

Tyr Ser Leu Ser Ser Val Val Thr Val Pro Ser Ser Ser Leu Gly Thr
        305                 310                 315                 320

Lys Thr Tyr Thr Cys Asn Val Asp His Lys Pro Ser Asn Thr Lys Val
                        325                 330                 335

Asp Lys Arg Val Glu Ser Lys Tyr Gly Pro Pro Cys Pro Cys Pro
                        340                 345                 350

Ala Pro Glu Phe Leu Gly Gly Pro Ser Val Phe Leu Phe Pro Pro Lys
                        355                 360                 365

Pro Lys Asp Thr Leu Met Ile Ser Arg Thr Pro Glu Val Thr Cys Val
                        370                 375                 380

Val Val Asp Val Ser Gln Glu Asp Pro Glu Val Gln Phe Asn Trp Tyr
        385                 390                 395                 400

Val Asp Gly Val Glu Val His Asn Ala Lys Thr Lys Pro Arg Glu Glu
                        405                 410                 415

Gln Phe Asn Ser Thr Tyr Arg Val Val Ser Val Leu Thr Val Leu His
                        420                 425                 430

Gln Asp Trp Leu Asn Gly Lys Glu Tyr Lys Cys Lys Val Ser Asn Lys
                        435                 440                 445

Gly Leu Pro Ser Ser Ile Glu Lys Thr Ile Ser Lys Ala Lys Gly Gln
                        450                 455                 460

Pro Arg Glu Pro Gln Val Tyr Thr Leu Pro Pro Ser Gln Glu Glu Met
        465                 470                 475                 480

Thr Lys Asn Gln Val Ser Leu Thr Cys Leu Val Lys Gly Phe Tyr Pro
                        485                 490                 495

Ser Asp Ile Ala Val Glu Trp Glu Ser Asn Gly Gln Pro Glu Asn Asn
                        500                 505                 510

Tyr Lys Thr Thr Pro Pro Val Leu Asp Ser Asp Gly Ser Phe Phe Leu
                        515                 520                 525

Tyr Ser Arg Leu Thr Val Asp Lys Ser Arg Trp Gln Glu Gly Asn Val
                        530                 535                 540

Phe Ser Cys Ser Val Met His Glu Ala Leu His Asn His Tyr Thr Gln
        545                 550                 555                 560

Lys Ser Leu Ser Leu Ser Leu Gly Lys Gly Gly Gly Gly Gly Ala Gln
                        565                 570                 575
```

```
Gln Glu Glu Cys Glu Trp Asp Pro Trp Thr Cys His Met Gly Ser
            580                 585                 590

Gly Ser Ala Thr Gly Gly Ser Gly Ser Thr Ala Ser Ser Gly Ser Gly
        595                 600                 605

Ser Ala Thr His Gln Glu Glu Cys Glu Trp Asp Pro Trp Thr Cys Glu
610                 615                 620

His Met Leu Glu
625

<210> SEQ ID NO 21
<211> LENGTH: 327
<212> TYPE: PRT
<213> ORGANISM: Artificial Sequence
<220> FEATURE:
<223> OTHER INFORMATION: Synthetic: TS-M1, Light Chain

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Asp Ile Gln Met Thr Gln Ser Pro Ser Ser Leu Ser Ala Ser Val
        115                 120                 125

Gly Asp Arg Val Thr Ile Thr Cys Ser Ala Ser Gln Asp Ile Ser Asn
130                 135                 140

Tyr Leu Asn Trp Tyr Gln Gln Lys Pro Gly Lys Ala Pro Lys Val Leu
145                 150                 155                 160

Ile Tyr Phe Thr Ser Ser Leu His Ser Gly Val Pro Ser Arg Phe Ser
                165                 170                 175

Gly Ser Gly Ser Gly Thr Asp Phe Thr Leu Thr Ile Ser Ser Leu Gln
            180                 185                 190

Pro Glu Asp Phe Ala Thr Tyr Tyr Cys Gln Gln Tyr Ser Thr Val Pro
        195                 200                 205

Trp Thr Phe Gly Gln Gly Thr Lys Val Glu Ile Lys Arg Thr Val Ala
210                 215                 220

Ala Pro Ser Val Phe Ile Phe Pro Pro Ser Asp Glu Gln Leu Lys Ser
225                 230                 235                 240

Gly Thr Ala Ser Val Val Cys Leu Leu Asn Asn Phe Tyr Pro Arg Glu
                245                 250                 255

Ala Lys Val Gln Trp Lys Val Asp Asn Ala Leu Gln Ser Gly Asn Ser
            260                 265                 270

Gln Glu Ser Val Thr Glu Gln Asp Ser Lys Asp Ser Thr Tyr Ser Leu
        275                 280                 285

Ser Ser Thr Leu Thr Leu Ser Lys Ala Asp Tyr Glu Lys His Lys Val
290                 295                 300
```

-continued

Tyr Ala Cys Glu Val Thr His Gln Gly Leu Ser Ser Pro Val Thr Lys
305                 310                 315                 320

Ser Phe Asn Arg Gly Glu Cys
                325

<210> SEQ ID NO 22
<211> LENGTH: 628
<212> TYPE: PRT
<213> ORGANISM: Artificial Sequence
<220> FEATURE:
<223> OTHER INFORMATION: Synthetic: TS-M2, Heavy Chain

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Gln Val Gln Leu Val Glu Ser Gly Gly Gly Val Val Gln Pro Gly
    130                 135                 140

Arg Ser Leu Arg Leu Asp Cys Lys Ala Ser Gly Ile Thr Phe Ser Asn
145                 150                 155                 160

Ser Gly Met His Trp Val Arg Gln Ala Pro Gly Lys Gly Leu Glu Trp
                165                 170                 175

Val Ala Val Ile Trp Tyr Asp Gly Ser Lys Arg Tyr Tyr Ala Asp Ser
            180                 185                 190

Val Lys Gly Arg Phe Thr Ile Ser Arg Asp Asn Ser Lys Asn Thr Leu
        195                 200                 205

Phe Leu Gln Met Asn Ser Leu Arg Ala Glu Asp Thr Ala Val Tyr Tyr
    210                 215                 220

Cys Ala Thr Asn Asp Asp Tyr Trp Gly Gln Gly Thr Leu Val Thr Val
225                 230                 235                 240

Ser Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                325                 330                 335

Asp Lys Arg Val Glu Ser Lys Tyr Gly Pro Pro Cys Pro Cys Pro
                340                 345                 350

Ala Pro Glu Phe Leu Gly Gly Pro Ser Val Phe Leu Phe Pro Pro Lys
            355                 360                 365

Pro Lys Asp Thr Leu Met Ile Ser Arg Thr Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                405                 410                 415

Gln Phe Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Gly Leu Pro Ser Ser Ile Glu Lys Thr Ile Ser Lys Ala Lys Gly Gln
450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Arg Leu Thr Val Asp Lys Ser Arg Trp Gln Glu Gly Asn Val
530                 535                 540

Phe Ser Cys Ser Val Met His Glu Ala Leu His Asn His Tyr Thr Gln
545                 550                 555                 560

Lys Ser Leu Ser Leu Ser Leu Gly Lys Gly Gly Gly Gly Ala Gln
                565                 570                 575

Gln Glu Glu Cys Glu Trp Asp Pro Trp Thr Cys Glu His Met Gly Ser
            580                 585                 590

Gly Ser Ala Thr Gly Gly Ser Gly Ser Thr Ala Ser Ser Gly Ser Gly
        595                 600                 605

Ser Ala Thr His Gln Glu Glu Cys Glu Trp Asp Pro Trp Thr Cys Glu
    610                 615                 620

His Met Leu Glu
625

<210> SEQ ID NO 23
<211> LENGTH: 327
<212> TYPE: PRT
<213> ORGANISM: Artificial Sequence
<220> FEATURE:
<223> OTHER INFORMATION: Synthetic: TS-M2, Light Chain

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Glu Ile Val Leu Thr Gln Ser Pro Ala Thr Leu Ser Leu Ser Pro
        115                 120                 125

Gly Glu Arg Ala Thr Leu Ser Cys Arg Ala Ser Gln Ser Val Ser Ser
130                 135                 140

Tyr Leu Ala Trp Tyr Gln Gln Lys Pro Gly Gln Ala Pro Arg Leu Leu
145                 150                 155                 160

Ile Tyr Asp Ala Ser Asn Arg Ala Thr Gly Ile Pro Ala Arg Phe Ser
                165                 170                 175

Gly Ser Gly Ser Gly Thr Asp Phe Thr Leu Thr Ile Ser Ser Leu Glu
            180                 185                 190

Pro Glu Asp Phe Ala Val Tyr Tyr Cys Gln Gln Ser Ser Asn Trp Pro
        195                 200                 205

Arg Thr Phe Gly Gln Gly Thr Lys Val Glu Ile Lys Arg Thr Val Ala
210                 215                 220

Ala Pro Ser Val Phe Ile Phe Pro Pro Ser Asp Glu Gln Leu Lys Ser
225                 230                 235                 240

Gly Thr Ala Ser Val Val Cys Leu Leu Asn Asn Phe Tyr Pro Arg Glu
                245                 250                 255

Ala Lys Val Gln Trp Lys Val Asp Asn Ala Leu Gln Ser Gly Asn Ser
            260                 265                 270

Gln Glu Ser Val Thr Glu Gln Asp Ser Lys Asp Ser Thr Tyr Ser Leu
        275                 280                 285

Ser Ser Thr Leu Thr Leu Ser Lys Ala Asp Tyr Glu Lys His Lys Val
290                 295                 300

Tyr Ala Cys Glu Val Thr His Gln Gly Leu Ser Ser Pro Val Thr Lys
305                 310                 315                 320

Ser Phe Asn Arg Gly Glu Cys
                325

<210> SEQ ID NO 24
<211> LENGTH: 622
<212> TYPE: PRT
<213> ORGANISM: Artificial Sequence
<220> FEATURE:
<223> OTHER INFORMATION: Synthetic: TS-M3, Heavy Chain

<400> SEQUENCE: 24

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95
```

```
Thr Phe Gly Gln Gly Thr Lys Val Glu Ile Lys Arg Thr Val Ala Ala
                100                 105                 110

Pro Glu Val Gln Leu Val Glu Ser Gly Gly Gly Leu Val Gln Pro Gly
                115                 120                 125

Gly Ser Leu Arg Leu Ser Cys Ala Ala Ser Gly Tyr Thr Phe Thr Asn
            130                 135                 140

Tyr Gly Met Asn Trp Val Arg Gln Ala Pro Gly Lys Gly Leu Glu Trp
145                 150                 155                 160

Val Gly Trp Ile Asn Thr Tyr Thr Gly Glu Pro Thr Tyr Ala Ala Asp
                    165                 170                 175

Phe Lys Arg Arg Phe Thr Phe Ser Leu Asp Thr Ser Lys Ser Thr Ala
                180                 185                 190

Tyr Leu Gln Met Asn Ser Leu Arg Ala Glu Asp Thr Ala Val Tyr Tyr
            195                 200                 205

Cys Ala Lys Tyr Pro His Tyr Tyr Gly Ser Ser His Trp Tyr Phe Asp
        210                 215                 220

Val Trp Gly Gln Gly Thr Leu Val Thr Val Ser Ser Ala Ser Thr Lys
225                 230                 235                 240

Gly Pro Ser Val Phe Pro Leu Ala Pro Cys Ser Arg Ser Thr Ser Glu
                    245                 250                 255

Ser Thr Ala Ala Leu Gly Cys Leu Val Lys Asp Tyr Phe Pro Glu Pro
                260                 265                 270

Val Thr Val Ser Trp Asn Ser Gly Ala Leu Thr Ser Gly Val His Thr
            275                 280                 285

Phe Pro Ala Val Leu Gln Ser Ser Gly Leu Tyr Ser Leu Ser Ser Val
        290                 295                 300

Val Thr Val Pro Ser Ser Ser Leu Gly Thr Lys Thr Tyr Thr Cys Asn
305                 310                 315                 320

Val Asp His Lys Pro Ser Asn Thr Lys Val Asp Lys Arg Val Glu Ser
                    325                 330                 335

Lys Tyr Gly Pro Pro Cys Pro Pro Cys Pro Ala Pro Glu Phe Leu Gly
                340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser Gln
        370                 375                 380

Glu Asp Pro Glu Val Gln Phe Asn Trp Tyr Val Asp Gly Val Glu Val
385                 390                 395                 400

His Asn Ala Lys Thr Lys Pro Arg Glu Glu Gln Phe Asn Ser Thr Tyr
                    405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Gly Leu Pro Ser Ser Ile
            435                 440                 445

Glu Lys Thr Ile Ser Lys Ala Lys Gly Gln Pro Arg Glu Pro Gln Val
        450                 455                 460

Tyr Thr Leu Pro Pro Ser Gln Glu Glu Met Thr Lys Asn Gln Val Ser
465                 470                 475                 480

Leu Thr Cys Leu Val Lys Gly Phe Tyr Pro Ser Asp Ile Ala Val Glu
                    485                 490                 495

Trp Glu Ser Asn Gly Gln Pro Glu Asn Asn Tyr Lys Thr Thr Pro Pro
                500                 505                 510
```

```
Val Leu Asp Ser Asp Gly Ser Phe Leu Tyr Ser Arg Leu Thr Val
        515                 520                 525

Asp Lys Ser Arg Trp Gln Glu Gly Asn Val Phe Ser Cys Ser Val Met
530                 535                 540

His Glu Ala Leu His Asn His Tyr Thr Gln Lys Ser Leu Ser Leu Ser
545                 550                 555                 560

Leu Gly Lys Gly Gly Gly Gly Ala Gln Gln Glu Cys Glu Trp
            565                 570                 575

Asp Pro Trp Thr Cys Glu His Met Gly Ser Gly Ser Ala Thr Gly Gly
                580                 585                 590

Ser Gly Ser Thr Ala Ser Ser Gly Ser Gly Ser Ala Thr His Gln Glu
        595                 600                 605

Glu Cys Glu Trp Asp Pro Trp Thr Cys Glu His Met Leu Glu
        610                 615                 620

<210> SEQ ID NO 25
<211> LENGTH: 333
<212> TYPE: PRT
<213> ORGANISM: Artificial Sequence
<220> FEATURE:
<223> OTHER INFORMATION: Synthetic: TS-M3, Light Chain

<400> SEQUENCE: 25

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Asp Ile Gln Met Thr Gln Ser Pro Ser
        115                 120                 125

Ser Leu Ser Ala Ser Val Gly Asp Arg Val Thr Ile Thr Cys Ser Ala
    130                 135                 140

Ser Gln Asp Ile Ser Asn Tyr Leu Asn Trp Tyr Gln Gln Lys Pro Gly
145                 150                 155                 160

Lys Ala Pro Lys Val Leu Ile Tyr Phe Thr Ser Ser Leu His Ser Gly
                165                 170                 175

Val Pro Ser Arg Phe Ser Gly Ser Gly Ser Gly Thr Asp Phe Thr Leu
            180                 185                 190

Thr Ile Ser Ser Leu Gln Pro Glu Asp Phe Ala Thr Tyr Tyr Cys Gln
        195                 200                 205

Gln Tyr Ser Thr Val Pro Trp Thr Phe Gly Gly Gly Thr Lys Val Glu
    210                 215                 220

Ile Lys Arg Thr Val Ala Ala Pro Ser Val Phe Ile Phe Pro Pro Ser
225                 230                 235                 240

Asp Glu Gln Leu Lys Ser Gly Thr Ala Ser Val Val Cys Leu Leu Asn
                245                 250                 255
```

```
Asn Phe Tyr Pro Arg Glu Ala Lys Val Gln Trp Lys Val Asp Asn Ala
                260                 265                 270

Leu Gln Ser Gly Asn Ser Gln Glu Ser Val Thr Glu Gln Asp Ser Lys
            275                 280                 285

Asp Ser Thr Tyr Ser Leu Ser Ser Thr Leu Thr Leu Ser Lys Ala Asp
        290                 295                 300

Tyr Glu Lys His Lys Val Tyr Ala Cys Glu Val Thr His Gln Gly Leu
305                 310                 315                 320

Ser Ser Pro Val Thr Lys Ser Phe Asn Arg Gly Glu Cys
                325                 330

<210> SEQ ID NO 26
<211> LENGTH: 612
<212> TYPE: PRT
<213> ORGANISM: Artificial Sequence
<220> FEATURE:
<223> OTHER INFORMATION: Synthetic: TS-M4, Heavy Chain

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Gln Val Gln Leu Val Glu Ser Gly Gly Val Val Gln Pro Gly
        115                 120                 125

Arg Ser Leu Arg Leu Asp Cys Lys Ala Ser Gly Ile Thr Phe Ser Asn
    130                 135                 140

Ser Gly Met His Trp Val Arg Gln Ala Pro Gly Lys Gly Leu Glu Trp
145                 150                 155                 160

Val Ala Val Ile Trp Tyr Asp Gly Ser Lys Arg Tyr Tyr Ala Asp Ser
                165                 170                 175

Val Lys Gly Arg Phe Thr Ile Ser Arg Asp Asn Ser Lys Asn Thr Leu
            180                 185                 190

Phe Leu Gln Met Asn Ser Leu Arg Ala Glu Asp Thr Ala Val Tyr Tyr
        195                 200                 205

Cys Ala Thr Asn Asp Asp Tyr Trp Gly Gln Gly Thr Leu Val Thr Val
    210                 215                 220

Ser Ser Ala Ser Thr Lys Gly Pro Ser Val Phe Pro Leu Ala Pro Cys
225                 230                 235                 240

Ser Arg Ser Thr Ser Glu Ser Thr Ala Ala Leu Gly Cys Leu Val Lys
                245                 250                 255

Asp Tyr Phe Pro Glu Pro Val Thr Val Ser Trp Asn Ser Gly Ala Leu
            260                 265                 270

Thr Ser Gly Val His Thr Phe Pro Ala Val Leu Gln Ser Ser Gly Leu
        275                 280                 285
```

Tyr Ser Leu Ser Ser Val Val Thr Val Pro Ser Ser Ser Leu Gly Thr
            290                 295                 300

Lys Thr Tyr Thr Cys Asn Val Asp His Lys Pro Ser Asn Thr Lys Val
305                 310                 315                 320

Asp Lys Arg Val Glu Ser Lys Tyr Gly Pro Pro Cys Pro Pro Cys Pro
                325                 330                 335

Ala Pro Glu Phe Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser Gln Glu Asp Pro Glu Val Gln Phe Asn Trp Tyr
370                 375                 380

Val Asp Gly Val Glu Val His Asn Ala Lys Thr Lys Pro Arg Glu Glu
385                 390                 395                 400

Gln Phe Asn Ser Thr Tyr Arg Val Val Ser Val Leu Thr Val Leu His
                405                 410                 415

Gln Asp Trp Leu Asn Gly Lys Glu Tyr Lys Cys Lys Val Ser Asn Lys
            420                 425                 430

Gly Leu Pro Ser Ser Ile Glu Lys Thr Ile Ser Lys Ala Lys Gly Gln
        435                 440                 445

Pro Arg Glu Pro Gln Val Tyr Thr Leu Pro Pro Ser Gln Glu Glu Met
450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Arg Leu Thr Val Asp Lys Ser Arg Trp Gln Glu Gly Asn Val
        515                 520                 525

Phe Ser Cys Ser Val Met His Glu Ala Leu His Asn His Tyr Thr Gln
530                 535                 540

Lys Ser Leu Ser Leu Ser Leu Gly Lys Gly Gly Gly Gly Ala Gln
545                 550                 555                 560

Gln Glu Glu Cys Glu Trp Asp Pro Trp Thr Cys Glu His Met Gly Ser
                565                 570                 575

Gly Ser Ala Thr Gly Gly Ser Gly Ser Thr Ala Ser Ser Gly Ser Gly
            580                 585                 590

Ser Ala Thr His Gln Glu Glu Cys Glu Trp Asp Pro Trp Thr Cys Glu
        595                 600                 605

His Met Leu Glu
    610

<210> SEQ ID NO 27
<211> LENGTH: 343
<212> TYPE: PRT
<213> ORGANISM: Artificial Sequence
<220> FEATURE:
<223> OTHER INFORMATION: Synthetic: TS-M4, Light Chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Glu Ile Val Leu Thr Gln Ser Pro Ala Thr Leu Ser Leu Ser Pro
130                 135                 140

Gly Glu Arg Ala Thr Leu Ser Cys Arg Ala Ser Gln Ser Val Ser Ser
145                 150                 155                 160

Tyr Leu Ala Trp Tyr Gln Gln Lys Pro Gly Gln Ala Pro Arg Leu Leu
                165                 170                 175

Ile Tyr Asp Ala Ser Asn Arg Ala Thr Gly Ile Pro Ala Arg Phe Ser
            180                 185                 190

Gly Ser Gly Ser Gly Thr Asp Phe Thr Leu Thr Ile Ser Ser Leu Glu
        195                 200                 205

Pro Glu Asp Phe Ala Val Tyr Tyr Cys Gln Gln Ser Ser Asn Trp Pro
210                 215                 220

Arg Thr Phe Gly Gln Gly Thr Lys Val Glu Ile Lys Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
290                 295                 300

Ser Ser Thr Leu Thr Leu Ser Lys Ala Asp Tyr Glu Lys His Lys Val
305                 310                 315                 320

Tyr Ala Cys Glu Val Thr His Gln Gly Leu Ser Ser Pro Val Thr Lys
                325                 330                 335

Ser Phe Asn Arg Gly Glu Cys
            340

<210> SEQ ID NO 28
<211> LENGTH: 642
<212> TYPE: PRT
<213> ORGANISM: Artificial Sequence
<220> FEATURE:
<223> OTHER INFORMATION: Synthetic: TS-M5, Heavy Chain

<400> SEQUENCE: 28

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

-continued

```
Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Gly Gly Gly Gly Ser Gly Gly Gly Ser Glu Val Gln
210                 215                 220

Leu Val Glu Ser Gly Gly Gly Leu Val Gln Pro Gly Gly Ser Leu Arg
225                 230                 235                 240

Leu Ser Cys Ala Ala Ser Gly Tyr Thr Phe Thr Asn Tyr Gly Met Asn
                245                 250                 255

Trp Val Arg Gln Ala Pro Gly Lys Gly Leu Glu Trp Val Gly Trp Ile
            260                 265                 270

Asn Thr Tyr Thr Gly Glu Pro Thr Tyr Ala Ala Asp Phe Lys Arg Arg
            275                 280                 285

Phe Thr Phe Ser Leu Asp Thr Ser Lys Ser Thr Ala Tyr Leu Gln Met
            290                 295                 300

Asn Ser Leu Arg Ala Glu Asp Thr Ala Val Tyr Tyr Cys Ala Lys Tyr
305                 310                 315                 320

Pro His Tyr Tyr Gly Ser Ser His Trp Tyr Phe Asp Val Trp Gly Gln
                325                 330                 335

Gly Thr Leu Val Thr Val Ser Ser Gly Gly Gly Ser Gly Gly Gly
            340                 345                 350

Gly Ser Glu Ser Lys Tyr Gly Pro Pro Cys Pro Pro Cys Pro Ala Pro
        355                 360                 365

Glu Phe Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
                405                 410                 415

Gly Val Glu Val His Asn Ala Lys Thr Lys Pro Arg Glu Glu Gln Phe
            420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Gly Leu
450                 455                 460

Pro Ser Ser Ile Glu Lys Thr Ile Ser Lys Ala Lys Gly Gln Pro Arg
```

```
                465                 470                 475                 480
Glu Pro Gln Val Tyr Thr Leu Pro Pro Ser Gln Glu Glu Met Thr Lys
                    485                 490                 495

Asn Gln Val Ser Leu Thr Cys Leu Val Lys Gly Phe Tyr Pro Ser Asp
                500                 505                 510

Ile Ala Val Glu Trp Glu Ser Asn Gly Gln Pro Glu Asn Asn Tyr Lys
                515                 520                 525

Thr Thr Pro Pro Val Leu Asp Ser Asp Gly Ser Phe Phe Leu Tyr Ser
            530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly Lys Gly Gly Gly Gly Ala Gln Gln Glu
                580                 585                 590

Glu Cys Glu Trp Asp Pro Trp Thr Cys Glu His Met Gly Ser Gly Ser
            595                 600                 605

Ala Thr Gly Gly Ser Gly Ser Thr Ala Ser Ser Gly Ser Gly Ser Ala
        610                 615                 620

Thr His Gln Glu Glu Cys Glu Trp Asp Pro Trp Thr Cys Glu His Met
625                 630                 635                 640

Leu Glu

<210> SEQ ID NO 29
<211> LENGTH: 331
<212> TYPE: PRT
<213> ORGANISM: Artificial Sequence
<220> FEATURE:
<223> OTHER INFORMATION: Synthetic: TS-M5, Light Chain

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Ser Ala Ser Gln Asp Ile Ser Asn Tyr
                245                 250                 255

Leu Asn Trp Tyr Gln Gln Lys Pro Gly Lys Ala Pro Lys Val Leu Ile
            260                 265                 270

Tyr Phe Thr Ser Ser Leu His Ser Gly Val Pro Ser Arg Phe Ser Gly
        275                 280                 285

Ser Gly Ser Gly Thr Asp Phe Thr Leu Thr Ile Ser Ser Leu Gln Pro
    290                 295                 300

Glu Asp Phe Ala Thr Tyr Tyr Cys Gln Gln Tyr Ser Thr Val Pro Trp
305                 310                 315                 320

Thr Phe Gly Gln Gly Thr Lys Val Glu Ile Lys
                325                 330
```

<210> SEQ ID NO 30
<211> LENGTH: 642
<212> TYPE: PRT
<213> ORGANISM: Artificial Sequence
<220> FEATURE:
<223> OTHER INFORMATION: Synthetic: TS-M6, Heavy Chain

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Gly Gly Gly
    210                 215                 220
```

```
Gly Ser Gly Gly Gly Ser Gln Val Gln Leu Val Glu Ser Gly Gly
225                 230                 235                 240

Gly Val Val Gln Pro Gly Arg Ser Leu Arg Leu Asp Cys Lys Ala Ser
            245                 250                 255

Gly Ile Thr Phe Ser Asn Ser Gly Met His Trp Val Arg Gln Ala Pro
                260                 265                 270

Gly Lys Gly Leu Glu Trp Val Ala Val Ile Trp Tyr Asp Gly Ser Lys
            275                 280                 285

Arg Tyr Tyr Ala Asp Ser Val Lys Gly Arg Phe Thr Ile Ser Arg Asp
290                 295                 300

Asn Ser Lys Asn Thr Leu Phe Leu Gln Met Asn Ser Leu Arg Ala Glu
305                 310                 315                 320

Asp Thr Ala Val Tyr Tyr Cys Ala Thr Asn Asp Asp Tyr Trp Gly Gln
            325                 330                 335

Gly Thr Leu Val Thr Val Ser Ser Gly Gly Gly Ser Gly Gly Gly
            340                 345                 350

Gly Ser Glu Ser Lys Tyr Gly Pro Pro Cys Pro Pro Cys Pro Ala Pro
            355                 360                 365

Glu Phe Leu Gly Gly Pro Ser Val Phe Leu Phe Pro Pro Lys Pro Lys
370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
            405                 410                 415

Gly Val Glu Val His Asn Ala Lys Thr Lys Pro Arg Glu Glu Gln Phe
            420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Gly Leu
450                 455                 460

Pro Ser Ser Ile Glu Lys Thr Ile Ser Lys Ala Lys Gly Gln Pro Arg
465                 470                 475                 480

Glu Pro Gln Val Tyr Thr Leu Pro Pro Ser Gln Glu Glu Met Thr Lys
            485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
            565                 570                 575

Leu Ser Leu Ser Leu Gly Lys Gly Gly Gly Gly Ala Gln Gln Glu
            580                 585                 590

Glu Cys Glu Trp Asp Pro Trp Thr Cys Glu His Met Gly Ser Gly Ser
            595                 600                 605

Ala Thr Gly Gly Ser Gly Ser Thr Ala Ser Ser Gly Ser Gly Ser Ala
            610                 615                 620

Thr His Gln Glu Glu Cys Glu Trp Asp Pro Trp Thr Cys Glu His Met
625                 630                 635                 640
```

Leu Glu

<210> SEQ ID NO 31
<211> LENGTH: 331
<212> TYPE: PRT
<213> ORGANISM: Artificial Sequence
<220> FEATURE:
<223> OTHER INFORMATION: Synthetic: TS-M6, Light Chain

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Glu Ile Val Leu Thr Gln Ser Pro Ala Thr Leu Ser Leu Ser Pro Gly
225                 230                 235                 240

Glu Arg Ala Thr Leu Ser Cys Arg Ala Ser Gln Ser Val Ser Ser Tyr
                245                 250                 255

Leu Ala Trp Tyr Gln Gln Lys Pro Gly Gln Ala Pro Arg Leu Leu Ile
            260                 265                 270

Tyr Asp Ala Ser Asn Arg Ala Thr Gly Ile Pro Ala Arg Phe Ser Gly
        275                 280                 285

Ser Gly Ser Gly Thr Asp Phe Thr Leu Thr Ile Ser Ser Leu Glu Pro
    290                 295                 300

Glu Asp Phe Ala Val Tyr Tyr Cys Gln Gln Ser Ser Asn Trp Pro Arg
305                 310                 315                 320

Thr Phe Gly Gln Gly Thr Lys Val Glu Ile Lys
                325                 330

<210> SEQ ID NO 32
<211> LENGTH: 499
<212> TYPE: PRT

<213> ORGANISM: Artificial Sequence
<220> FEATURE:
<223> OTHER INFORMATION: Synthetic: TS-M7, Heavy Chain

<400> SEQUENCE: 32

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
```

```
385                 390                 395                 400
Ser Arg Leu Thr Val Asp Lys Ser Arg Trp Gln Glu Gly Asn Val Phe
                    405                 410                 415

Ser Cys Ser Val Met His Glu Ala Leu His Asn His Tyr Thr Gln Lys
                420                 425                 430

Ser Leu Ser Leu Ser Leu Gly Lys Gly Gly Gly Gly Ala Gln Gln
            435                 440                 445

Glu Glu Cys Glu Trp Asp Pro Trp Thr Cys His Met Gly Ser Gly
450                 455                 460

Ser Ala Thr Gly Gly Ser Gly Ser Thr Ala Ser Ser Gly Ser Gly Ser
465                 470                 475                 480

Ala Thr His Gln Glu Glu Cys Glu Trp Asp Pro Trp Thr Cys Glu His
                485                 490                 495

Met Leu Glu

<210> SEQ ID NO 33
<211> LENGTH: 469
<212> TYPE: PRT
<213> ORGANISM: Artificial Sequence
<220> FEATURE:
<223> OTHER INFORMATION: Synthetic: TS-M7, Light Chain

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Glu Val Gln Leu Val Glu Ser Gly Gly Gly Leu Val Gln Pro Gly Gly
225                 230                 235                 240

Ser Leu Arg Leu Ser Cys Ala Ala Ser Gly Tyr Thr Phe Thr Asn Tyr
                245                 250                 255
```

Gly Met Asn Trp Val Arg Gln Ala Pro Gly Lys Gly Leu Glu Trp Val
            260                 265                 270

Gly Trp Ile Asn Thr Tyr Thr Gly Glu Pro Thr Tyr Ala Ala Asp Phe
            275                 280                 285

Lys Arg Arg Phe Thr Phe Ser Leu Asp Thr Ser Lys Ser Thr Ala Tyr
290                 295                 300

Leu Gln Met Asn Ser Leu Arg Ala Glu Asp Thr Ala Val Tyr Tyr Cys
305                 310                 315                 320

Ala Lys Tyr Pro His Tyr Tyr Gly Ser Ser His Trp Tyr Phe Asp Val
                325                 330                 335

Trp Gly Gln Gly Thr Leu Val Thr Val Ser Ser Gly Gly Gly Gly Ser
            340                 345                 350

Gly Gly Gly Gly Ser Gly Gly Gly Ser Asp Ile Gln Met Thr Gln
            355                 360                 365

Ser Pro Ser Ser Leu Ser Ala Ser Val Gly Asp Arg Val Thr Ile Thr
370                 375                 380

Cys Ser Ala Ser Gln Asp Ile Ser Asn Tyr Leu Asn Trp Tyr Gln Gln
385                 390                 395                 400

Lys Pro Gly Lys Ala Pro Lys Val Leu Ile Tyr Phe Thr Ser Ser Leu
                405                 410                 415

His Ser Gly Val Pro Ser Arg Phe Ser Gly Ser Gly Ser Gly Thr Asp
            420                 425                 430

Phe Thr Leu Thr Ile Ser Ser Leu Gln Pro Glu Asp Phe Ala Thr Tyr
            435                 440                 445

Tyr Cys Gln Gln Tyr Ser Thr Val Pro Trp Thr Phe Gly Gln Gly Thr
450                 455                 460

Lys Val Glu Ile Lys
465

<210> SEQ ID NO 34
<211> LENGTH: 509
<212> TYPE: PRT
<213> ORGANISM: Artificial Sequence
<220> FEATURE:
<223> OTHER INFORMATION: Synthetic: TS-M8, Heavy Chain

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys Gly Gly Gly Gly Ala Gln Gln Glu Glu Cys Glu Trp Asp
450                 455                 460

Pro Trp Thr Cys Glu His Met Gly Ser Gly Ser Ala Thr Gly Gly Ser
465                 470                 475                 480

Gly Ser Thr Ala Ser Ser Gly Ser Gly Ser Ala Thr His Gln Glu Glu
            485                 490                 495

Cys Glu Trp Asp Pro Trp Thr Cys Glu His Met Leu Glu
            500                 505

<210> SEQ ID NO 35
<211> LENGTH: 459
<212> TYPE: PRT
<213> ORGANISM: Artificial Sequence
<220> FEATURE:
<223> OTHER INFORMATION: Synthetic: TS-M8, Light Chain

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
210                 215                 220

Gln Val Gln Leu Val Glu Ser Gly Gly Val Val Gln Pro Gly Arg
225                 230                 235                 240

Ser Leu Arg Leu Asp Cys Lys Ala Ser Gly Ile Thr Phe Ser Asn Ser
            245                 250                 255

Gly Met His Trp Val Arg Gln Ala Pro Gly Lys Gly Leu Glu Trp Val
        260                 265                 270

Ala Val Ile Trp Tyr Asp Gly Ser Lys Arg Tyr Tyr Ala Asp Ser Val
        275                 280                 285

Lys Gly Arg Phe Thr Ile Ser Arg Asp Asn Ser Lys Asn Thr Leu Phe
290                 295                 300

Leu Gln Met Asn Ser Leu Arg Ala Glu Asp Thr Ala Val Tyr Tyr Cys
305                 310                 315                 320

Ala Thr Asn Asp Asp Tyr Trp Gly Gln Gly Thr Leu Val Thr Val Ser
            325                 330                 335

Ser Gly Gly Gly Gly Ser Gly Gly Gly Gly Ser Gly Gly Gly Gly Ser
        340                 345                 350

Glu Ile Val Leu Thr Gln Ser Pro Ala Thr Leu Ser Leu Ser Pro Gly
            355                 360                 365

Glu Arg Ala Thr Leu Ser Cys Arg Ala Ser Gln Ser Val Ser Ser Tyr
        370                 375                 380

Leu Ala Trp Tyr Gln Gln Lys Pro Gly Gln Ala Pro Arg Leu Leu Ile
385                 390                 395                 400

Tyr Asp Ala Ser Asn Arg Ala Thr Gly Ile Pro Ala Arg Phe Ser Gly
                405                 410                 415
```

```
Ser Gly Ser Gly Thr Asp Phe Thr Leu Thr Ile Ser Ser Leu Glu Pro
            420                 425                 430

Glu Asp Phe Ala Val Tyr Tyr Cys Gln Gln Ser Ser Asn Trp Pro Arg
        435                 440                 445

Thr Phe Gly Gln Gly Thr Lys Val Glu Ile Lys
        450                 455

<210> SEQ ID NO 36
<211> LENGTH: 695
<212> TYPE: PRT
<213> ORGANISM: Artificial Sequence
<220> FEATURE:
<223> OTHER INFORMATION: Synthetic: TS-M9, Heavy Chain

<400> SEQUENCE: 36

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320
```

```
Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
        340                 345                 350

Lys Asn Gln Val Ser Leu Thr Cys Leu Val Lys Gly Phe Tyr Pro Ser
    355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys Gly Gly Gly Gly Ser Gly Gly Gly
        435                 440                 445

Gly Ser Glu Val Gln Leu Val Glu Ser Gly Gly Gly Leu Val Gln Pro
450                 455                 460

Gly Gly Ser Leu Arg Leu Ser Cys Ala Ala Ser Gly Tyr Thr Phe Thr
465                 470                 475                 480

Asn Tyr Gly Met Asn Trp Val Arg Gln Ala Pro Gly Lys Gly Leu Glu
                485                 490                 495

Trp Val Gly Trp Ile Asn Thr Tyr Thr Gly Glu Pro Thr Tyr Ala Ala
            500                 505                 510

Asp Phe Lys Arg Arg Phe Thr Phe Ser Leu Asp Thr Ser Lys Ser Thr
        515                 520                 525

Ala Tyr Leu Gln Met Asn Ser Leu Arg Ala Glu Asp Thr Ala Val Tyr
530                 535                 540

Tyr Cys Ala Lys Tyr Pro His Tyr Tyr Gly Ser Ser His Trp Tyr Phe
545                 550                 555                 560

Asp Val Trp Gly Gln Gly Thr Leu Val Thr Val Ser Ser Gly Gly Gly
                565                 570                 575

Gly Ser Gly Gly Gly Gly Ser Gly Gly Gly Gly Ser Asp Ile Gln Met
            580                 585                 590

Thr Gln Ser Pro Ser Ser Leu Ser Ala Ser Val Gly Asp Arg Val Thr
        595                 600                 605

Ile Thr Cys Ser Ala Ser Gln Asp Ile Ser Asn Tyr Leu Asn Trp Tyr
610                 615                 620

Gln Gln Lys Pro Gly Lys Ala Pro Lys Val Leu Ile Tyr Phe Thr Ser
625                 630                 635                 640

Ser Leu His Ser Gly Val Pro Ser Arg Phe Ser Gly Ser Gly Ser Gly
                645                 650                 655

Thr Asp Phe Thr Leu Thr Ile Ser Ser Leu Gln Pro Glu Asp Phe Ala
            660                 665                 670

Thr Tyr Tyr Cys Gln Gln Tyr Ser Thr Val Pro Trp Thr Phe Gly Gln
        675                 680                 685

Gly Thr Lys Val Glu Ile Lys
690                 695

<210> SEQ ID NO 37
<211> LENGTH: 273
<212> TYPE: PRT
<213> ORGANISM: Artificial Sequence
<220> FEATURE:
<223> OTHER INFORMATION: Synthetic: TS-M9, Light Chain
```

-continued

<400> SEQUENCE: 37

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ala Gln Gln Glu Glu
210                 215                 220

Cys Glu Trp Asp Pro Trp Thr Cys Glu His Met Gly Ser Gly Ser Ala
225                 230                 235                 240

Thr Gly Gly Ser Gly Ser Thr Ala Ser Ser Gly Ser Gly Ser Ala Thr
                245                 250                 255

His Gln Glu Glu Cys Glu Trp Asp Pro Trp Thr Cys Glu His Met Leu
            260                 265                 270

Glu
```

<210> SEQ ID NO 38
<211> LENGTH: 695
<212> TYPE: PRT
<213> ORGANISM: Artificial Sequence
<220> FEATURE:
<223> OTHER INFORMATION: Synthetic: TS-M10, Heavy Chain

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
```

-continued

```
                65                  70                  75                  80
Leu Gln Met Asn Ser Leu Arg Ala Glu Asp Thr Ala Val Tyr Tyr Cys
                    85                  90                  95
Ala Lys Tyr Pro His Tyr Tyr Gly Ser Ser His Trp Tyr Phe Asp Val
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Cys Ser Arg Ser Thr Ser Glu Ser
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                    165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Lys Thr Tyr Thr Cys Asn Val
                195                 200                 205
Asp His Lys Pro Ser Asn Thr Lys Val Asp Lys Arg Val Glu Ser Lys
                210                 215                 220
Tyr Gly Pro Pro Cys Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                    245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
                275                 280                 285
Asn Ala Lys Thr Lys Pro Arg Glu Glu Gln Phe Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                    325                 330                 335
Lys Thr Ile Ser Lys Ala Lys Gly Gln Pro Arg Glu Pro Gln Val Tyr
                340                 345                 350
Thr Leu Pro Pro Ser Gln Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                    405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
                435                 440                 445
Gly Lys Gly Gly Gly Gly Ser Gly Gly Gly Ser Gln Val Gln Leu
                450                 455                 460
Val Glu Ser Gly Gly Gly Val Val Gln Pro Gly Arg Ser Leu Arg Leu
465                 470                 475                 480
Asp Cys Lys Ala Ser Gly Ile Thr Phe Ser Asn Ser Gly Met His Trp
                    485                 490                 495
```

Val Arg Gln Ala Pro Gly Lys Gly Leu Glu Trp Val Ala Val Ile Trp
            500                 505                 510

Tyr Asp Gly Ser Lys Arg Tyr Tyr Ala Asp Ser Val Lys Gly Arg Phe
            515                 520                 525

Thr Ile Ser Arg Asp Asn Ser Lys Asn Thr Leu Phe Leu Gln Met Asn
            530                 535                 540

Ser Leu Arg Ala Glu Asp Thr Ala Val Tyr Tyr Cys Ala Thr Asn Asp
545                 550                 555                 560

Asp Tyr Trp Gly Gln Gly Thr Leu Val Thr Val Ser Ser Gly Gly Gly
            565                 570                 575

Gly Ser Gly Gly Gly Ser Gly Gly Gly Ser Glu Ile Val Leu
            580                 585                 590

Thr Gln Ser Pro Ala Thr Leu Ser Leu Ser Pro Gly Glu Arg Ala Thr
            595                 600                 605

Leu Ser Cys Arg Ala Ser Gln Ser Val Ser Ser Tyr Leu Ala Trp Tyr
            610                 615                 620

Gln Gln Lys Pro Gly Gln Ala Pro Arg Leu Leu Ile Tyr Asp Ala Ser
625                 630                 635                 640

Asn Arg Ala Thr Gly Ile Pro Ala Arg Phe Ser Gly Ser Gly Ser Gly
            645                 650                 655

Thr Asp Phe Thr Leu Thr Ile Ser Ser Leu Glu Pro Glu Asp Phe Ala
            660                 665                 670

Val Tyr Tyr Cys Gln Gln Ser Ser Asn Trp Pro Arg Thr Phe Gly Gln
            675                 680                 685

Gly Thr Lys Val Glu Ile Lys
            690                 695

<210> SEQ ID NO 39
<211> LENGTH: 273
<212> TYPE: PRT
<213> ORGANISM: Artificial Sequence
<220> FEATURE:
<223> OTHER INFORMATION: Synthetic: TS-M10, Light Chain

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Gly Ala Gln Gln Glu Glu
210                 215                 220

Cys Glu Trp Asp Pro Trp Thr Cys Glu His Met Gly Ser Gly Ser Ala
225                 230                 235                 240

Thr Gly Gly Ser Gly Ser Thr Ala Ser Ser Gly Ser Gly Ser Ala Thr
            245                 250                 255

His Gln Glu Glu Cys Glu Trp Asp Pro Trp Thr Cys Glu His Met Leu
            260                 265                 270

Glu

<210> SEQ ID NO 40
<211> LENGTH: 509
<212> TYPE: PRT
<213> ORGANISM: Artificial Sequence
<220> FEATURE:
<223> OTHER INFORMATION: Synthetic

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys Gly Gly Gly Gly Ala Gln Gln Glu Glu Cys Glu Trp Asp
450                 455                 460

Pro Trp Thr Cys Glu His Met Gly Ser Gly Ser Ala Thr Gly Gly Ser
465                 470                 475                 480

Gly Ser Thr Ala Ser Ser Gly Ser Gly Ser Ala Thr His Gln Glu Glu
            485                 490                 495

Cys Glu Trp Asp Pro Trp Thr Cys Glu His Met Leu Glu
        500                 505

<210> SEQ ID NO 41
<211> LENGTH: 499
<212> TYPE: PRT
<213> ORGANISM: Artificial Sequence
<220> FEATURE:
<223> OTHER INFORMATION: Synthetic

<400> SEQUENCE: 41

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

-continued

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys Gly Gly Gly Gly Ala Gln Gln
        435                 440                 445

Glu Glu Cys Glu Trp Asp Pro Trp Thr Cys Glu His Met Gly Ser Gly
450                 455                 460

Ser Ala Thr Gly Gly Ser Gly Ser Thr Ala Ser Ser Gly Ser Gly Ser
465                 470                 475                 480

Ala Thr His Gln Glu Glu Cys Glu Trp Asp Pro Trp Thr Cys Glu His
                485                 490                 495

Met Leu Glu

<210> SEQ ID NO 42

<211> LENGTH: 214
<212> TYPE: PRT
<213> ORGANISM: Artificial Sequence
<220> FEATURE:
<223> OTHER INFORMATION: Synthetic

<400> SEQUENCE: 42

```
Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 43
<211> LENGTH: 214
<212> TYPE: PRT
<213> ORGANISM: Artificial Sequence
<220> FEATURE:
<223> OTHER INFORMATION: Synthetic

<400> SEQUENCE: 43

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Ser Ser Asn Trp Pro Arg
                85                  90                  95
Thr Phe Gly Gln Gly Thr Lys Val Glu Ile Lys Arg Thr Val Ala Ala
```

```
                100             105             110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 44
<211> LENGTH: 512
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
```

Leu Met Ile Ser Arg Thr Pro Glu Val Thr Cys Val Val Asp Val
            245                 250                 255

Ser His Glu Asp Pro Glu Val Lys Phe Asn Trp Tyr Val Asp Gly Val
    260                 265                 270

Glu Val His Asn Ala Lys Thr Lys Pro Cys Glu Glu Gln Tyr Gly Ser
        275                 280                 285

Thr Tyr Arg Cys Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
            325                 330                 335

Gln Val Tyr Thr Leu Pro Pro Ser Arg Lys Glu Met Thr Lys Asn Gln
        340                 345                 350

Val Ser Leu Thr Cys Leu Val Lys Gly Phe Tyr Pro Ser Asp Ile Ala
    355                 360                 365

Val Glu Trp Glu Ser Asn Gly Gln Pro Glu Asn Asn Tyr Lys Thr Thr
370                 375                 380

Pro Pro Val Leu Lys Ser Asp Gly Ser Phe Phe Leu Tyr Ser Lys Leu
            385                 390                 395                 400

Thr Val Asp Lys Ser Arg Trp Gln Gln Gly Asn Val Phe Ser Cys Ser
        405                 410                 415

Val Met His Glu Ala Leu His Asn His Tyr Thr Gln Lys Ser Leu Ser
    420                 425                 430

Leu Ser Pro Gly Lys Gly Gly Gly Gly Ala Gln Gln Glu Glu Cys
435                 440                 445

Glu Trp Asp Pro Trp Thr Cys Glu His Met Gly Ser Gly Ser Ala Thr
            450                 455                 460

Gly Gly Ser Gly Ser Thr Ala Ser Ser Gly Ser Gly Ser Ala Thr His
465                 470                 475                 480

Gln Glu Glu Cys Glu Trp Asp Pro Trp Thr Cys Glu His Met Leu Glu
        485                 490                 495

500                 505                 510

<210> SEQ ID NO 45
<211> LENGTH: 502
<212> TYPE: PRT
<213> ORGANISM: Artificial Sequence
<220> FEATURE:
<223> OTHER INFORMATION: Synthetic

<400> SEQUENCE: 45

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Thr Asn Asp Asp Tyr Trp Gly Gln Gly Thr Leu Val Thr Val Ser

```
                  100                 105                 110
Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Lys Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Cys
            275                 280                 285

Glu Glu Gln Tyr Gly Ser Thr Tyr Arg Cys Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Asp Thr Thr Pro Pro Val Leu Asp Ser Asp Gly Ser Phe
385                 390                 395                 400

Phe Leu Tyr Ser Asp Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gly Gly Gly Gly Gly
            435                 440                 445

Ala Gln Gln Glu Glu Cys Glu Trp Asp Pro Trp Thr Cys Glu His Met
            450                 455                 460

Gly Ser Gly Ser Ala Thr Gly Gly Ser Gly Ser Thr Ala Ser Ser Gly
465                 470                 475                 480

Ser Gly Ser Ala Thr His Gln Glu Glu Cys Glu Trp Asp Pro Trp Thr
                485                 490                 495

Cys Glu His Met Leu Glu
                500

<210> SEQ ID NO 46
```

```
<211> LENGTH: 214
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 214
<212> TYPE: PRT
<213> ORGANISM: Artificial Sequence
<220> FEATURE:
<223> OTHER INFORMATION: Synthetic

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
```

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 48
<211> LENGTH: 453
<212> TYPE: PRT
<213> ORGANISM: Artificial Sequence
<220> FEATURE:
<223> OTHER INFORMATION: Synthetic

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
```

```
                        245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 49
<211> LENGTH: 214
<212> TYPE: PRT
<213> ORGANISM: Artificial Sequence
<220> FEATURE:
<223> OTHER INFORMATION: Synthetic

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

-continued

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210
```

TRISPECIFIC INHIBITORS FOR CANCER TREATMENT

This application claims priority to U.S. Provisional Patent Application Ser. No. 62/312,965, filed Mar. 24, 2016. The entirety of the aforementioned application is incorporated herein by reference.

FIELD

The present application relates generally to cancer treatment and, in particular, to trispecific inhibitors capable of modulating multiple pathways associated with angiogenesis and antitumor immunity.

BACKGROUND

Although an increasing number of therapeutic monoclonal antibodies have been approved for treatment of various cancers, emergence of resistance to these antibodies is frequently observed, given the many different molecular pathways underlying cancer growth and progression to metastasis.

Angiogenesis, the development of new blood vessels from pre-existing vessels, is essential for tumor growth and metastasis. Angiogenesis inhibition presents a potentially valuable strategy for treating diseases, such as cancer, in which progression (e.g., metastasis) is dependent on neovascularization. Two important angiogenesis pathways include the vascular endothelial growth factor (VEGF) pathway and the Tie2 pathway. The principal VEGF pathway is mediated by the transmembrane tyrosine kinase VEGF-R2. Various isoforms of VEGF, particularly VEGF-A, bind to VEGF-R2, resulting in dimerization and activation through phosphorylation of various downstream tyrosine kinases. The Tie2 pathway is another angiogenesis pathway for which therapeutic antibodies and small molecule drugs have been developed. The Tie2 tyrosine kinase receptor activates angiogenesis in response to binding by one its angiopoietin (Ang) ligands (i.e., Ang1, Ang2, Ang3 (mouse) and Ang4).

In addition to the role of angiogenesis in cancer progression, the inability of the host to eliminate cancer cells is another major problem. Although the immune system is the principal mechanism of cancer prevention, cancer cells counteract immunosurveillance. Natural control mechanisms have been identified that limit T-cell activation so as to prevent collateral damage resulting from unrestrained T-cell activity. This process has been exploited by tumor cells to evade immune responses. Restoring the capacity of immune effector cells, especially T cells, to recognize and eliminate cancer is a major objective in immunotherapy. Therefore, there is still a need for more effective cancer treatment.

SUMMARY

The present application provides compositions and methods to effectively inhibit cancer growth by simultaneously reducing angiogenesis in tumor tissue and enhancing antitumor immunity. One aspect of the present application relates to a trispecific inhibitor comprising a first targeting domain with a binding specificity to VEGF or a receptor of VEGF; a second targeting domain with a binding specificity to an immune checkpoint regulator; and a third targeting domain with a binding specificity to a Tie2 receptor or a Tie2 receptor ligand. Each binding specificity is conferred by one or more antibody variable regions, peptide inhibitors, dominant negative proteins, small molecule drugs or combination thereof. In some embodiments, the trispecific inhibitor comprises one or more polypeptides. In some embodiments, the trispecific inhibitor is a trispecific antibody. In some embodiments, the trispecific antibody has three or more binding specificities. In some embodiments, the trispecific antibody has only three binding specificities.

In some embodiments, the targeting domains are linked to one another by peptide bonds via peptide linkers or through covalent conjugates using appropriate crosslinking technologies known in the art.

In some embodiments, at least two of the three targeting domains comprise antibody variable regions. In some embodiments, the targeting domains are in the form of a single domain antibody (sdAb), a fragment variable (Fv) heterodimer, a single chain Fv (scFv), a Fab fragment, a TriFab, or a combination thereof.

In some embodiments, the first and the second targeting domains comprise antibody variable regions and the third targeting domain comprise an inhibitory peptide. In some embodiments, the inhibitory peptide comprises the amino acid sequence of SEQ ID NO:1 or SEQ ID NO:2.

In some embodiments, the first targeting domain comprises one or more complementarity determining regions (CDRs) from bevacizumab, and the second targeting domain comprises one or more CDRs from an anti-PD-L1 antibody.

In some embodiments, the targeting domains in the trispecific antibody are linked to an oligomeric protein scaffold. In other embodiments, the targeting domains are linked to one another by polypeptide linkers without an oligomeric binding scaffold.

The oligomeric protein scaffold may be a dimer, trimer or tetramer. In some embodiments, the oligomeric protein scaffold comprises one or more immunoglobulin constant regions forming a homodimer. In some embodiments, the oligomeric protein scaffold comprises one or more immunoglobulin constant regions forming a heterodimer. In some embodiments, the heterodimeric scaffold comprises two different monomers wherein at one monomer comprises a modified CH2 or CH3 region of an immunoglobulin. In some embodiments, the oligomeric protein scaffold comprises two leucine zipper domains forming a homodimer or heterodimer. In some embodiments, a dimeric protein scaffold comprises a leucine zipper from the jun transcription factor associated with a leucine zipper from the fos transcription factor.

In some embodiments, one or more targeting domains in the trispecific inhibitor are configured as amino-terminal polypeptide arms covalently joined to the protein scaffold and projecting therefrom. The polypeptide arm may comprise one polypeptide chain or two polypeptide chains associated with one another. In each arm, one polypeptide chain is covalently linked to a monomer of the oligomeric protein scaffold.

In some embodiments, at least two targeting domains are linked to the oligomeric protein scaffold, whereby each targeting domain comprises a polypeptide arm projecting from the scaffold, and each arm comprises at least one polypeptide chain covalently linked to a monomer of the oligomeric protein scaffold.

In some embodiments, the trispecific inhibitor comprises a dimeric protein scaffold containing one or more immunoglobulin constant regions (e.g., CH2-CH3) forming a homodimer with two arms projecting from the amino terminal side of the dimeric protein scaffold, whereby each arm contains two polypeptide chains associated with one another, including one covalently linked to a particular monomer in the dimeric scaffold, whereby each arm comprises immunoglobulin variable regions corresponding to two different binding specificities (e.g., VH2-VH1 and VL2-VL1). Each arm may further contains an immunoglobulin constant region (e.g., CH1, CL). In this case, the immunoglobulin constant region may be positioned between the two binding specificities or on the carboxy-terminal end of the two binding specificities.

In some embodiments, the trispecific inhibitor comprises a dimeric protein scaffold containing one or more immunoglobulin constant regions forming a homodimer with two pairs of single chain arms, each pair projecting from an opposite end of the dimeric protein scaffold. In this case, a first pair of arms projects from the amino terminal end of the dimeric scaffold and a second pair of arms projects from the carboxy terminal end of the dimeric protein scaffold. Each arm in the first pair of arms comprises the first targeting domain, while each arm in the second pair of arms comprises the second targeting domain. The third targeting domain is covalently attached to either end or both ends of the pair of arms. Each arm contains a single polypeptide chain covalently linked to a single polypeptide chain in the dimeric scaffold, whereby the first pair of arms contains a VH1 domain fused to a VL1 domain and the second pair of arms contains a VH2 domain fused to a VL2 domain.

In certain embodiments, the trispecific inhibitor comprises a dimeric protein scaffold comprising two mutant immunoglobulin constant region chains forming a "knobs-into-holes" heterodimer. In other embodiments, the dimeric protein scaffold comprises two leucine zipper chains forming a heterodimer.

In some embodiments, two arms project from a heterodimeric protein scaffold in which a first arm comprises a first Fab fragment comprising the first targeting domain and the second arm comprises a second Fab fragment comprising the second targeting domain. In one embodiment, the heterodimeric protein scaffold comprises one or more immunoglobulin constant regions, including CH3, whereby one or more mutations in each of the two polypeptide chains result in a knobs-into-holes heterodimeric protein scaffold that prevents mispairing of heavy chains with one binding specificity to heavy chains of a different binding specificity when co-expressing the polypeptide chains of the trispecific inhibitor. In this embodiment, each of the two arms includes one more mutations in the constant regions in each of the first and second Fab fragments (e.g., CH1 and/or CL) so as to prevent mispairing of light chains from one binding specificity (e.g., VL1) to light chains of a different binding specificity (e.g., VL2) when co-expressing the polypeptide light chains in the trispecific inhibitor.

In other embodiments, an alternative approach to preventing mispairing of light chains involves preparing a trispecific antibody with two arms project from the heterodimeric protein scaffold, where a first arm comprises a first Fab fragment comprising the first targeting domain and the second arm comprises a second Fab fragment comprising the second targeting domain, which is further modified relative to the first Fab fragment. Each of the two Fab fragments comprise VH, VL, CH1, and CL domains. However, whereas the polypeptide chain of the first arm that is covalently joined to one of the two polypeptide chains of the dimeric protein scaffold contains a VH1-CH1 peptide associated with a VL1-CL peptide, the polypeptide chain of the second arm that is covalently joined to the other polypeptide chain of the dimeric protein scaffold is either: (1) a VL-CL peptide associated with the VL-CL peptide; (2) a VL-CH1 peptide associated with a VH-CL peptide; or (3) a VH-CL peptide associated with a VL-CH1 peptide.

In another embodiment, the trispecific inhibitor contains two single chain arms projecting from a heterodimeric protein scaffold, including a first arm comprising a single polypeptide chain comprising VH1 and VL1 regions constituting the first targeting domain and a second arm comprising a single polypeptide chain comprising VH2 and VL2 regions constituting the second targeting domain. In another embodiment, the trispecific inhibitor contains two single chain arms projecting from a heterodimeric protein scaffold, including a first arm comprising a single polypeptide chain comprising a VH1 domain from the first targeting domain fused to a VL2 region from the second targeting domain and the second arm comprising a single polypeptide chain comprising a VH2 region from the second targeting domain fused to a VL1 region from the first targeting domain.

In a further embodiment, the trispecific inhibitor contains four arms projecting from the dimeric protein scaffold, including a first pair of arms projecting from the amino terminal end of the dimeric scaffold and a second pair of arms projecting from the carboxy terminal end of the dimeric protein scaffold. In this case, each arm includes a single polypeptide chain covalently linked to a single polypeptide chain in the dimeric scaffold, where the first pair of arms includes a first arm containing a VH1 region fused to CH1 region and a second arm containing a VL1 region fused to a CL1 region. Together, these two arms form the first binding specificity. The second pair of arms includes a third arm containing a VH2 region fused to CH1 region and a fourth arm containing a VL2 region fused to a CL1 region, where the third and fourth arms form the second binding specificity.

Another aspect of the present application relates to a trispecific antibody, comprising: a first targeting domain having a first binding specificity to an immune checkpoint regulator; a second targeting domain having a second binding specificity to vascular endothelial growth factor (VEGF) or a vascular endothelial growth factor receptor (VEGFR); and a third targeting domain having a third binding specificity to a ligand of Tie2 tyrosine kinase receptor or to a Tie2 tyrosine kinase receptor, wherein the first targeting domain and the second targeting domain each comprises one or more antibody variable regions.

Another aspect of the present application relates to a method for treating a cell proliferative disorder, comprising administering to a subject in need thereof the trispecific inhibitor or the trispecific antibody of the present application in an amount effective to treat the proliferative disorder.

BRIEF DESCRIPTION OF THE DRAWINGS

FIGS. 1A and 1B depict exemplary homodimeric embodiments containing double chain arms with dual binding specificities. Inhibitory peptides corresponding to the third binding specificity (represented by circles) are covalently linked at the carboxy terminal end of each monomer in the homodimeric scaffold. FIGS. 1C and 1D depict exemplary homodimeric embodiments containing a pair of single chain arms on one side the homodimeric scaffold corresponding to one binding specificity and a second pair of single chain arms on the other side of the homodimeric scaffold corresponding to a second binding specificity. Inhibitory peptides corresponding to the third binding specificity (represented by circles) are covalently linked at the amino terminal ends in each of the first pair of arms and at the carboxy terminal ends in each of the second pair of arms.

FIG. 2A depicts an exemplary heterodimeric trispecific antibody embodiment containing two double chain arms, each arm comprising a different binding specificity. FIGS. 2B and 2C depict exemplary heterodimeric embodiments comprising two scFv arms. In each of FIGS. 2A-2C, inhibitory peptides corresponding to the third binding specificity (represented by circles) are covalently linked at the carboxy terminal end of each monomer in the heterodimeric scaffold.

FIGS. 3A-3C contain two double chain Fab arms in which the first Fab arm (on the left) is left untouched relative to FIG. 2A, while the other Fab arm (on the right) with the other binding specificity is modified by swapping one or more domains in the light chain with one or more domains in the heavy chain at the heavy chain:light chain interface. Inhibitory peptides corresponding to the third binding specificity (represented by circles) are covalently linked at the carboxy terminal end of each monomer in the heterodimeric scaffold.

FIGS. 4A and 4B contain four single chain arms projecting from the heterodimeric scaffold. In FIG. 4A, the pair of arms above the scaffold constitute the first binding specificity and the pair of arms below the scaffold constitute the second binding specificity. In FIG. 4B, scFv arms comprising one of two binding specificities are present above and below the scaffold. Inhibitory peptides corresponding to the third binding specificity (represented by circles) are covalently linked at the amino terminal ends in each of the first pair of arms and at the carboxy terminal ends in each of the second pair of arms.

FIG. 5A depicts an anti-PD1 Fab region binding determinant (VH1:VL1), including sequences for the variable heavy (VH1) (SEQ ID NO:14) and variable light (VL1) (SEQ ID NO:16) regions. FIG. 5B depicts an anti-bevacizumab Fab region binding determinant (VH1:VL1), including sequences for the variable heavy (VH1) (SEQ ID NO:6) and variable light (VL1) (SEQ ID NO:7) regions. FIG. 5C depicts the sequence corresponding to the trebanabib TBN-P peptide (SEQ ID NO: 1).

FIGS. 8A and 8B depict the structural configurations of two exemplary trispecific antibody embodiments, TS-M5 (FIG. 8A) and TS-M6 (FIG. 8B), each comprising a homodimeric scaffold in accordance with certain aspects of the present disclosure. Each of these two configurations includes a pair of TBN peptides fused to the C-terminal end of the two heavy chains, along with pairs of anti-PD1 determinants and anti-VEGF determinants separated by CH1:CL regions in each of the two arms. FIG. 8C shows a PAGE gel of recombinant BVZ control mAb, a recombinant BVZ antibody with trebananib peptide fused to the C-terminal ends of the two BVZ heavy chains (BVZ-TBN-P), TS-M5 and the MWM. The amino acid sequences of the heavy chain and light chain of TS-M5 are shown in SEQ ID NOS:28 and 29, respectively. The amino acid sequences of the heavy chain and light chain of TS-M6 are shown in SEQ ID NOS:30 and 31, respectively.

FIGS. 10A and 10B depict the structural configurations of two exemplary trispecific antibody embodiments, TS-M9 (FIG. 10A) and TS-M10 (FIG. 10B), each comprising a homodimeric scaffold in accordance with certain aspects of the present disclosure. Each of these two configurations includes a pair of scFvs directed against PD-1 or VEGF, which are fused to the C-terminal end of the two heavy chains and a pair of TBN peptides fused to the C-terminal end of the two light chains. FIG. 10C shows a PAGE gel of recombinant BVZ control mAb, TS-M10 and the MWM. The amino acid sequences of the heavy chain and light chain of TS-M9 are shown in SEQ ID NOS:36 and 37, respectively. The amino acid sequences of the heavy chain and light chain of TS-10 are shown in SEQ ID NOS:38 and 39, respectively.

FIGS. 12A-12G depict the ability of trispecific antibodies to block PD-1/PD-L1 interactions. The antibodies tested include TS-M1 (FIG. 12A), TS-M2 (FIG. 12B), TS-M3 (FIG. 12C), TS-M4 (FIG. 12D), TS-M10 (FIG. 12E), monospecific anti-PD-1 control (FIG. 12F) and bispecific anti-PD-1-TBN-P control (FIG. 12G). Half-maximal inhibitory concentrations ($IC_{50}$) were determined for each antibody based on the resulting mean fluorescence intensities measured following co-incubation of human PD-1 expressing cells with different concentrations of each antibody in combination with FITC-labeled human PD-1.

FIGS. 18A-18F depicts the results of binding affinity assays of trispecific antibody binding to human VEGF. The antibodies tested included bevacizumab mAb as a positive control (FIG. 18A), TS-M1 (FIG. 18B), TS-M3 (FIG. 18C), TS-M4 (FIG. 18D), TS-M2 (FIG. 18E), and TS-M10 (FIG. 18F). Serial dilutions of the test antibodies were co-incubated with recombinant human VEGF 165, and then further incubated with anti-human Fc antibody (goat-IgG), anti-goat IgG-HRP antibody and TMB substrate to detect binding signals by measurement of light absorbance at 650 nM. Corresponding EC50 values were calculated based on the concentration of antibody resulting in half-maximal binding as measured by the extent of light absorbance at 650 nM. The negative control anti-PD-1-TBN-P antibody was co-incubated with the test antibodies in each case.

In FIG. 20A, fresh PBMCs (Bioreclamation Inc.) were incubated with 2 μg/ml Staphylococcal Enterotoxin B (SEB, Toxin Technology Inc.) for 3 days. 30,000 of NCI-H358 human lung adenocarcinoma cells (ATCC) were added to provide an inhibitory PD-L1 signal. 64 nM of anti-PD-1 mAb (Nivolumab, "Nivo"), trispecific antibodies (TS10, TS1, TS2, TS3 and TS4) or isotype control Ab were added to block the inhibitory PD-L1 activities, hence activation of T cells. Supernatants were collected to measure the production of IFN-γ by ELISA. In FIG. 20B, fresh PBMC (Bioreclamation Inc.) were pre-activated by anti-CD3 (Bio-X-cell) and anti-CD28 (Biolegend) for 6 days. After resting, 100,000 of CellTrace Far Red (ThermoFisher) labeled PBMC were activated by 1 μg/ml SEB for 4 days. 20,000 NCI-H358 cells were added to provide an inhibitory PD-L1 signal. 64 nM of anti-PD-1 mAb (Nivolumab), trispecific antibodies (TS10, TS1, TS2 and TS3) or isotype control Ab were added to block the inhibitory PD-L1 signal. T cell proliferation index were calculated based on the reduction of mean fluorescence intensity reduction of CellTrace Far Red signal on gated CD3+ T cells.

DETAILED DESCRIPTION

Definitions

Figure 1A:
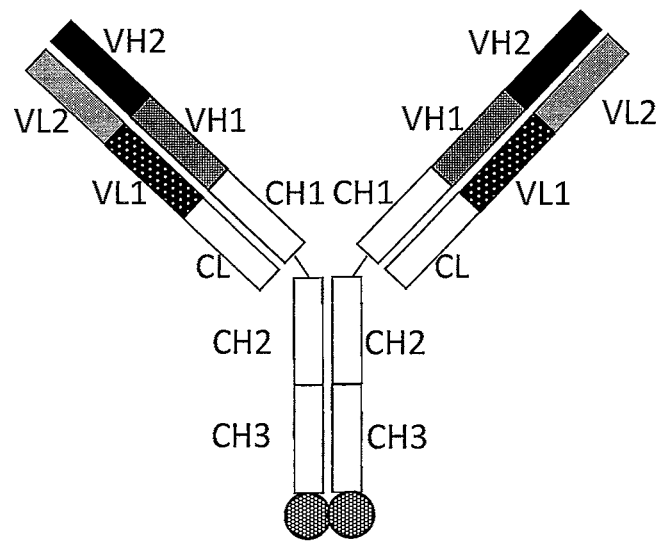
FIGS. 1A-1D depict various trispecific antibody embodiments comprising a homodimer scaffold in accordance with certain aspects of the present disclosure.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent, pending patent application or patent application publication described in this application is expressly incorporated by reference herein.

As used herein, the phrase "trispecific inhibitor" refers to a molecule comprising at least three targeting domains with different binding specificities. Each targeting domain is capable of binding specifically to a target molecule and inhibiting a biological function of the target molecule upon binding to the target molecule. In some embodiments, the trispecific inhibitor is a polymeric molecule having two or more peptides. In some embodiments, the targeting domain comprises a Tie2 tyrosine kinase receptor antagonist domain, a VEGF binding antagonist domain or an immune checkpoint regulator binding antagonist domain. In some embodiments, the targeting domain comprises an antigen binding domain or a CDR of an antibody.

As used herein, the phrase "trispecific antibody" refers to an antibody comprising a plurality of immunoglobulin antigen binding domains and at least three different targeting domains with different binding specificities. As such, the trispecific antibody may encompass a complete antibody with variable and constant regions from both immunoglobulin heavy and light chains, as well as antibody fragments thereof.

When describing polypeptide domain arrangements with hyphens between individual domains (e.g., CH2-CH3), it should be understood that the order of the listed domains is from the amino terminal end to the carboxy terminal end.

The term "Tie2 tyrosine kinase receptor binding antagonist" refers to a functional class of agents that bind to a Tie2 tyrosine kinase receptor or one of its ligands so that, as a result of the binding, activation of the Tie2 tyrosine kinase receptor by one or more of its ligands (i.e., Ang1, Ang2, Ang3 and Ang4) is blocked or inhibited. As used herein, the term "Tie2 tyrosine kinase receptor binding antagonist" include antibody fragments, peptide inhibitors, dominant negative peptides and small molecule drugs, either in isolated forms or as part of a fusion protein or conjugate.

The phrase "VEGF binding antagonist" refers to a functional class of agents that bind to VEGF-A or its receptor, VEGFR-2, so that, as a result of the binding, activation of VEGFR-2 by VEGF-A is blocked or inhibited. As used herein, the term "VEGF binding antagonists" include antibody fragments, peptide inhibitors, dominant negative peptides and small molecule drugs, either in isolated forms or as part of a fusion protein or conjugate.

As used herein, the phrase "immune checkpoint regulator" refers to a functional class of agents, which inhibit or stimulate signaling through an immune checkpoint regulator. An "immune checkpoint regulator" includes receptors and their associated ligands, which together provide a means for inhibiting or stimulating signaling pathways that otherwise lead to T-cell activation.

The phrases "immune checkpoint binding antagonist" and "immune checkpoint antagonist" are used interchangeably herein with reference to a class of immune checkpoint regulators that interfere with (or inhibit) the activity of an immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. Exemplary immune checkpoint antagonists include, but are not limited to PD-1 and its ligands, PD-L1 and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; T cell Ig and ITIM domain (TIGIT) and its CD155 ligand; CD122 and its CD122R ligand; CD70, B7H3, B and T lymphocyte attenuator (BTLA), and VISTA. Immune checkpoint regulator antagonists include antibody fragments, peptide inhibitors, dominant negative peptides and small molecule drugs, either in isolated forms or as part of a fusion protein or conjugate.

The phrases "immune checkpoint binding agonist" and "immune checkpoint agonist" are used interchangeably herein with reference to a class of immune checkpoint regulators that stimulate the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. Exemplary immune checkpoint regulator agonists include, but are not limited to members of the tumor necrosis factor (TNF) receptor superfamily, such as CD27, CD40, OX40, glucocorticoid-induced TNFR family-related protein (GITR) and CD137 and their ligands. Additional checkpoint regulator agonists belong to the B7-CD28 superfamily, including CD28 and ICOS.

The phrases "dominant-negative protein" or "dominant-negative peptide" refer to a protein or peptide derived from a wild type protein that has been genetically modified by mutation and/or deletion so that the modified protein or peptide interferes with the function of the endogenous wild-type protein from which it is derived.

The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

As used herein, the term "recombinant" refers to polypeptides or polynucleotides that do not exist naturally and which may be created by combining polynucleotides or polypeptides in arrangements that would not normally occur together. The trispecific antibodies described herein are by definition "recombinant."

As used herein, the term "antibody" refers to a polypeptide or a polypeptide complex that specifically recognizes and binds to an antigen through one or more immunoglobulin variable regions. An antibody can be a whole antibody, an antigen binding fragment or a single chain thereof.

The terms "antibody fragment" or "antigen-binding fragment" are used with reference to a portion of an antibody, such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered proteins comprising immunoglobulin variable regions that act like an antibody by binding to a specific antigen to form a complex.

A "single-chain fragment variable" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker.

As used herein, the terms "VH1" and "VH2" refer to immunoglobulin heavy chain variable domains corresponding to two different binding specificities. Likewise, the terms "VL1" and "VL2" refer to light chain variable domains corresponding to two different binding specificities. When used together, it is to be understood that VH1 and VL1 regions define a common binding specificity and that VH2 and VL2 domains define a second binding specificity The term "antibody" encompasses various broad classes of polypeptides that can be distinguished biochemically. Those skilled in the art will appreciate that heavy chains are classified as alpha, delta, epsilon, gamma, and mu, or α, δ, ε, γ and μ) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are within the scope of the present disclosure, the following discussion will generally be directed to the IgG class of immunoglobulin molecules. With regard to IgGs, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration where the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library and anti-idiotypic (anti-Id) antibodies. Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains in conventional antibodies increases as they become more distal from the antigen-binding site or amino-terminus of the antibody. In conventional antibodies, the N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. CDR-H1, CDR-H2, CDR-H3, CDR-L1, CDR-L2 and CDR-L3). In some instances, e.g., certain immunoglobulin molecules are derived from camelid species or engineered based on camelid immunoglobulins. Alternatively, an immunoglobulin molecule may consist of heavy chains only, with no light chains or light chains only, with no heavy chains.

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined.

Antibodies disclosed herein may be from any animal origin, including birds and mammals. Preferably, the antibodies are human, murine, donkey, rabbit, goat, guinea pig, camel, llama, horse, or chicken antibodies. In some embodiments, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In some embodiments, a polypeptide of the disclosure comprises a polypeptide chain comprising a CH3 domain. Further, an antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain. A "light chain-heavy chain pair" refers to the collection of a light chain and heavy chain that can form a dimer through a disulfide bond between the CL domain of the light chain and the CH1 domain of the heavy chain.

The subunit structures and three dimensional configurations of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains.

As used herein the term "disulfide bond" includes a covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the phrase "humanized antibody" refers to an antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans.

As used herein, the phrase "chimeric antibody," refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

Included within the scope of the trispecific antibodies of the present application are various compositions and methodologies, including asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), $mAb^2$ (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec, TvAb, Roche); scFv/Fc fusions; SCORPION (Emergent BioSolutions/Trubion, ZymoGenetics/BMS); dual affinity retargeting technology (Fc-DART), MacroGenics; dual $(scFv)_2$-Fabs (National Research Center for Antibody Medicine); $F(ab)_2$ fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunGene, ImmunoMedics).

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

The term "immunoconjugate" refers to a trispecific antibody which is fused by covalent linkage to a peptide or small molecule drug. The peptide or small molecule drug can be linked to the C-terminus of a constant heavy chain or to the N-terminus of a variable light and/or heavy chain. A "linker" may be used to link the peptide or small molecule drug, such as a maytansinoid, to the trispecific antibody in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art. The immunoconjugate may further include a flexible 3-15 amino acid peptide (or spacer) between the trispecific antibody and the peptide and/or small molecule drug.

The terms "treat" and "treatment" refer to the amelioration of one or more symptoms associated with a cell proliferative disorder, prevention or delay of the onset of one or more symptoms of a cell proliferative disorder; and/or lessening of the severity or frequency of one or more symptoms of cell proliferative disorder.

The phrases "to a patient in need thereof", "to a patient in need of treatment" or "a subject in need of treatment" includes subjects, such as mammalian subjects, that would benefit from administration of the trispecific inhibitor of the present disclosure for treatment of a cell proliferative disorder.

The terms "therapeutically effective amount", "pharmacologically effective amount", and "physiologically effective amount" are used interchangeably to mean the amount of a trispecific inhibitor that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same cell proliferative disorder as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

The term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm or tumor, which is an abnormal growth of tissue. "Cancer" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancer of the brain, bladder, breast, cervix, colon, head and neck, kidney, lung, non-small cell lung, mesothelioma, ovary, prostate, stomach and uterus, leukemia, and medulloblastoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia Schilling's leukemia, stem cell leukemia, subleukemic leukemia, and undifferentiated cell leukemia.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

Trispecific Inhibitors

One aspect of the present application relates to a trispecific inhibitor. The trispecific inhibitor comprises a first targeting domain having a first binding specificity conferred by one or more VEGF binding antagonists, a second targeting domain having a second binding specificity conferred by one or more checkpoint regulators, and a third targeting domain having a third binding specificity conferred by one or more Tie2 receptor binding antagonists. A given targeting domain may be in the form of one or more antibody fragments comprising an antigen-binding domain, a peptide inhibitor, a dominant negative peptide, or a small molecule drug. In certain embodiments, one or more of the peptide inhibitors, dominant negative peptides or small molecule drugs are fused to or conjugated to immunoglobulin constant region, immunoglobulin Fc fragment or an oligomeric protein scaffold described herein.

In some embodiments, the trispecific inhibitor is a trispecific antibody and the binding antagonists and/or regulators include an antibody fragment comprising an antigen-binding domain containing one more immunoglobulin variable regions (e.g., VH1, VH2, VL1, VL2) and their associated complementarity derived regions (CDRs) and framework regions (FRs) in immunoglobulin heavy and light chains. The antibody fragment may comprise a single polypeptide chain or a pair of polypeptide chains associated with one another. The sequences from these regions may be determined experimentally by conventional methods or they may be identified from published immunoglobulin heavy and light chain sequences.

In one embodiment, at least two of the three binding specificities are conferred by antibody variable regions. In another embodiment, all three of the binding specificities are conferred by antibody variable regions. Where the binding specificities are conferred by antibody variable regions, the binding antagonists may be in the form of any suitable antibody fragment that can bind an antagonist target, such as a single domain antibody (sdAb), a fragment variable (Fv) heterodimer, single-chain fragment variable (scFv), a Fab fragment or a combination thereof.

In certain preferred embodiments, the binding antagonists in the trispecific antibody are linked to an oligomeric protein scaffold, such as an immunoglobulin constant region or Fc fragment. The binding antagonists may be fused (e.g., by peptide bonds) or chemically conjugated to the oligomeric protein scaffold. When linked to an oligomeric scaffold, the binding antagonists may be configured as single or double chain polypeptide "arms" projecting from the amino- and/or carboxy terminal ends of the oligomeric scaffold.

In other embodiments, the binding antagonists may be chemically linked (by peptide bonds of chemical conjugation) to one another by polypeptide linkers without an oligomeric binding scaffold. In either case, flexible peptide linkers may be incorporated between two different binding antagonists to separate their respective binding domains into independently functional binding units. Peptide linkers may also be used for linking individual immunoglobulin binding domains to one another in e.g., scFvs and the like. Exemplary peptide linkers are described in Table 1 of U.S. Patent Application Publication No. 2016/009823.

The oligomeric protein scaffold may be a dimer, trimer or tetramer. In one embodiment, the oligomeric protein scaffold comprises one or more immunoglobulin constant regions forming a homodimeric protein scaffold. Alternatively, the oligomeric protein scaffold may be in the form of a heterodimeric protein scaffold. As used herein, the terms "heterodimer" or "heterodimeric" refer to a dimer comprising two non-identical monomers that preferentially associate with one another over either one with itself when co-expressed in a cell. The oligomeric protein scaffold may contain immunoglobulin constant regions (e.g., CH1, CH2, CH3) from e.g., any IgG isotype (e.g., IgG1, IgG2, IgG3, IgG4, IgG5), IgA subtype (e.g., IgA1 and IgA2) or other immunoglobulin antibody class (e.g., IgM, IgD, IgA, and IgY).

In some embodiments, the oligomeric protein scaffold includes a pair of leucine zipper domains for forming a homodimer or heterodimer. A leucine zipper is a common three-dimensional structural motif in proteins, typically as part of a DNA-binding domain in various transcription factors. A single LZ typically contains 4-5 leucine residues at approximately 7-residue intervals, which forms an amphipathic alpha helix with a hydrophobic region running along one side. In a particular embodiment, a heterodimeric protein scaffold comprises a LZ from the c-jun transcription factor associated with a LZ from the c-fos transcription factor. Although c-jun is known to form jun-jun homodimers and c-fos does not form homodimers, the formation of jun-fos heterodimers is greatly favored over jun-jun homodimers. The leucine zipper may be used as the sole dimerization interface in the scaffold. Alternatively, it may be employed in combination with CH2 and/CH2 domains, preferably at the carboxy terminal end of the scaffold.

In another embodiment, the oligomeric protein scaffold and antigen binding arms comprise a TriFab, which is an IgG-shaped bispecific antibody composed of two regular Fab arms fused via flexible linker peptides to one asymmetric third Fab-sized binding module. This third module replaces the IgG Fc region and is composed of the variable region of the heavy chain (VH) fused to CH3 with "knob"-mutations, where the variable region of the light chain (VL) is fused to CH3 with matching "holes". The hinge region does not contain disulfides to facilitate antigen access to the third binding site. To compensate for the loss of hinge-disulfides between heavy chains, CH3 knob-hole heterodimers are linked by S354C-Y349C disulfides, and VH and VL of the stem region may be linked via VH44C-VL100C disulfides. TriFabs are described in Mayer et al., Int. J. Mol. Sci., 16:27497-27507 (2015).

In another embodiment, the oligomeric protein scaffold is a trimer or tetramer comprising three or four monomeric proteins, respectively, each comprising a trimerization or tetramerization domain. In particular embodiments, each monomeric protein in a trimeric protein scaffold comprises a noncollagenous trimerization domain from human collagen XV or human collagen XVII, or a trimerization domain from tumor necrosis factor alpha (TNF-α). Trimerization and tetramerization domain sequences sequences for use in the trispecific antibodies of the present application are described in U.S. Patent Application Nos. 2015/0139991, 20015/0038682, and 2014/0348826.

VEGF Binding Antagonists

The trispecific antibody includes at least one VEGF binding antagonist. The VEGF binding antagonist binds to VEGF-A or its receptor VEGFR-2 so that, as a result of the binding, activation of VEGFR-2 by VEGF-A is blocked or inhibited. A preferred VEGF antibody antagonist is bevacizumab (AVASTIN™), a humanized antibody. Bevacizumab comprises mutated human IgG1 framework regions and antigen-binding complementarity-determining regions from the murine anti-hVEGF monoclonal antibody A.4.6.1 that blocks binding of human VEGF-A to VEGFR-2. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated.

The bevacizumab heavy chain has the following amino acid sequence:

(SEQ ID NO: 48)
EVQLVESGGGLVQPGGSLRLSCAASGYTFTNYGMNWVRQAPGKGLEWVGW

INTYTGEPTYAADFKRRFTFSLDTSKSTAYLQMNSLRAEDTAVYYCAKYP

HYYGSSHWYFDVWGQGTLVTVSSASTKGPSVFPLAPSSKSTSGGTAALGC

LVKDYFPEPVTVSWNSGALTSGVHTFPAVLQSSGLYSLSSVVTVPSSSLG

TQQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPRE

-continued
EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL

SPGK.

The underlined sequence identifies the bevacizumab heavy chain variable region. In certain embodiments, the trispecific inhibitor may include the bevacizumab heavy chain variable region without the associated constant regions The bevacizumab light chain has the following amino acid sequence:

(SEQ ID NO: 49)
DIQMTQSPSSLSASVGDRVTITCSASQDISNYLNWYQQKPGKAPKVLIYF

TSSLHSGVPSRFSGSGSGTDFTLTISSLQPEDFATYYCQQYSTVPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The underlined sequence identifies the bevacizumab heavy chain variable region. In certain embodiments, the trispecific inhibitor may include the bevacizumab heavy chain variable region without the associated constant regions Bevacizumab and other humanized anti-VEGF antibodies are further described in U.S. Pat. No. 6,884,879.

In some embodiments, the VEGF binding antagonist comprises one or more amino acid sequences selected from the group consisting of GYTFTNYGMN (SEQ ID NO:8), WINTYTGEPTYAADFKR (SEQ ID NO:9), YPHYYGSSHWYFDV (SEQ ID NO:10), SASQDISNYLN (SEQ ID NO:11) and QQYSTVPWTF (SEQ ID NO:12).

Additional anti-VEGF antibodies include ranibizumab (trade name LUCENTIS™), a monoclonal antibody fragment derived from the same parent murine antibody as bevacizumab; the G6 or B20 series antibodies (e.g., G6-23, G6-31, B20-4.1) described in U.S. Publication No. 2006/0280747, 2007/0141065 and/or 2007/0020267, as well the antibodies described in U.S. Pat. Nos. 7,060,269, 6,884,879, 6,582,959, 6,703,020; 6,054,297; U.S. Patent Application Publication Nos. US2007/059312, US 2006/009360, US 2005/0186208, US 2003/0206899, US 2003/0190317, and US 2003/0203409.

An exemplary dominant negative anti-VEGF antagonist is Aflibercept, a recombinant fusion protein containing VEGF-A binding portions from the extracellular domains of human VEGF receptors 1 and 2 fused to the human IgG1 Fc portion. Aflibercept acts as a soluble receptor decoy for VEGF-A.

An exemplary anti-VEGFR-2 antagonist is the humanized IgG1 monoclonal antibody, Ramucirumab, which binds to the extracellular domain of VEGFR-2, thereby blocking its interaction with VEGF-A.

Exemplary small molecule antagonists of the VEGF pathway include multikinase inhibitors of VEGFR-2, including sunitinib, sorafenib, cediranib, pazonpanib and nintedanib.

Tie2 Receptor Binding Antagonists

The trispecific antibody further includes a targeting domain containing at least one Tie2 receptor binding antagonist. The Tie2 receptor binding antagonist binds to the Tie2 tyrosine kinase receptor or one of its angiopoietin (Ang) ligands (i.e., Ang-1, Ang-2, Ang-3 and Ang-4) so that, as a result of the binding, activation of the Tie2 receptor by one or more of its ligands is blocked or inhibited. In one embodiment, the Tie2 receptor binding antagonist is an inhibitory peptide from trebanabin, TBN-P. In a specific embodiment, the inhibitory peptide comprises the amino acid sequence in SEQ ID NO:1, i.e., AQQEECEWDPWT-CEHMGSGSATGGSGSTASSGSGSATHQEECE-WDPWTCEHMLE. In another embodiment, the Tie2 receptor binding antagonist comprises trebanabin, which includes the peptide of SEQ ID NO:1 (i.e., TBN-P) fused to an Ig Fc fragment. An exemplary TBN-P-IgG includes the following sequence, whereby the TBN-P region is underlined:

(SEQ ID NO: 2)
DKTHTCPPCPAPELLGGPSVFLFPPKPKDTLMISRTPEVTCVVVDVSHED

PEVKFNWYVDGVEVHNAKTKPREEQYNSTYVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGKGGGGG<u>AQQEECEWDPWTCEHMGSG</u>

<u>SATGGSGSTASSGSGSATHQEECEWDPWTCEHMLE</u>.

Other peptide inhibitors of Tie2 activation (including Ang-2 inhibitors) include A-11 (Compugen), which comprises the amino acid sequence ETFLSTNKLENQ (SEQ ID NO:3); the CVX-060 peptide QK(Ac)YQPLDEK(Ac)DK(0P)TLYDQFMLQQG (SEQ ID NO:4, Pfizer); the CVX-037 peptide (DFB)TNFMPMDDLEK(0P)RLYEQFILQQG (SEQ ID NO:5, Pfizer); and CGEN-25017 (Compugen). Additional peptide inhibitors of Tie2 activation are described in U.S. Pat. No. 7,138,370.

Antibody inhibitors of Tie2 activation (and/or angiopoietin-2) include AMG-780 (Amgen), MEDI-3617 (MedImmune/AstraZeneca), DX-2240 (Dyax/Sanofi-Aventis), REGN-910 (Sanofi/Regeneron), RG7594 (Roche), LC06 (Roche), TAvi6 (Roche), AT-006 (Roche/Affitech). Additional Tie2 receptor binding antibody antagonists and antibody binding sequences therefrom are described in U.S. Pat. Nos. 7,521,053, 7,658,924, and 8,030,025, as well as U.S. Patent Application Publication Nos. 2013/0078248, 2013/0259859, and 2015/0197578.

Tie2 binding antagonists also include the small molecule inhibitors, CGI-1842 (CGI Pharmaceuticals), LP-590 (Locus Pharmaceuticals), ACTB-1003 (Act Biotech/Bayer AG), CEP-11981 (Cephalon/Teva), MGCD265 (Methylgene), Regorafenib (Bayer), Cabozantinib/XL-184/BMS-907351 (Exelixis), Foretnib (Exelixis), MGCD-265 (MethylGene Inc.).

Immune Checkpoint Regulators

The trispecific antibody includes a targeting domain to at least one immune checkpoint regulator. The immune checkpoint regulator may be an immune checkpoint antagonist or an immune checkpoint agonist. An immune checkpoint antagonist can provide a means for inhibiting signaling pathways that otherwise lead to T-cell activation, which is important for antitumor immunity. An immune checkpoint antagonist includes receptors and their associated ligands, which together provide a means for inhibiting signaling pathways that otherwise lead to T-cell activation. An immune checkpoint antagonist modulates or interferes with the activity of the immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced.

In contrast, an immune checkpoint agonist (of e.g., a costimulatory molecule) stimulates the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. Such immune checkpoint agonists or costimulatory molecules include cell surface molecules other than antigen receptors or their ligands that are required for an efficient immune response, and include, but are not limited to MHC class I molecules, TNF receptor proteins, immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In recent years, a number of immune checkpoint regulators in the form of receptors and their ligands have been identified. Immune checkpoint antagonists include, but are not limited to PD-1 and its ligands, PD-L1 and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; T cell Ig and ITIM domain (TIGIT) and its CD155 ligand; CD122 and its CD122R ligand; CD70, glucocorticoid-induced TNFR family-related protein (GITR), B7H3, B and T lymphocyte attenuator (BTLA); and VISTA (Le Mercier et al., Front. Immunol., (6), Article 418, 2015). In addition, a number of checkpoint regulator inhibitors have been identified and tested in various clinical and pre-clinical models and/or approved by the FDA (Kyi et al., FEBS Letters, 588:368-376 (2014). The concept of inhibitory receptor blockade, also known as immune checkpoint blockade, has been validated by virtue of e.g., the FDA approval of the PD-1 inhibitors, nivolumab and pembrolizumab, as well as the anti-CTLA-4 antibody, ipilimumab for metastatic melanoma.

In certain embodiments, the checkpoint regulator binding antagonist is an antibody or antibody fragment binding to PD-1, PD-L1 or PD-L2. Exemplary anti-PD-1 antibodies include, but are not limited to, nivolumab (BMS-936558, MDX-1106, OPDIVO™), a humanized immunoglobulin G4 (IgG4) mAb (Bristol-Myers Squibb); pembrolizumab (MK-3475, lambrolizumab, KEYTRUDA™) (Merck); pidilizumab (CT-011) (Medivation); and AMP-224 (Merck). Anti-PD1 antibodies are commercially available, for example from ABCAM (AB137132), BIOLEGEND™ (EH12.2H7, RMP1-14) and AFFYMETRIX EBIOSCIENCE (J105, J116, MIH4).

In some embodiments, the checkpoint regulator antagonist is nivolumab, a humanized anti-PD-1 IgG antibody. The nivolumab heavy chain has the following amino acid sequence:

(SEQ ID NO: 13)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVSVLTV

LHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYS

RLTVDKSRWQEGNVFSCSVMHEALHNHYTQKSLSLSLGK.

The underlined sequence identifies the nivolumab heavy chain variable region. In certain embodiments, the trispecific inhibitor may include the heavy chain variable region QVQLVESGGGVVQPGRSLRLDCK-ASGITFSNSGMHWVRQAPGKGLEWVAVIWYDGSK RYYADSVKGRFTISRDNSKNTLFLQMNSLRAED-TAVYYCATNDDYWGQGTLVTVSS (SEQ ID NO: 14) without the associated constant regions.

The nivolumab light chain has the following amino acid sequence:

(SEQ ID NO: 15)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The underlined sequence identifies the nivolumab light chain variable region. In certain embodiments, the trispecific inhibitor may include the light chain variable region EIVLTQSPATLSLSPGERATLSCRASQSVSSY-LAWYQQKPGQAPRLLIYDASNRATGIPA RFSGSGSGTDFTLTISSLEPED-FAVYYCQQSSNWPRTFGQGTKVEIK (SEQ ID NO: 16) without the associated constant region.

Exemplary anti-PD-L1 antibodies include atezolizumab (MPDL3280A, RG7446), a fully human IgG4 mAb Genentech/Roche); BMS-936559 (MDX-1105), a fully humanized IgG4 mAb (Bristol-Myers Squibb); MEDI4736, a humanized IgG antibody (Medimmune/AstraZeneca); and MSB0010718C, a fully human IgG4 monoclonal antibody (Merck, EMD Serono).

In some embodiments, the checkpoint regulator antagonist is atezolizumab having a heavy chain amino acid sequence of:

(SEQ ID NO: 17)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

-continued
WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK.

The underlined sequence identifies the atezolizumab heavy chain variable region. In certain embodiments, the trispecific inhibitor may include the heavy chain variable region DKTHCPPCPAPELLGGPSVFLFPPKPKDTLMISRTPE-VTCVVVDVSHEDPEVKFNWYV DGVEVHNAKTKPRE-EQYASTYRVVSVLTVLHQDWLNGKEYKCKVSNKA-LPAPIEKTIS KAKGQPREPQVYTLPPSREEMT-KNQVSLTCLVKGFYPSDIAVEWESNGQPENNYKTTPP VLDSDGSFFLYSK-LTVDKSRWQQGNVFSCSVMHEALHNHYTQKSLSL-SPGK (SEQ ID NO:18) without the associated constant regions.

The atezolizumab light chain has the following amino acid sequence:

(SEQ ID NO: 18)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The underlined sequence identifies the nivolumab light chain variable region. In certain embodiments, the trispecific inhibitor may include the light chain variable region (SEQ ID NO: 19)
DIQMTQSPSSLSASVGDRVTITCRASQDVSTAVAWYQQKPGKAPKLLIY
SASFLYSGVPSRFSGSGSGTDFTLTISSLQPEDFATYYCQQYLYHPATF
GQGTKVEIK without the associated constant region.

In other embodiments, the trispecific antibody or immune checkpoint regulator binding antagonist includes $V_L$ and/or $V_H$ chain regions from anti-CTLA-4 antibodies. Exemplary anti-CTLA-4 antibodies include ipilimumab, trevilizumab and tremelimumab.

In certain embodiments, the immune checkpoint regulator binding antagonist is a dominant negative protein of the immune checkpoint regulator. In particular embodiments, the dominant negative protein comprises an extracellular domain derived from a member selected from the group consisting of PD-L1, PD-L2, PD-1, B7-1, B7-2, B7H3, CTLA-4, LAG-3, TIM-3, TIGIT, GITR, BTLA, VISTA, CD70, and combinations thereof. In certain particular embodiments, these extracellular domains are fused to an immunoglobulin constant region or Fc receptor in the presently described antibodies.

Such mutants can bind to the endogenous receptor so as to form a complex that is deficient in signaling. In certain embodiments, the extracellular domain is fused to an immunoglobulin constant region or Fc fragment or to a monomer in the oligomeric protein complex. In certain preferred embodiments, a dominant negative PD-L1 antagonist comprises the extracellular domain of PD-L1, PD-L2, or PD-1. In another embodiment, a dominant-negative PD-1 antagonist is employed, which has a mutation so that it is no longer able to bind PD-L1. An exemplary dominant negative protein is AMP-224 (co-developed by Glaxo Smith Kline and Amplimmune), a recombinant fusion protein comprising the extracellular domain of PD-L2 and the Fc region of human IgG.

Exemplary anti-CTLA-4 dominant negative proteins include the humanized fusion protein, Abatacept (Orencia), which comprises the Fc region of IgG1 fused to the CTLA-4 ECD, and Belatacept (NULOJIX®), a second generation higher-affinity CTLA-4-Ig variant with two amino acid substitutions in the CTLA-4 ECD relative to Abatacept.

Exemplary immune checkpoint regulator agonists include, but are not limited to members of the tumor necrosis factor (TNF) receptor superfamily, such as CD27, CD40, OX40, GITR and 4-IBB (CD137) and their ligands, or members of the B7-CD28 superfamily, including CD28 and ICOS (CD278). Additional checkpoint regulator agonists include CD2, CDS, ICAM-1, LFA-1 (CD11a/CD18), CD30, BAFFR, HVEM, CD7, LIGHT, NKG2C, SLAMF7, NKp80, CD160, B7-H3, CD83 ligand, as well as those described above. Immune checkpoint agonists can include antibodies or soluble fusion protein agonists comprising one or more costimulatory domains. Agonist antibodies include, but are not limited to anti-CD40 mAbs, such as CP-870,893, lucatumumab, and dacetuzumab; anti-CD137 mAbs, such as BMS-663513 urelumab, and PF-05082566; anti-OX40 mAbs; anti-GITR mAbs, such as TRX518; anti-CD27 mAbs, such as CDX-1127; and anti-ICOS mAbs.

Exemplary GITR agonists include, e.g., GITR fusion proteins and anti-GITR antibodies (e.g., bivalent anti-GITR antibodies) such as, e.g., a GITR fusion protein described in U.S. Pat. Nos. 6,111,090 and 8,586,023; European Patent No.: 090505B1, PCT Publication Nos.: WO 2010/003118 and WO 2011/090754. Anti-GITR antibodies are described in, e.g., in U.S. Pat. Nos. 7,025,962, 7,618,632, 7,812,135, 8,388,967, and 8,591,886; European Patent Nos.: 1947183B1 and 1866339; PCT Publication Nos.: WO 2011/028683, WO 2013/039954, WO2005/007190, WO 2007/133822, WO2005/055808, WO 99/40196, WO 2001/03720, WO99/20758, WO2006/083289, WO 2005/115451, WO 2011/051726. An exemplary anti-GITR antibody is TRX518.

Oligomeric Protein Scaffold

In some embodiments, the binding antagonists and/or agonists in the trispecific antibody are configured as single or double chain polypeptide arms covalently joined to an oligomeric protein scaffold and projecting therefrom. The polypeptide arms may project from the amino terminal end of the scaffold, the carboxy terminal end of the scaffold, or both. A polypeptide arm may comprise one polypeptide chain or two polypeptide chain associated with one another. In each arm, one polypeptide chain is covalently linked to a monomer of the oligomeric protein scaffold. Alternatively, one or more of the binding antagonists in the trispecific antibody may be configured two pairs of single chain polypeptide arms projecting from the amino- and carboxy terminal ends of the oligomeric protein scaffold.

In one embodiment, two of the binding specificities are conferred by antibody variable regions and the third binding specificity is conferred by one or more inhibitory peptides. In an exemplary embodiment depicted in FIG. 1A, the binding specificities of the VEGF binding antagonists and the immune checkpoint regulator binding antagonists are conferred by antibody variable regions, while the binding specificity of the Tie2 receptor antagonist is conferred by an inhibitory peptide, such as the trebanabin peptide (TBN-P). In a particular embodiment, the inhibitory Tie2 receptor peptide, more specifically, the TBN-P peptide comprises the amino acid sequence of SEQ ID NO:1. In certain preferred embodiments, the inhibitory Tie2 receptor peptide is fused to the C-terminal end of an Fc fragment. The amino acid sequence of an exemplary inhibitory Ang2-IgG1 Fc fusion protein is set forth in SEQ ID NO:2.

Figure 7A:
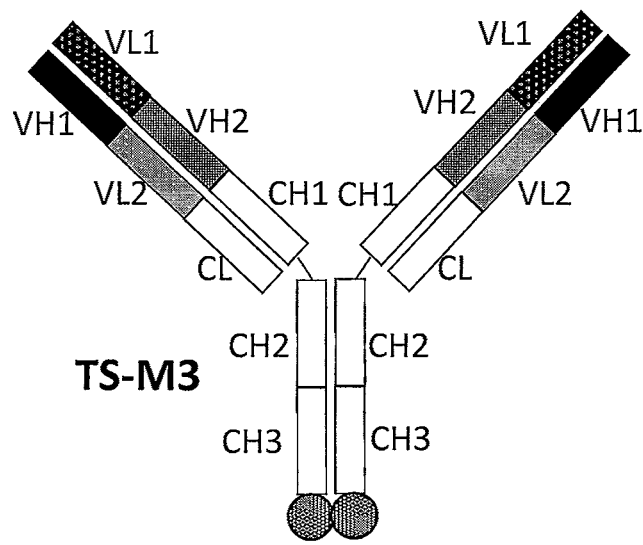
FIGS. 7A and 7B depict the structural configurations of two exemplary trispecific antibody embodiments, TS-M3 (FIG. 7A) and TS-M4 (FIG. 7B), each comprising a homodimeric scaffold in accordance with certain aspects of the present disclosure. Each of these two configurations includes a pair of TBN peptides fused to the C-terminal end of the two heavy chains, along with a pair of anti-PD1 determinants and a pair of anti-VEGF determinants in the two arms.
Figure 7B:
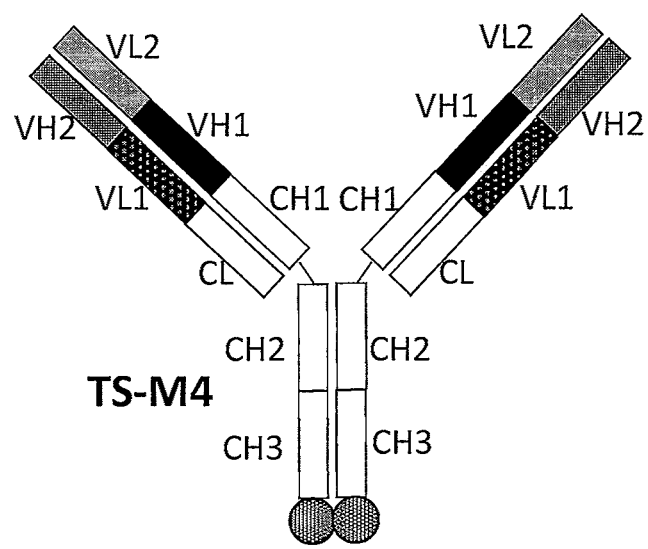
Figure 7C:
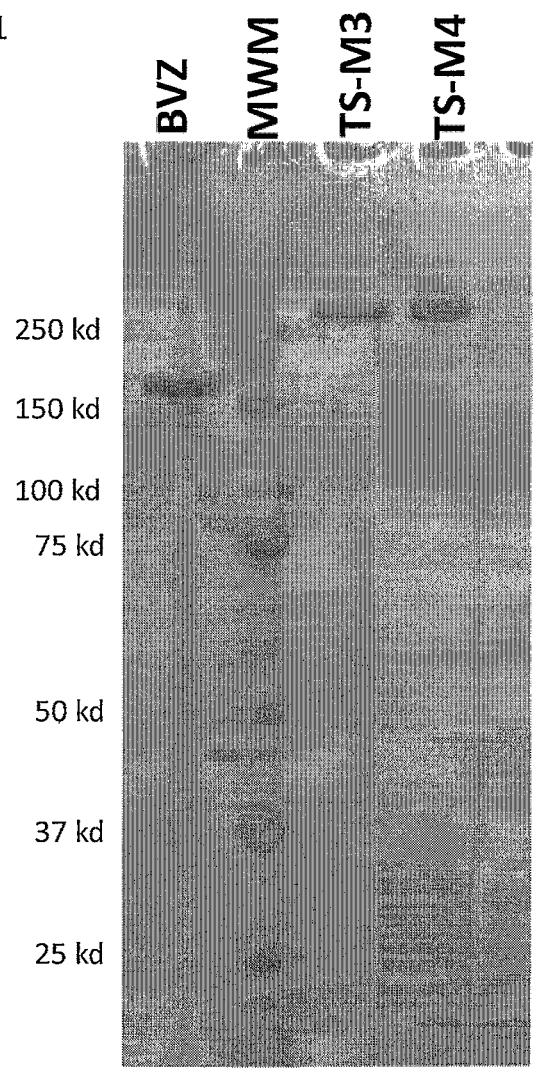
FIG. 7C shows a PAGE gel of recombinant BVZ control mAb, TS-M3, TS-M4 and the MWM. The amino acid sequences of the heavy chain and light chain of TS-M3 are shown in SEQ ID NOS:24 and 25, respectively. The amino acid sequences of the heavy chain and light chain of TS-M4 are shown in SEQ ID NOS:26 and 27, respectively.

In one embodiment depicted in FIG. 1A, the trispecific antibody comprises a homodimeric protein scaffold containing one or more immunoglobulin constant regions (e.g., CH2-CH3) forming a homodimer with two double chain arms projecting from the amino terminal side of the homodimeric scaffold. One chain covalently links a CH1 domain to the CH2 domain in the dimeric scaffold by via hinge region. In certain particular embodiments depicted in FIGS. 7A (TS-M3) and 7B (TS-M4), each arm comprises immunoglobulin variable regions conferring binding to PD-1 (VH1:VL1) and VEGF-A (VH2:VL2). Inhibitory peptides corresponding to the third binding specificity (represented by circles) are covalently linked at the carboxy terminal end of each monomer in the homodimeric scaffold.

Figure 1B:
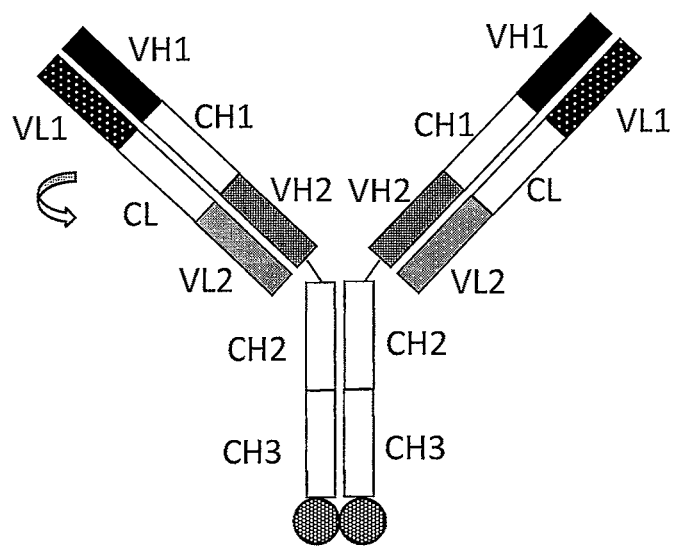

In an alternative embodiment depicted in FIG. 1B, the CH1 domain is positioned between the two binding specificities. In certain particular embodiments depicted in FIGS. 8A (TS-M5) and 8B (TS-M6), each arm comprises immunoglobulin variable regions conferring binding to PD-1 (VH1:VL1) and VEGF-A (VH2:VL2).

Figure 1C:
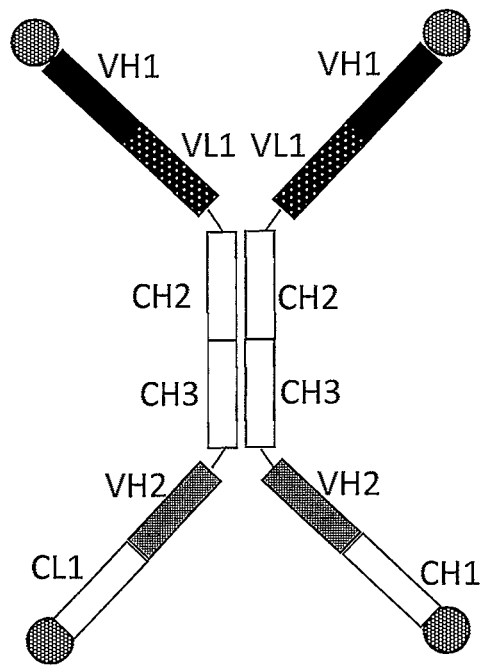
Figure 1D:
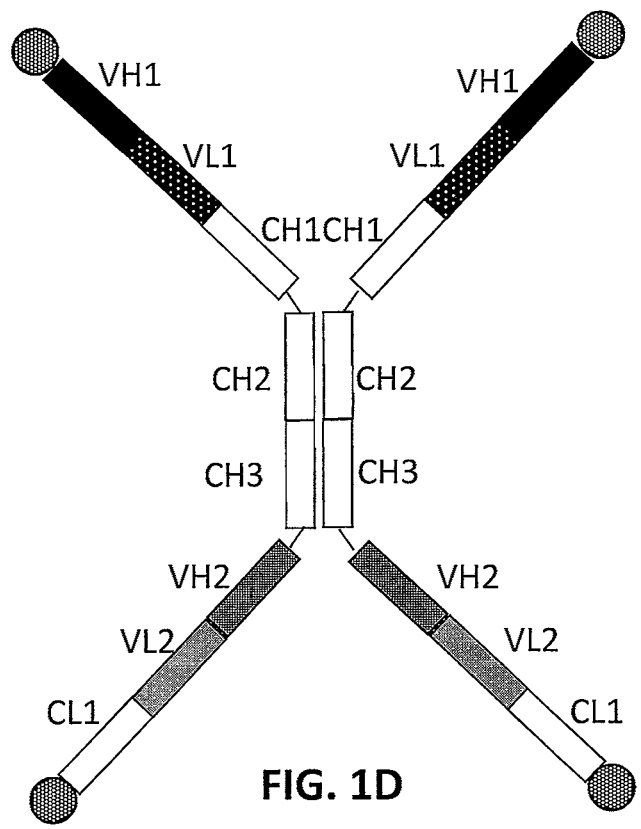

In another embodiment shown in FIG. 1C, the trispecific antibody comprises a homodimeric protein scaffold of immunoglobulin constant regions (e.g., CH2-CH3) with two pairs of single chain arms, each pair projecting from an opposite end of the dimeric protein scaffold. A first pair of arms projects from the amino terminal end of the dimeric scaffold and a second pair of arms projects from the carboxy terminal end of the dimeric protein scaffold. Each arm in the first pair is an anti-VEGF-A scFv, while each arm in the second pair is an anti-PD-L1 scFv. In addition, inhibitory TBN-P peptides (represented as circles) are covalently linked at the N-terminal ends in each of the first pair of arms and at the C-terminal ends in each of the second pair of arms.

Figure 9A:
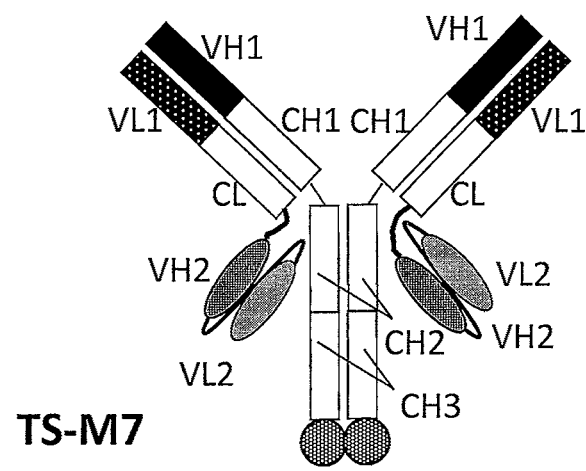
FIGS. 9A and 9B depict the structural configurations of two exemplary trispecific antibody embodiments, TS-M7 (FIG. 9A) and TS-M8 (FIG. 9B), each comprising a homodimeric scaffold in accordance with certain aspects of the present disclosure. Each of these two configurations includes a pair of scFvs directed against PD-1 or VEGF, which are fused to the C-terminal end of the two light chains and a pair of TBN peptides fused to the C-terminal end of the two heavy chains. The amino acid sequences of the heavy chain and light chain of TS-M7 are shown in SEQ ID NOS:32 and 33, respectively. The amino acid sequences of the heavy chain and light chain of TS-M8 are shown in SEQ ID NOS:34 and 35, respectively.
Figure 9B:
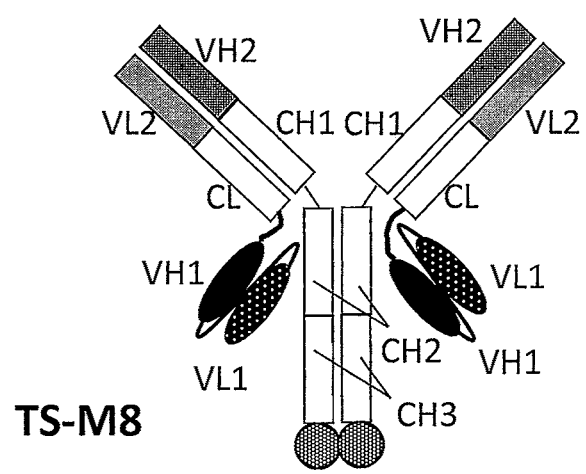

The inhibitory Ang-2 peptide or TBN-P peptide may be fused to the C-terminal end of the Fc fragment, such as an IgG1 Fc fragment (e.g., as SEQ ID NO:2) or it may be terminally fused to one or more single chain arms projecting from a homodimeric or heterodimeric protein scaffold. Alternatively, the inhibitory Ang-2 peptide may be fused to the C-terminal end of an Fc fragment, such as the IgG1 Fc fragment, while one or two scFv fragments are fused to the C-terminal end(s) of the light chain(s) in the trispecific antibody or inhibitor as shown, for example in FIGS. 9A (TS-M7) and 9B (TS-M8).

In other embodiments, natively, the inhibitory peptide may be fused to the C-terminal end in one or both of the antibody light chains as shown, for example, in FIGS. 10A and 10B, while the one or two scFv fragments are fused to the C-terminal end(s) of the heavy chain(s) in the trispecific antibody or inhibitor as shown, for example in FIGS. 10A (TS-M9) and 10B (TS-M10).

In certain preferred embodiments exemplified in FIGS. 1-4 and 6-11, the trispecific antibody comprises an anti-VEGF binding specificity comprising an antigen binding site from e.g., humanized monoclonal antibody bevacizumab; an anti-PD-1 binding specificity comprising an antigen binding site from an anti-PD-1 antibody (e.g., Nivolumab); and an inhibitory angiopoietin-2 (Ang-2) peptide (e.g., SEQ ID NO:1).

One of the challenges for efficiently producing bispecific and trispecific antibody preparations concerns mispairing of heavy and light chains when co-expressing chains of different binding specificities. Table 1 lists several amino acid substitution options for overcoming mispairing between heavy chains of different binding specificities, which "enforce" or preferentially promote correct association between desired heavy chains. Any approach to prevent or reduce mispairing between heavy chains may be used to make the trispecific antibodies according to the present disclosure.

The "knobs-into-holes" (KiH) approach relies on modifications of the interface between the two CH3 domains where most interactions occur. Typically, a bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges.

An alternative approach is based on charged residues with ionic interactions or steric complementarity. This includes altering the charge polarity in the CH3 interface so that co-expression of electrostatically matched Fc domains support favorable attractive interactions and heterodimer formation while retaining the hydrophobic core, whereas unfavorable repulsive charge interactions suppress homodimerization. See Table 1. The amino acid numbering in Table 1 follows the Kabat numbering scheme and can be applied to heavy chain amino acid sequences of the antibodies described herein.

In a further approach, leucine zipper (LZ) domains may be incorporated into a protein scaffold. A leucine zipper is a common three-dimensional structural motif in proteins, typically as part of a DNA-binding domain in various transcription factors. A single LZ typically contains 4-5 leucine residues at approximately 7-residue intervals, which forms an amphipathic alpha helix with a hydrophobic region running along one side. In a particular embodiment, a heterodimeric protein scaffold comprises a LZ from the c-jun transcription factor associated with a LZ from the c-fos transcription factor. Although c-jun is known to form jun-jun homodimers and c-fos does not form homodimers, the formation of jun-fos heterodimers is greatly favored over jun-jun homodimers.

A leucine zipper domain may be incorporated in place of CH2-CH3 sequences in the protein scaffold or it may be placed at the carboxy terminal end of the two heavy chains in the trispecific antibody. In the case of the latter, a furin cleavage site may be introduced between the carboxy terminal end of CH3 and the amino terminal end of the leucine zipper. This can facilitate furin-mediated cleavage of the leucine zipper following the heterodimerization step when co-expressing the heavy and light chains of the trispecific antibody in an appropriate mammalian cell expression system (see Wranik et al., *J. Biol. Chem.*, 287(5):43331-43339, 2012).

TABLE 1

| Type | HC1 | HC2 |
| --- | --- | --- |
| Knobs-into-holes | Y349C, T366S, L368A, Y407V | S354C, T366W |
| Ionic, electrostatic | S183E, E356K, E357K, D399K | S183K, K370E, K409D, K439E |
| Ionic, electrostatic | K392D, K409D | E356K, D399K |
| HA-TF substitutions | S364H, F405A | Y349T, T394F |
| HF-TA substitutions | S364H, T394F | Y349T, F405A |
| Leucine zipper heterodimer | human c-Jun leucine zipper | human c-fos leucine zipper |

The amino acid numbering in Table 1 follows the Kabat numbering scheme and can be applied to heavy chain amino acid sequences of the antibodies described herein. The mutations described in Table 1 may be applied to the sequence (published or otherwise) of any immunoglobulin IgG1 heavy chain, as well as other immunoglobulin classes, and subclasses (or isotypes) therein.

When co-expressing heavy and light chains of bispecific or trispecific antibodies, the light chains of one binding specificity can also mispair with heavy chains of a different binding specificity. Therefore, in certain embodiments, portions of the heavy chain, light chain or both may be modified relative to the "wild-type" antibody chains from which they are derived to prevent or reduce mispairing of both heavy chain constant regions to one another, as well mispairing of light chain constant regions to their heavy chain counterparts.

The light chain mispairing problem can be addressed in several ways. In some embodiments, sterically complementary mutations and/or disulfide bridges may be incorporated into the two VL/VH interfaces. In other embodiments, mutations can be incorporated based on ionic or electrostatic interactions. In some embodiments, light chain mispairing may be prevented or reduced by employing a first arm with an S183E mutation in the CH1 domain of the heavy chain and an S176K mutation in the CL domain of the light chain. A second arm may include an S183K mutation in the in the CH1 domain of the heavy chain and an S176E mutation in the CL domain of the light chain. In other embodiments, a "CrossMab" approach is employed, where one arm in the trispecific antibody (e.g., Fab) is left untouched, but in the other arm containing the other binding specificity, one or more domains in the light chain are swapped with one or more domains in the heavy chain at the heavy chain:light chain interface as further described below.

Figure 11A:
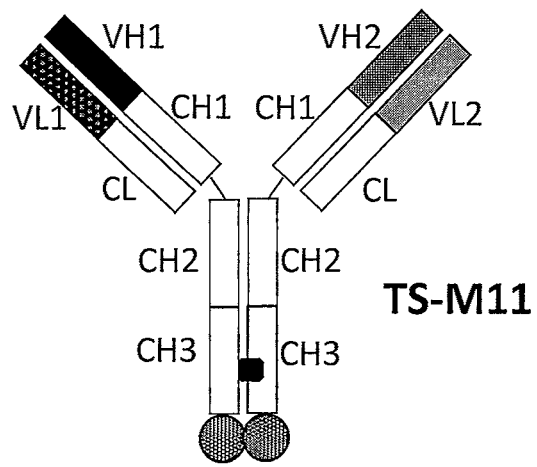
FIGS. 11A and 11B depicts the structural configurations of two exemplary trispecific antibody embodiments, TS-M11 (FIG. 11A) and TS-M12 (FIG. 11B), each comprising a heterodimeric scaffold in accordance with certain aspects of the present disclosure. Each of these two configurations includes a pair of TBN peptides fused to the C-terminal end of the two heavy chains, along with anti-PD1 determinants in one arm and anti-VEGF determinants in the other arm. As indicated, TS-M11 has a "knob-in-hole" design (FIG. 11A). As indicated by the stars in FIG. 11B, TS-M12 has mutations in the light and heavy chains to reduce improper mispairing of the heavy and light chains following their synthesis in cells as further described herein.

In certain embodiments, two arms project from a heterodimeric protein scaffold in which a first arm comprises a first Fab fragment comprising the first binding specificity and the second arm comprises a second Fab fragment comprising the second specificity. FIGS. 2-4 and 11B depict exemplary embodiments comprising a heterodimeric protein scaffold in which the stars designate mutations in immunoglobulin constant regions that prevent mispairing of light or heavy chains from one binding specificity with light or heavy chains from another binding specificity. Similarly, FIG. 11A shows an exemplary embodiment comprising a heterodimeric protein scaffold depicting a knob in the CH3 domain to prevent or reduce mispairing of heavy chains from one another during antibody synthesis. The stars in FIG. 11B further designate mutations in immunoglobulin constant regions that prevent or reduce mispairing of light chains from one another during antibody synthesis. Methods, immunoglobulin domain sequences, including specific mutations for preventing mispairing of heavy and light chains are disclosed in U.S. Patent Application Publication Nos. 2014/0243505, 2013/0022601.

In one embodiment, two double chain arms project from a heterodimeric protein scaffold in which a first arm comprises a first Fab fragment comprising the first binding specificity and the second arm comprises a second Fab fragment comprising the second specificity. In one embodiment, the heterodimeric protein scaffold in which one more mutations are included in each of the two polypeptide to prevent mispairing of heavy chains from one binding specificity to heavy chains of a different binding specificity when coexpressing the polypeptide chains of the trispecific antibody.

In some embodiments, each of the two double chain arms projecting from the heterodimeric protein scaffold further includes one more mutations in the constant regions in each of the first and second Fab fragments (e.g., CH1 and/or CL) so as to prevent mispairing of light chains from one binding specificity (e.g., VL1) to light chains of a different binding specificity (e.g., VL2) when coexpressing the polypeptide light chains of the trispecific antibody in cultured cells.

Figure 2A:
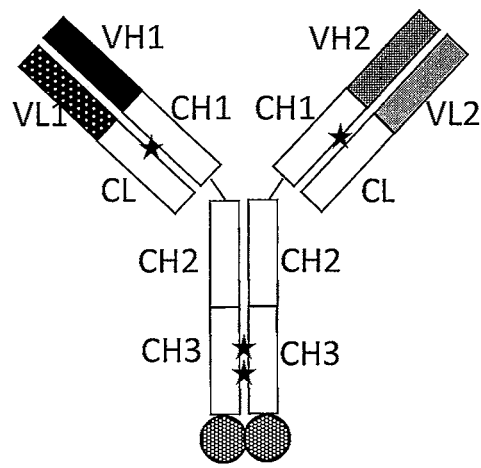
FIGS. 2A-2C depict various trispecific antibody embodiments comprising a heterodimer scaffold in accordance with other aspects of the present disclosure.

In one embodiment depicted in FIG. 2A, the heterodimeric protein scaffold comprises a modified CH2-CH3 heterodimer comprising several mutations in the CH3 domains to prevent or reduce mispairing between heavy chains. In this embodiment, each of the two Fab arms includes one more mutations in the constant regions in each of the first and second Fab fragments (e.g., CH1 and/or CL) so as to prevent mispairing of light chains from one binding specificity (e.g., VL1) to light chains of a different binding specificity (e.g., VL2) when coexpressing the polypeptide light chains in the trispecific antibody. In a particular embodiment exemplified in FIG. 2A, one arm contains an S183E mutation in the CH1 domain of the heavy chain, E356K and D399K mutations in the CH3 domain of the heavy chain, and an S176K mutation in the constant region of the light chain (CL). The second arm contains an S183K mutation in the CH1 domain of the heavy chain, K392D and K409D mutations in the CH3 domain of the heavy chain, and an S176E mutation in the constant region of the light chain.

Another way to address the light chain mispairing problem is to employ a pair of scFv arms extending from the heterodimeric protein scaffold, including a first scFv arm comprising containing VH1 and VL1 domains that constitute the first binding specificity and a second scFv arm containing VH2 and VL2 domains that constitute the second binding specificity. Alternatively, the trispecific antibody may contain two single chain arms projecting from a heterodimeric protein scaffold, including a first arm comprising a single polypeptide chain comprising a VH1 domain from the first binding specificity fused to a VL2 domain from the second binding specificity and the second arm comprising a single polypeptide chain comprising a VH2 domain from the second binding specificity fused to a VL1 domain from the first binding specificity.

Figure 2B:
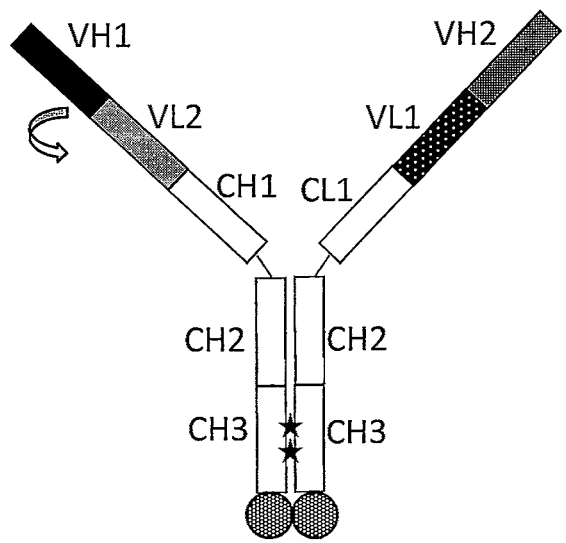
Figure 2C:
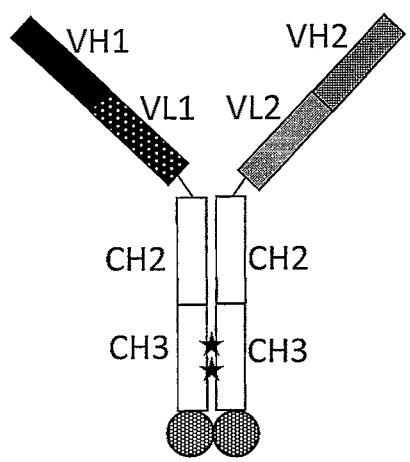

Exemplifying these embodiments, FIGS. 2B and 2C depict a pair of scFv arms extending from a CH2-CH3 protein scaffold. In FIG. 2B, the left arm contains a heavy chain variable domain corresponding to a first antigen binding specificity (VH1), followed by a light chain variable domain corresponding to a second antigen binding specificity (VL2), which is followed by CH1 domain. The right arm contains a heavy chain variable domain corresponding to a second antigen binding specificity (VH2), followed by a light chain variable domain corresponding to a second antigen binding specificity (VL1), which is followed a CL1 domain. In FIG. 2C, the left arm is a first scFv with a first binding specificity and the right arm is a second scFv with a second binding specificity. In contrast to the FIG. 2B, the variable regions from the two binding specificities are not swapped. In each of FIGS. 2A-2C, inhibitory peptides corresponding to the third binding specificity (represented by circles) are covalently linked at the carboxy terminal end of each monomer in the heterodimeric scaffold.

In other embodiments, an alternative "CrossMab" approach to prevent mispairing of light chains involves preparing a trispecific antibody with two double chain arms projecting from the heterodimeric protein scaffold, where the first arm comprises a first Fab fragment comprising the first binding specificity and the second arm comprises a modified Fab fragment comprising the second specificity. In this case, the first Fab arm is left untouched, while the other Fab arm (on the right) with the other binding specificity is modified with respect to e.g., FIG. 2A by swapping one or more domains in the light chain with one or more domains in the heavy chain at the heavy:light chain interface.

Figure 3A:
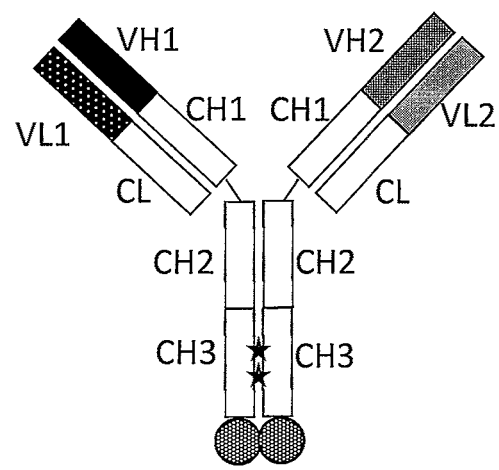
FIGS. 3A-3C depicts various trispecific antibody embodiments comprising a heterodimer scaffold in accordance with another aspect of the present disclosure.
Figure 3B:
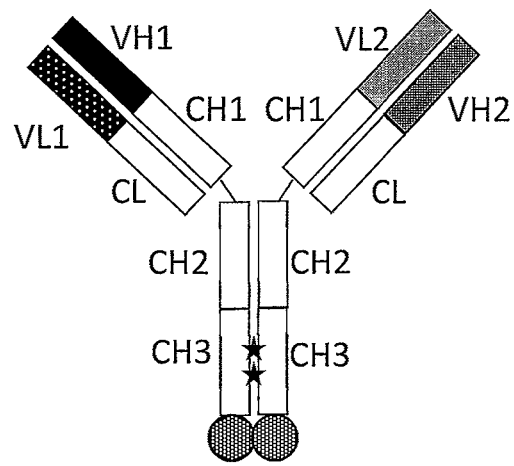
Figure 3C:
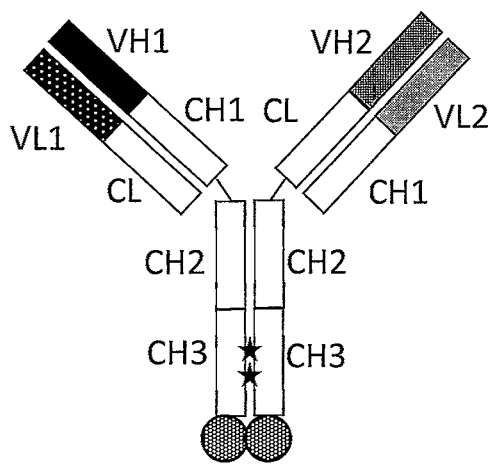
Figure 11B:
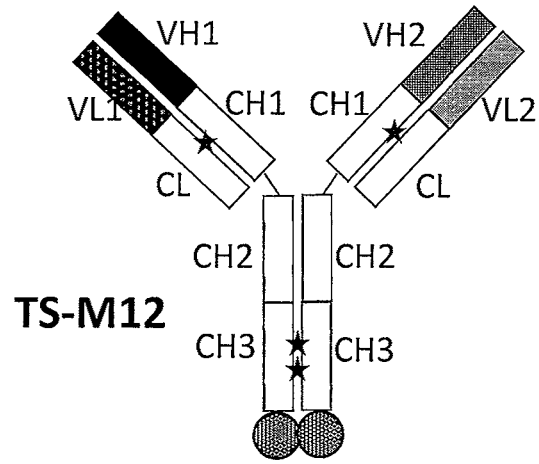
Figure 11C:
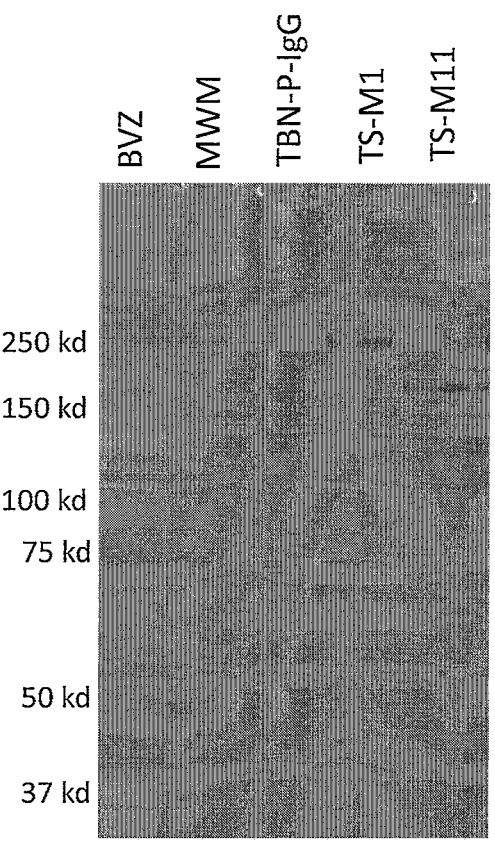
FIG. 11C shows a PAGE gel of recombinant BVZ control mAb, trebanabin (TBN-P-IgG), TS-M1, TS-M11, and the MWM. The amino acid sequences of the heavy chains of TS-M11 are shown in SEQ ID NOS:40 and 41, respectively. The amino acid sequences of the light chains of TS-M11 are shown in SEQ ID NOS:42 and 43, respectively. The amino acid sequences of the heavy chains of TS-M12 are shown in SEQ ID NOS:44 and 45, respectively. The amino acid sequences of the light chains of TS-M12 are shown in SEQ ID NOS:46 and 47, respectively.
Figure 13:
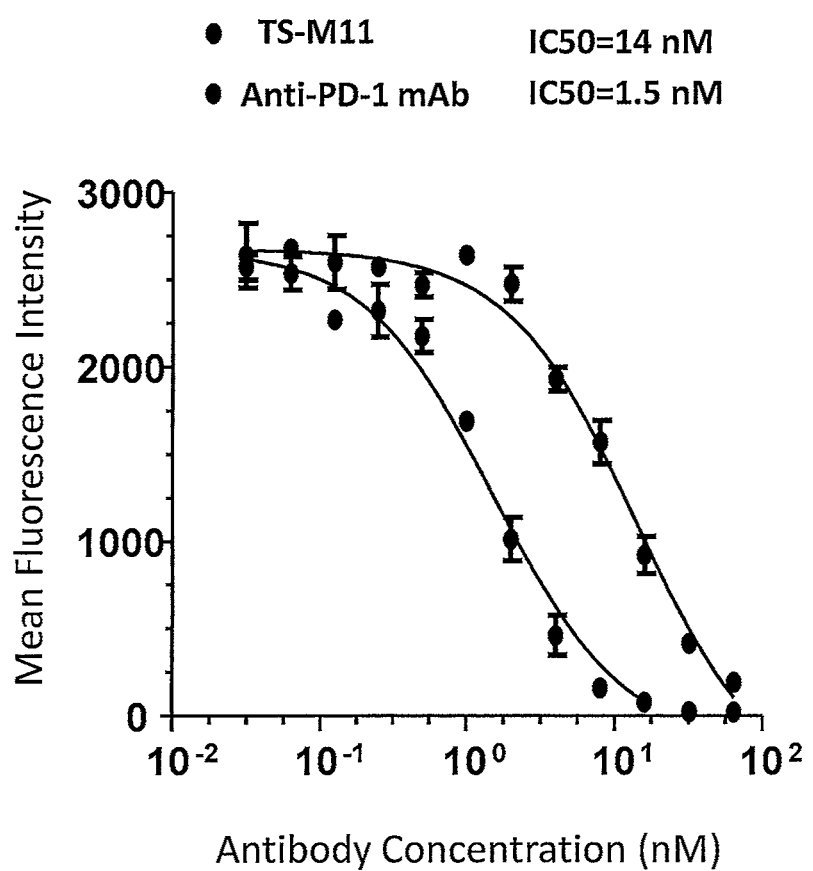
FIG. 13 depicts the ability of TS-M11 and the monospecific anti-PD-1 control to block PD-1/PD-L1 interactions. Half-maximal inhibitory concentrations ($IC_{50}$) were determined as described in FIGS. 12A-12G.

FIGS. 3A-3C and 11B exemplify the "CrossMab" approach. In this case, the modified Fab arm contains VH2, VL2, CH1 and CL domains. Whereas the first (or left) Fab arm is covalently linked to the left chain of the CH2-CH3 scaffold and contains a VH1-CH1 peptide associated with a VL1-CL peptide (as in FIG. 2A), the polypeptide chain of the second (or right) Fab arm covalently linked to the right chain of the CH2-CH3 scaffold comprises either (1) a VL2-CL region associated with a VH2-CH1 region light chain (FIGS. 3A, 11B); (2) a VL2-CH1 region associated with a VH2-CL region light chain (FIG. 3B); or (3) a VH2-CL region associated with a VL2-CH1 region light chain (FIG. 3C). Inhibitory peptides corresponding to the third binding specificity (represented by circles) are covalently linked at the carboxy terminal end in each monomer in the heterodimeric scaffold.

In further embodiments, the trispecific antibody contains four single chain arms projecting from a heterodimeric protein scaffold, including a first pair of arms projecting from the amino terminal end of the heterodimeric scaffold and a second pair of arms projecting from the carboxy terminal end of the heterodimeric protein scaffold. In this case, each arm is a single polypeptide chain covalently linked to a single polypeptide chain in the heterodimeric scaffold on either the amino terminal side or the carboxy terminal side.

Figure 4A:
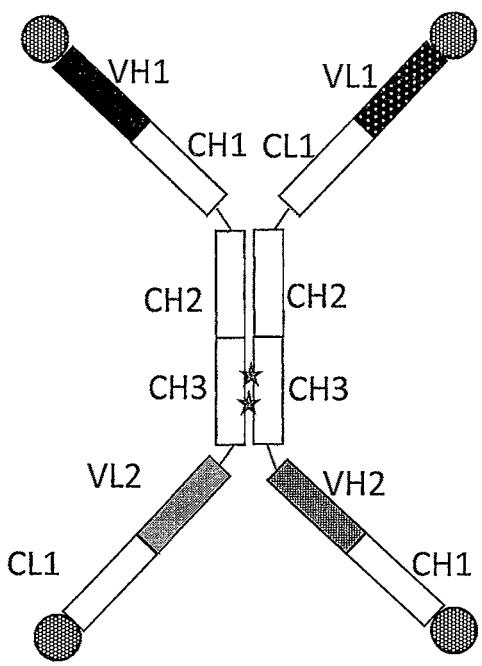
FIGS. 4A-4B depicts various trispecific antibody embodiments comprising a heterodimer scaffold in accordance with other aspects of the present disclosure.

In one embodiment exemplified in FIG. 4A, pairs of single chain arms are present on both sides of the heterodimeric CH2-CH3 scaffold. In this case, a first pair of arms includes a first (or left) arm containing a VH1 domain fused to a CH1 domain and a second (or right) arm containing a VL1 domain fused to a CL1 domain. Together, this first pair of arms constitutes the first binding specificity. The second pair of arms forms the second binding specificity and includes a third arm containing a VH2 domain fused to CH1 domain and a fourth arm containing a VL2 domain fused to a CL1 domain. As further shown in FIG. 4A, inhibitory peptides corresponding to the third binding specificity (represented as circles) are fused to the amino terminal ends of the first pair of arms and to the carboxy terminal ends the second pair of arms.

Figure 4B:
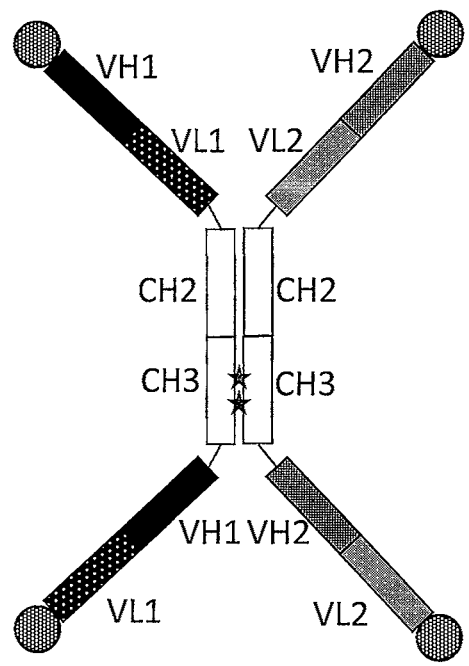
Figure 5A:
FIGS. 5A-5C depict exemplary binding elements for inclusion in the trispecific antibody embodiments described in the present disclosure.
Figure 5B:
Figure 5C:
Figure 6A:
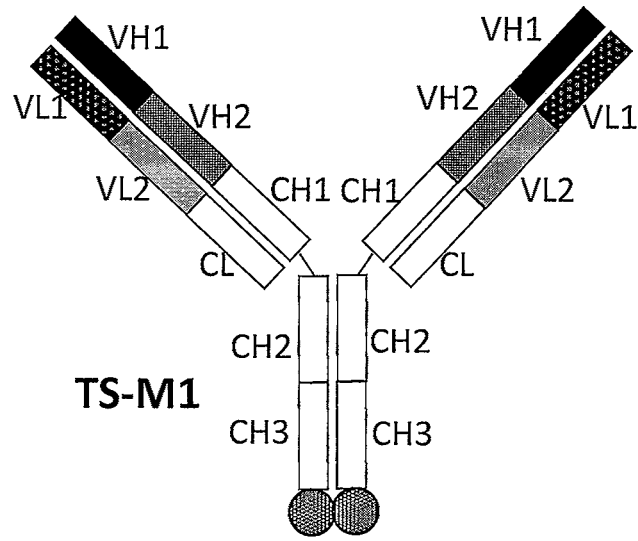
FIGS. 6A and 6B depict the structural configurations of two exemplary trispecific antibody embodiments, TS-M1 (FIG. 6A) and TS-M2 (FIG. 6B), each comprising a homodimeric scaffold in accordance with certain aspects of the present disclosure. Each of these two configurations includes a pair of trebanabin (TBN) peptides fused to the C-terminal end of the two heavy chains, along with a pair of anti-PD1 determinants and a pair of anti-VEGF determinants in the two arms.
Figure 6B:
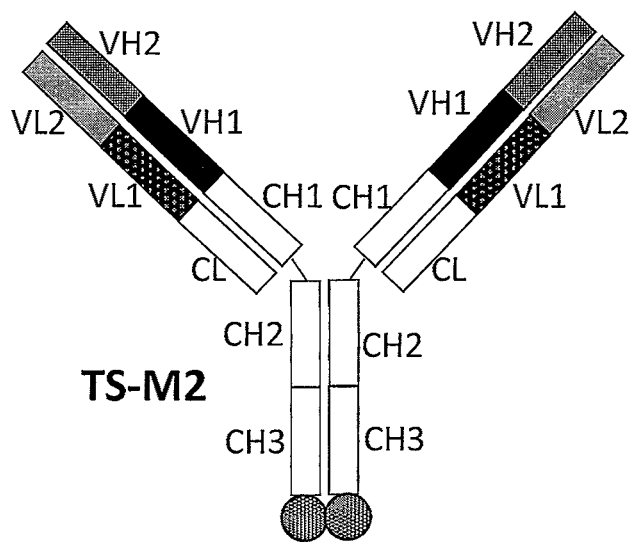
Figure 6C:
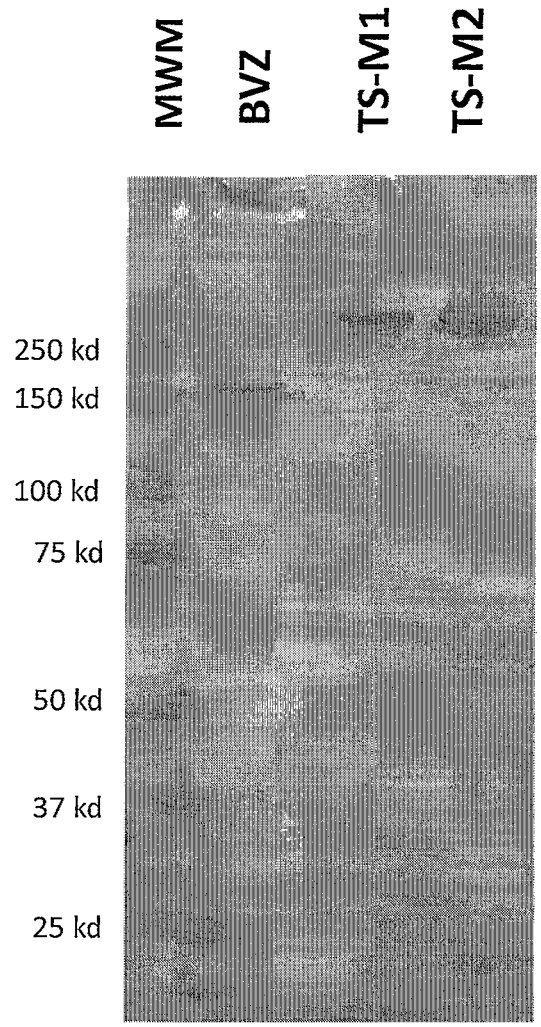
FIG. 6C shows a PAGE gel of recombinant bevacizumab (BVZ) control mAb, TS-M1, TS-M2, and the molecular weight markers (MWM). The amino acid sequences of the heavy chain and light chain of TS-M1 are shown in SEQ ID NO:20 and 21, respectively. The amino acid sequences of the heavy chain and light chain of TS-M2 are shown in SEQ ID NOS:22 and 23, respectively.

In another embodiment depicted in FIG. 4B, pairs of single chain arms are present on both sides of the heterodimeric CH2-CH3 scaffold, including a first pair of arms on the amino terminal side of the heterodimeric scaffold and a second pair of arms on the carboxy terminal side of the heterodimeric scaffold. The first pair of arms includes a first (or left) scFv arm corresponding to a first binding specificity and a second (or right) scFv arm corresponding to a second binding specificity. The second pair of arms on the carboxy terminal side of the heterodimeric scaffold includes a third (or left) scFv arm corresponding to the first binding specificity and a fourth (or right) scFv corresponding to the second binding specificity. As in FIG. 4A, inhibitory peptides corresponding to the third binding specificity (represented as circles) are fused to the amino terminal ends of the first pair of arms and to the carboxy terminal ends the second pair of arms. Of course, any isomeric arrangement of the four arm embodiments described herein is contemplated.

In certain embodiments, bispecific or trispecific antibodies are chemically conjugated to one or more peptides and/or small molecule drugs. The peptides or small molecule drug can be the same or different. The peptides or small molecule drugs can be attached, for example to reduced SH groups and/or to carbohydrate side chains. Methods for making covalent or non-covalent conjugates of peptides or small molecule drugs with antibodies are known in the art and any such known method may be utilized.

In some embodiments the peptide or small molecule drug is attached to the hinge region of a reduced antibody component via disulfide bond formation. Alternatively, such agents can be attached using a heterobifunctional cross-linkers, such as N-succinyl 3-(2-pyridyldithio)propionate (SPDP). General techniques for such conjugation are well-known in the art. In some embodiments, the peptide or small molecule drug is conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent. Methods for conjugating peptide inhibitors or small molecule drugs to antibodies via antibody carbohydrate moieties is well-known to those of skill in the art. For example, in one embodiment, the method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate. Exemplary methods for conjugating small molecule drugs and peptides to antibodies are described in U.S. Patent Application Publication No. 2014/0356385.

Preferably, the trispecific antibodies in the present disclosure retain certain desirable characteristics and pharmacokinetic properties of antibodies, including a desirable in vitro and in vivo stability (e.g., lone half-life and shelf-life stability), efficient delivery into desired target cells, increased affinity for binding partners, desirable antibody-dependent cell-mediated cytotoxicity and complement-dependent cytotoxicity, and reduced renal clearance or excretion. Accordingly, careful attention to size and need for particular constant region effector functions may be considered in the design of the trispecific antibodies.

The trispecific antibodies may range in size from 50 kD to 300 kD, from 50 kD to 250 kD, from 60 kD to 250 kD, from 80 kDa to 250 kD, from 100 kD to 250 kD, from 125 kD to 250 kD, from 150 kD to 250 kD, from 60 kD to 225 kD, from 75 kD to 225 kD, from 100 kD to 225 kD, from 125 kD to 225 kD, from 150 kD to 225 kD, from 60 kD to 200 kD, from 75 kD to 200 kD, from 100 kD to 125 kD to 200 kD, from 150 kD to 200 kD, from 60 kD to 150 kD, from 75 kD to 150 kD, from 100 kD to 150 kD, from 60 kD to 125 kD, from 75 kD to 125 kD, from 75 kD to 100 kD, or a range between any of the above integers.

Nucleic Acid Compositions for Expressing the Trispecific Antibodies

In another aspect, the present application provides nucleic acid compositions for expressing the trispecific antibodies described herein. DNA encoding an antigen binding site in a monoclonal antibody can be isolated and sequenced from the hybridoma cells using conventional procedures (e.g., by using oligonucleotide probes that are capable of binding specifically to genes encoding the heavy and light chains of the monoclonal antibodies). Alternatively, amino acid sequences from immunoglobulins of interest may be determined by direct protein sequencing, and suitable encoding nucleotide sequences can be designed according to a universal codon table. In other cases, nucleotide and amino acid sequences of antigen binding sites or other immunoglobulin sequences, including constant regions, hinge regions and the like may be obtained from published sources well known in the art.

Expression vectors encoding the trispecific antibody may be used to synthesize the trispecific antibodies in cultured cells in vitro or they may be directly administered to a patient to express the trispecific antibody in viva or ex vivo. As used herein, an "expression vector" refers to a viral or non-viral vector comprising a polynucleotide encoding one or more polypeptide chains corresponding to the trispecific antibody of the present disclosure in a form suitable for expression from the polynucleotide(s) in a host cell for antibody preparation purposes or for direct administration as a therapeutic agent.

A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice.

Nucleic acid sequences for expressing the trispecific antibody typically include an amino terminal signal peptide sequence, which is removed from the mature protein. Since the signal peptide sequences can affect the levels of expression, the polynucleotides may encode any one of a variety of different N-terminal signal peptide sequences. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of trispecific antibodies. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing high-level expression in a target cell of interest. The promoters may include constitutive promoters (e.g., HCMV, SV40, elongation factor-1α (EF-1α)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the antibody producing cell. Cell or tissue-specific transcriptional regulatory elements (TREs) can be incorporated into expression vectors to restrict expression to desired cell types. Pol III promoters (H1 or U6) are particularly useful for expressing shRNAs from which siRNAs are expressed. An expression vector may be designed to facilitate expression of the trispecific antibody in one or more cell types.

In certain embodiments, one or more expression vectors may be engineered to express both the trispecific antibody and one or more siRNA targeting the Tie2 pathway, the VEGF pathway or an immune checkpoint regulator.

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer.

To co-express the individual chains of the trispecific antibody, a suitable splice donor and splice acceptor sequences may be incorporated for expressing both products. Alternatively, an internal ribosome binding sequence (IRES) or a 2 A peptide sequence, may be employed for expressing multiple products from one promoter. An IRES provides a structure to which the ribosome can bind that does not need to be at the 5' end of the mRNA. It can therefore direct a ribosome to initiate translation at a second initiation codon within a mRNA, allowing more than one polypeptide to be produced from a single mRNA. A 2 A peptide contains short sequences mediating co-translational self-cleavage of the peptides upstream and downstream from the 2 A site, allowing production of two different proteins from a single transcript in equimolar amounts. CHYSEL is a non-limiting example of a 2 A peptide, which causes a translating eukaryotic ribosome to release the growing polypeptide chain that it is synthesizing without dissociating from the mRNA. The ribosome continues translating, thereby producing a second polypeptide.

An expression vector may comprise a viral vector or a non-viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In some embodiments, expression of the antibody chains is under the control of the regulatory element such as a tissue specific or ubiquitous promoter. In some embodiments, a ubiquitous promoter such as a CMV promoter, CMV-chicken beta-actin hybrid (CAG) promoter, a tissue specific or tumor-specific promoter to control the expression of a particular antibody heavy or light chain or single-chain derivative therefrom.

Non-viral expression vectors can be utilized for non-viral gene transfer, either by direct injection of naked DNA or by encapsulating the trispecific antibody-encoding polynucleotides in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

Methods for Producing the Trispecific Antibodies

Another aspect of the present application relates to a method for producing an trispecific antibody comprising culturing a cell transiently or stably expressing one or more constructs encoding one or more polypeptide chains in the trispecific antibody; and purifying the trispecific antibody from the cultured cells. Any cell capable of producing a functional trispecific antibody may be used. In preferred embodiments, the trispecific antibody-expressing cell is of eukaryotic or mammalian origin, preferably a human cell.

Cells from various tissue cell types may be used to express the trispecific antibodies. In other embodiments, the cell is a yeast cell, an insect cell or a bacterial cell. Preferably, the trispecific antibody-producing cell is stably transformed with a vector expressing the trispecific antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the trispecific antibody along with a selectable marker facilitating selection of stably transformed clones expressing the trispecific antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary trispecific antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In one embodiment, the cell line comprises a stably transformed *Leishmania* cell line, such as *Leishmania tarentolae*. *Leishmania* are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

In some embodiments, the cell lines expresses at least 1 mg, at least 2 mg, at least 5 mg, at least 10 mg, at least 20 mg, at least 50 mg, or at least 100 mg of the trispecific antibody/liter of culture.

Trispecific antibodies may be isolated from trispecific antibody expressing cells following culture and maintenance in any appropriate culture medium, such as RPMI, DMEM, and AIM V®. The trispecific antibodies can be purified using conventional protein purification methodologies (e.g., affinity purification, chromatography, etc.), including the use of Protein-A or Protein-G immunoaffinity purification. In some embodiments, trispecific antibodies are engineered for secretion into culture supernatants for isolation therefrom.

Methods of Treatment

Another aspect of the present application relates to a method for treating a cell proliferative disorder. The method comprises administering to a subject in need thereof an effective amount of a trispecific antibody according to the present disclosure. In another aspect, a method for treating a cell proliferative disorder comprises administering to a subject in need thereof an effective amount of one or more expression vectors expressing a trispecific antibody according to the present disclosure.

Any suitable route or mode of administration can be employed for providing the patient with a therapeutically or prophylactically effective dose of the trispecific antibody. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising a trispecific antibody in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

The trispecific antibody can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

Therapeutic trispecific antibody preparations can be lyophilized and stored as sterile powders, preferably under vacuum, and then reconstituted in bacteriostatic water (containing, for example, benzyl alcohol preservative) or in sterile water prior to injection. Pharmaceutical composition may be formulated for parenteral administration by injection e.g., by bolus injection or continuous infusion.

The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the trispecific antibody to elicit a desired response in the individual, previous therapy, the age, weight and sex of the patient, the patient's clinical history and response to the antibody, the type of the trispecific antibody used, discretion of the attending physician, etc. A therapeutically effective amount is also one in which any toxic or detrimental effects of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains in the trispecific antibody are derived from the same host in which they are to be administered in order to reduce inflammatory responses against the administered therapeutic agents.

The trispecific antibody is suitably administered to the patent at one time or over a series of treatments and may be administered to the patient at any time from diagnosis onwards. The trispecific antibody may be administered as the sole treatment or in conjunction with other drugs or therapies useful in treating the condition in question.

As a general proposition, a therapeutically effective amount or prophylactically effective amount of the trispecific antibody will be administered in a range from about 1 ng/kg body weight/day to about 100 mg/kg body weight/day whether by one or more administrations. In a particular embodiment, each trispecific antibody is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the trispecific antibody is administered at a dose of 500 µg to 20 g every three days, or 25 mg/kg body weight every three days.

In other embodiments, each trispecific antibody is administered in the range of about 10 ng to about 100 ng per individual administration, about 10 ng to about 1 µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The trispecific antibody may be administered daily, every 2, 3, 4, 5, 6 or 7 days, or every 1, 2, 3 or 4 weeks.

In other particular embodiments, the amount of the trispecific antibody may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

In certain embodiments, the coding sequences for a trispecific antibody are incorporated into a suitable expression vector (e.g., viral or non-viral vector) for expressing an effective amount of the trispecific antibody in patient with a cell proliferative disorder. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

EXAMPLES

Example 1. Production of Trispecific Antibodies

CHO-S cells were transfected with vectors carrying various trispecific molecules or reference molecules. Stable pools were generated and corresponding molecules were produced in Mix6 medium (50% CD-CHO medium and 50% EX-CELL CHO 5 medium plus 8 mM Glutamine, 0.1% HT) for 6 days at 34° C. Conditioned medium was harvested, processed and analyzed by 4-12% gradient SDS-PAGE using Gelcode Blue Safe protein Stain solution.

Example 2: Trispecific Antibodies Block PD-1/PD-L1 Interactions

Trispecific antibodies TS-M1 (FIG. 6A), TS-M2 (FIG. 6B), TS-M3 (FIG. 7A), TS-M4 (FIG. 7B), TS-M10 (FIG. 10B), and two different positive control antibodies (anti-PD-1 mAb (nivolumab) and anti-PD-1-TBN-P) were tested for their ability to block PD-1/PD-L1 interactions. Briefly, CHOK1 cells expressing human PD-1 were washed with FACS buffer (0.5% BSA, 2 mM EMTA in PBS) and re-suspended at a concentration of $10^6$ cells/ml with FITC-labeled human PD-L1 (Adipogen) at a final concentration of 5 µg/ml. 20 µl of the suspension was added to 96-well round bottom plate (Costar). 20 µl of each trispecific antibody (TS-M1, TS-M2, TS-M3, TS-M4, TS-M10, TS-M11), monospecific anti-PD-1 control and bispecific anti-PD-1-TBN-P control was added to a different well, along with various 2×-serial dilutions resulting in final antibody concentrations of 64 nM, 32 nM, 16 nM, 8 nM, 4 nM, 2 nM, 1 nM, 500 pM, 250 pM, 125 pM, 62.5 pM and 31.3 pM. The cells were incubated for 30 min on ice and then washed one time with 200 µl FACS buffer. Flow cytometry was performed and analyzed on an iQue IntelliCyt system (IntelliCyt Corporation). Half-maximal inhibitory concentrations ($IC_{50}$) were determined for each antibody based on the resulting mean fluorescence intensities measured.

The results of this analysis are depicted in FIGS. 12A-12G and FIG. 13. As shown in these figures, TS-M3 (FIG. 12C; IC50=1.8 nM) and TS-M4 (FIG. 12D; IC50=2.6 nM) were found to exhibit comparable IC50 concentration in blocking PD1/PDL1 interactions as compared to the parental PD-1 receptor mAb (FIG. 12F; IC50=1.5 nM). These results indicate that TS-M3 and TS-M4 substantially retain their ability to block PD1/PDL1 interactions in these trispecific antibodies as compared to the monospecific PD-1 antibody. Further, the bispecific antibody in which the Trebananib peptide (TBN-P) was fused to the carboxy-terminus of the parental PD-1 antibody was not found to impede anti-PD-1 blocking activity (FIG. 12G; IC50=1.5 nM). TS-M11 was found to exhibit a significant loss in blocking ability (FIG. 13; IC50=14 nM). TS-M1 (FIG. 12A; IC50=7 nM), TS-M2 (FIG. 12B; IC50=43 nM), and TS-M10 (FIG. 12E; IC50=12E) showed a significant increase in IC50 as compared to the parental PD-1 antibody.

Example 3: Binding Kinetics of Trispecific Antibody Binding to PD-1

Bio-Layer Interferometry (BLI) was performed using the Octet system (Pall ForteBio LLC) to characterize the binding kinetics of antibodies against His tagged human PD-1 (in house produced). 20 nM of each mAb (TS-M3, TS-M4 and parental anti-PD-1 mAb) was loaded onto the anti-human IgG capture biosensors. Association of analyte (PD-1-His) was achieved by placing the biosensors in wells containing 3 fold serial dilution of analyte (0.3 to 235 nM) for 5 mins. Dissociation of bound complexes was measured after transfer of the biosensors into kinetic buffer alone and monitoring of the interferometry signal for 10 minutes. The observed on and off rates ($K_a$ and $K_d$) were fit using a 1:1 binding global fit model comprising all concentrations tested, and the equilibrium binding constants ($K_D$) were calculated. The results of this analysis are shown in Table 2 below.

TABLE 2

| Binding affinity of antibodies to PD-1 | | | |
| --- | --- | --- | --- |
| Ab name | $K_D$ (nM) | $K_a$ (M$^{-1}$s$^{-1}$) | $K_d$ (s$^{-1}$) |
| anti-PD-1 mAb | 6.23 | 2.04E+05 | 1.27E−03 |
| TS-M3 | 3.26 | 2.11E+05 | 6.88E−04 |
| TS-M4 | 5.25 | 1.28E+05 | 6.72E−04 |

The results of this binding kinetics study confirm that trispecific antibodies TS-M3 and TS-M4 exhibit similar binding affinities to human PD-1 as the parental control antibody. These results are consistent with the notion that no loss of binding affinities for PD1 are present in these trispecific molecule configurations.

Example 4: Trispecific Antibodies Block Ang2/Tie2 Interactions

Trispecific antibodies were further tested for their ability to block Ang2/Tie2 interactions. Briefly, 96-well assay plates were coated with 1 µg/ml of recombinant human Ang2 (R&D) in PBS at 37° C. for 1 hour and then blocked with 3% BSA/PBS for 1 hour at room temperature. Serially diluted trispecific antibodies and recombinant human Tie2 were added to the wells and the plates were incubated overnight at room temperature. The antibodies tested in this assay included TS-M3 (FIG. 7A), TS-M4 (FIG. 7B), and Trebananib (as a positive control). The wells were washed with Wash Buffer (0.1% Tween-20 in PBS) and then incubated with anti-Tie2 antibody for 1 hour at room temperature. After washing with Wash Buffer, goat anti-mouse IgG-HRP was added to the wells and incubated for 1 hour at room temperature. Tie2 binding was detected by measuring light absorbance at 650 nm after addition of 3,3′,5,5′-tetramethylbenzidine TMB to the wells. Half-maximal inhibitory concentrations ($IC_{50}$) were determined for each antibody based on the resulting mean fluorescence intensities measured.

Figure 14A:
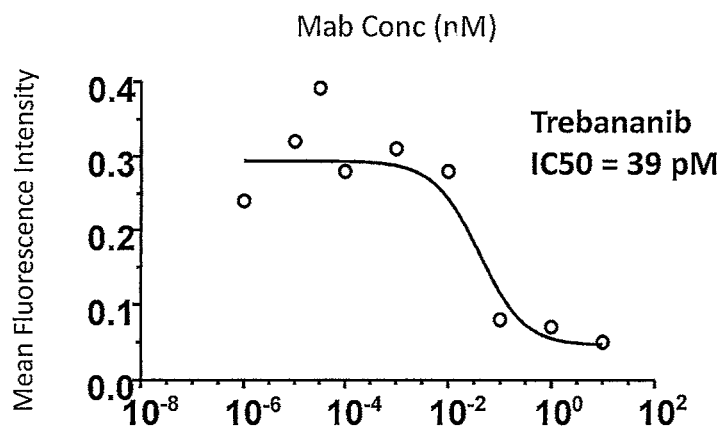
FIGS. 14A-14C depict the ability of trispecific antibodies to block Ang2/Tie2 interactions. The antibodies tested included a Trebananib positive control antibody (FIG. 14A), TS-M3 (FIG. 14B) and TS-M4 (FIG. 14C). Half-maximal inhibitory concentrations ($IC_{50}$) were determined for each antibody based on measurement of light absorbance at 650 nm following co-incubation of the human Tie2 with different concentrations of each antibody, followed by the sequential addition of anti-mouse IgG-HRP and 3,3',5,5'-tetramethylbenzidine (TMB) substrate.
Figure 14B:
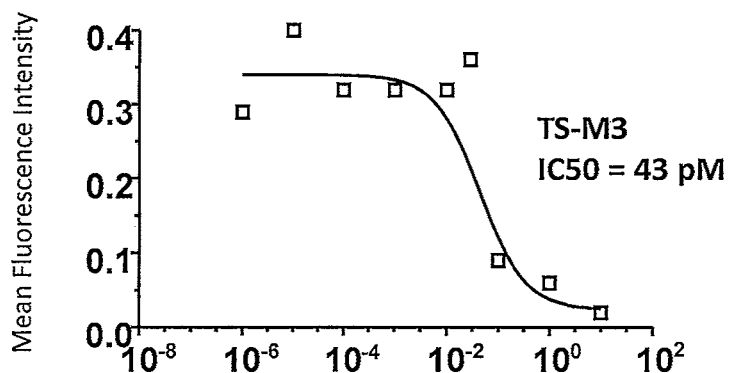
Figure 14C:
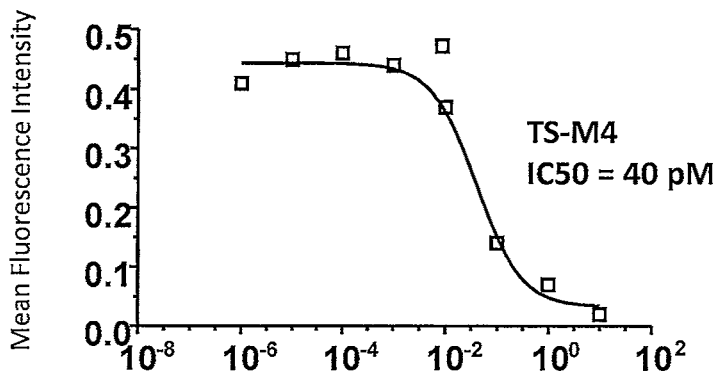

Analogous to the results concerning PD-1 blocking/binding, the IC50s calculated from these blocking assays for TS-M3 (FIG. 14B; IC50=43 pM) and TS-M4 (FIG. 14C; IC50=40 pM) were comparable to that of Trebananib (FIG. 14A, IC50=39 pM). Thus, TS-M3 and TS-M4 were similarly found to retain their Trebananib peptide blocking capabilities in their trispecific antibody configurations, indicating that fusing Trebananib peptides to the C-terminus of heavy chain constant regions does not negatively impact their activities.

Example 5: Binding Affinity Assays of Trispecific Antibody Binding to Ang2

96-well assay plates were coated with recombinant human angiopoietin 2 at 0.5 µg/ml in PBS for 1 hour at 37° C. and then washed once with Wash Buffer (0.1% Tween-20 in PBS) followed by blocking with 3% BSA in PBS overnight at 4° C. Serially diluted antibodies were then added to the wells and incubated for 1 hour at room temperature followed by washing with Wash Buffer. The antibodies tested included TS-M1 (FIG. 6A), TS-M2 (FIG. 6B), TS-M3 (FIG. 7A), TS-M4 (FIG. 7B), TS-M10 (FIG. 10B), Trebananib as a positive control and the anti-VEGF antibody, bevacizumab, as a negative control. In each case, a side by side comparison was conducted against the negative control, as indicated. Anti-human Fc antibody (goat-IgG) was added to wells and incubated for 1 hour at room temperature followed by washing with Wash Buffer. Anti-goat IgG-HRP antibody was then added to the wells and incubated for 1 hour at room temperature. TMB substrate was used to detect binding signal by measurement of light absorbance at 650 nM. Corresponding EC50 values were calculated as the concentration of antibody resulting in a half-maximal binding or absorbance.

The results of this analysis from two independent experiments are shown in FIGS. 15 and 16, respectively, where each curve corresponds to a different Ang2 binding activity tested. In each case, the negative control bevacizumab antibody did not show any appreciable binding as reflected in its lack of absorbance. Accordingly, only the EC50s corresponding to the Ang2 binding antibodies are displayed in the figures.

Figure 15A:
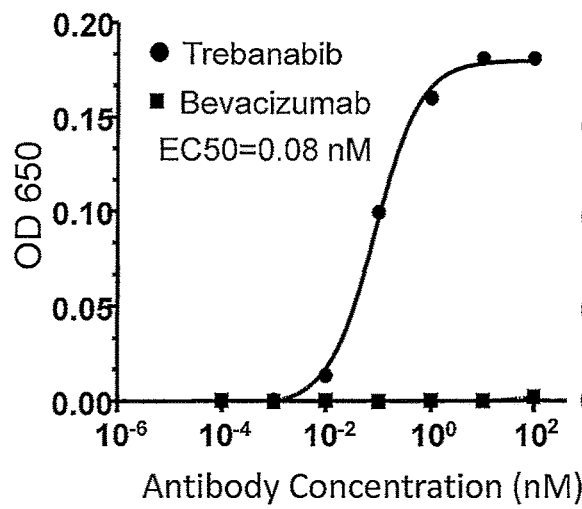
FIGS. 15A-15D depict the results of binding affinity assays of trispecific antibody binding to human angiopoietin 2 (Ang2). The antibodies tested included trebananib as a positive control (FIG. 15A), TS-M1 (FIG. 15B), TS-M3 (FIG. 15C), TS-M4 (FIG. 15D) and TS-M4 (FIG. 7B). Serial dilutions of the test antibodies were co-incubated with recombinant human Ang2, and then further incubated with anti-human Fc antibody (goat-IgG) and anti-goat IgG-HRP antibody. Corresponding EC50 values were calculated based on the concentration of antibody resulting in half-maximal binding as measured by the extent of light absorbance at 650 nM.
Figure 15B:
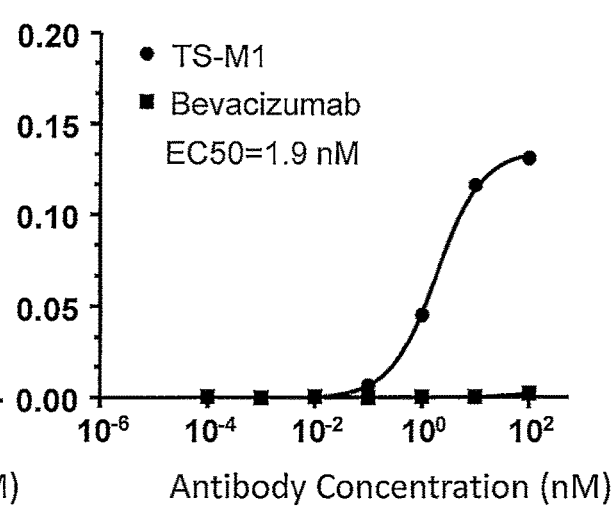
Figure 15C:
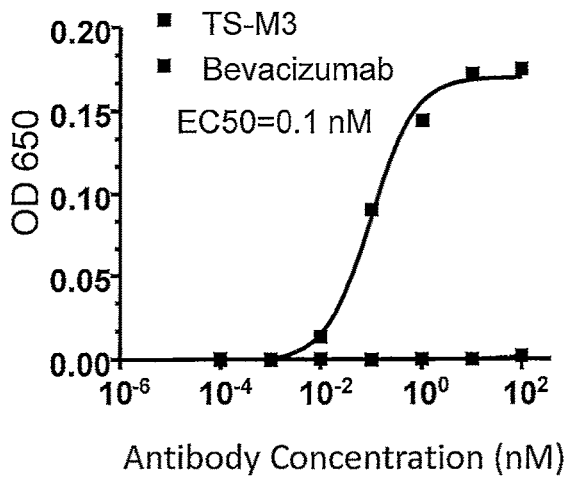
Figure 15D:
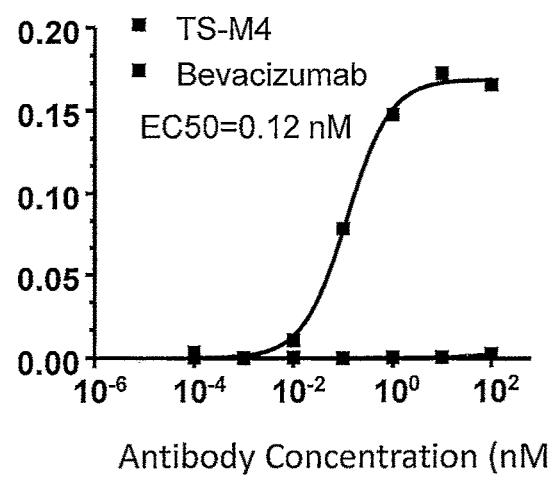
Figure 16A:
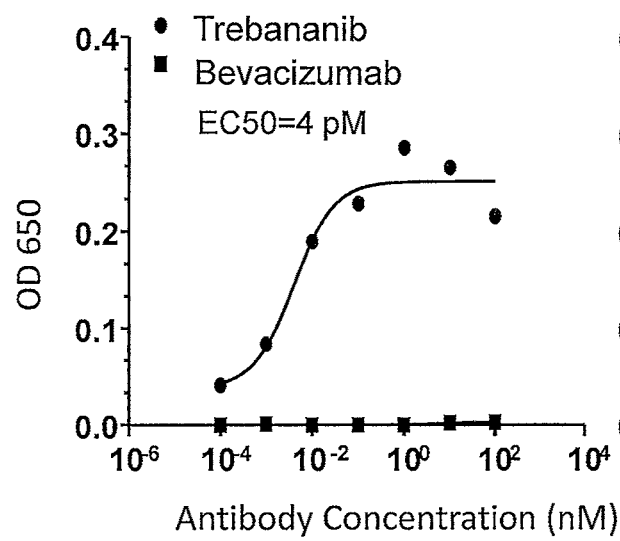
FIGS. 16A-16D depict the results of a second set of binding affinity assays between the trispecific antibodies and human angiopoietin 2 (Ang2) conducted as described in FIG. 15. The antibodies tested included trebananib as a positive control (FIG. 16A), TS-M1 (FIG. 16B), TS-M10 (FIG. 16C) and TS-M2 (FIG. 16D). Corresponding EC50 values were calculated based on the concentration of antibody resulting in half-maximal binding as measured by the extent of light absorbance at 650 nM.
Figure 16B:
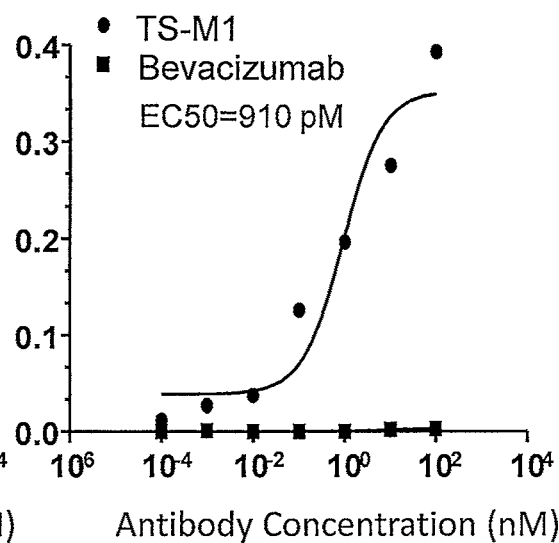
Figure 16C:
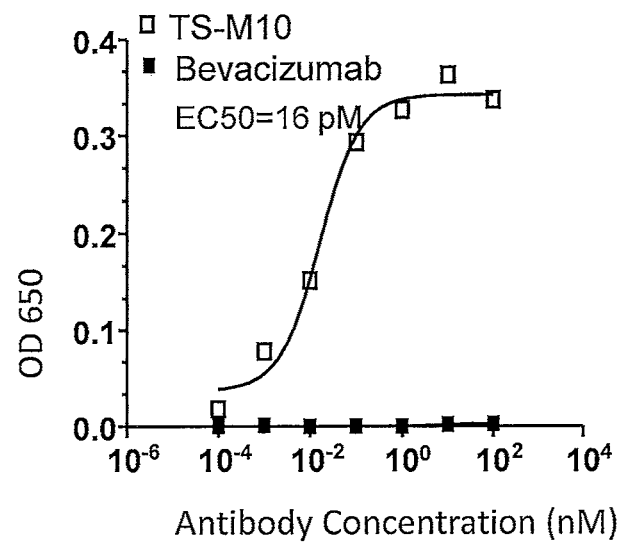
Figure 16D:
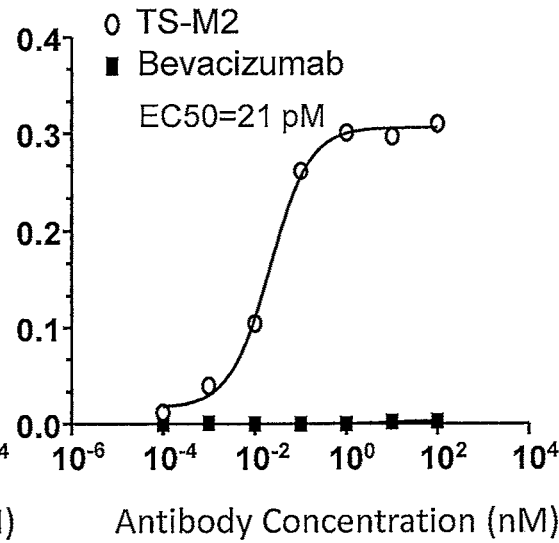

Consistent with the blocking data, TS-M3 (FIG. 15C; EC50=0.1 nM) and TS-M4 (FIG. 15D; EC50=0.12 nM) were found to exhibit comparable binding to Ang2 as Trebananib, the positive control (FIG. 15A, EC50=0.08 nM). In the second set of experiments, TS-M10 was found to exhibit a relatively similar Ang2 binding activity (FIG. 16C, EC50=16 pM) as Trebananib (FIG. 16A, EC50=4 pM). This suggests that the Trebananib peptide can be alternatively fused to the C-terminus of the antibody light chains as shown in FIG. 10B and still retain its function. In addition, despite the fact that the anti-PD1 scFv fusions at the C-termini of the heavy chains in TS-M10 (FIG. 10B) resulted in specific binding to PD-1 (FIG. 12E, IC50=14 nM), albeit less than the parental anti-PD1 mAb (FIG. 12F, IC50=1.5 nM), these results suggest that another anti-PD1 scFv may be substituted with the existing scFv in TS-M10 to improve upon the overall binding performance of this configuration. Likewise, given that TS-MS2 was found to exhibit a relatively similar Ang2 binding activity as Trebananib in this second set of experiments (FIG. 16D, EC50=21 pM), other anti-PD1 VRs may be used in place of the anti-PD-1 portion in the TS-M2 configuration to improve the overall performance of TS-M2, including its PD-1 binding activity.

Example 6: Trispecific Antibodies Block VEGF/VEGFR-2 Interactions 96-well assay plates were coated with 0.5 µg/ml of recombinant human VEGF 165 (R&D) in carbonate-bicarbonate buffer (pH 9.6) at 4° C. overnight followed by blocking with 3% BSA/PBS for 1 hour at room temperature. Serially diluted antibodies were then added to the wells in the plate and incubated for 30 minutes at room temperature. Recombinant human KDR (VEGF-R2) was added to the antibodies in the wells and incubated for 1 hour at room temperature. The wells were washed with Wash Buffer (0.1% Tween-20 in PBS) and then incubated with anti-VEGF R2 antibody for 1 hour at room temperature. Following a wash with Wash Buffer, goat anti-mouse IgG-HRP was added to the wells and incubated for 1 hour at room temperature. The amount of VEGF-R2 binding was detected by measuring light absorbance at 650 nm after addition of TMB to the plate.

Figure 17A:
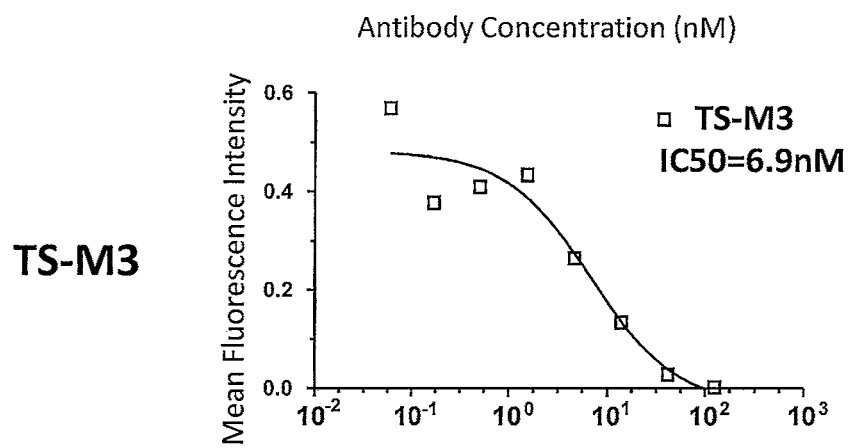
FIGS. 17A-17C depicts the ability of trispecific antibodies to block VEGF/VEGF-R2 interactions. The antibodies tested included TS-M3 (FIG. 17A), TS-M4 (FIG. 17B), and bevacizumab mAb as a positive control (FIG. 17C). Half-maximal inhibitory concentrations ($IC_{50}$) were determined for each antibody based on measurement of light absorbance at 650 nm following co-incubation of human KDR (VEGF-R2) with different concentrations of each antibody, followed sequentially by the addition of VEGF-R2 antibody, goat anti-mouse IgG-HRP and TMB substrate.
Figure 17B:
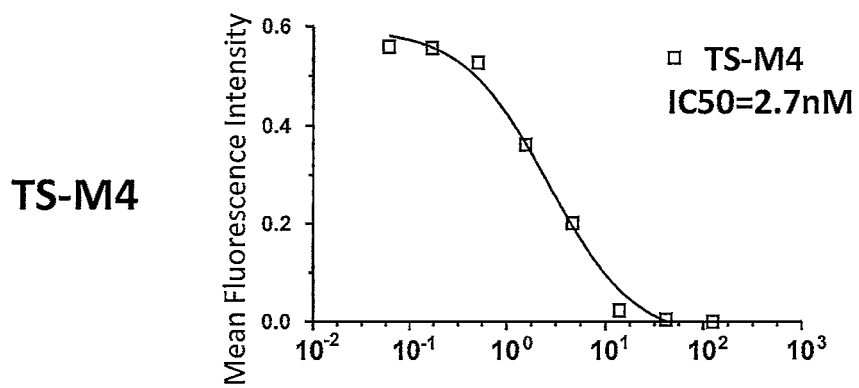
Figure 17C:
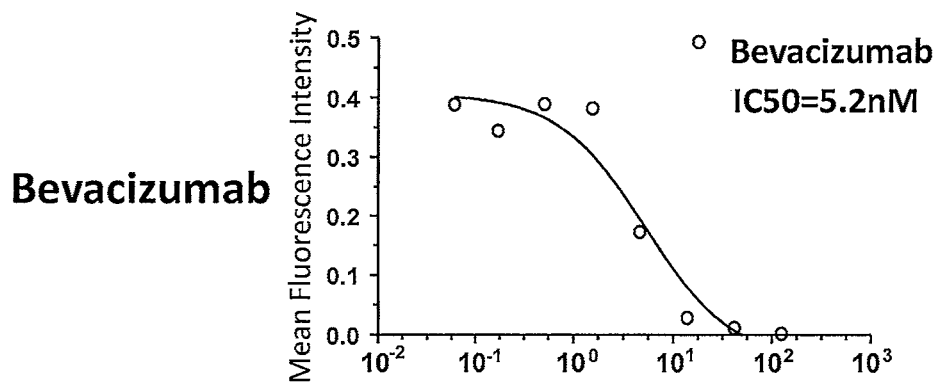

Analogous to the results concerning PD-1 and Ang2 blocking results, the IC50s calculated from these blocking assays for TS-M3 (FIG. 17A; IC50=6.9 nM) and TS-M4 (FIG. 17B; IC50=2.7 nM) were comparable to that of Trebananib, the positive control (FIG. 17C, IC50=5.2 mM). Thus, TS-M3 and TS-M4 were similarly found to retain their Trebananib peptide blocking capabilities in their trispecific antibody configurations, indicating that fusing Trebananib peptides to the C-terminus of heavy chain constant regions does not negatively impact their activities.

Example 7: Binding Affinity Assays of Trispecific Antibody Binding to VEGF 96-well assay plates were coated with recombinant human VEGF 165 (R&D) at 0.5 µg/ml in carbonate-bicarbonate buffer (pH 9.6) at 4° C. overnight and then washed once with Wash Buffer (0.1% Tween-20 in PBS) followed by blocking with 3% BSA in PBS for 1 hour at room temperature. Serially diluted antibodies were then added to the wells and incubated for 1 hour at room temperature followed by washing with Wash Buffer. The antibodies tested included TS-M1 (FIG. 6A), TS-M2 (FIG. 6B), TS-M3 (FIG. 7A), TS-M4 (FIG. 7B), TS-M10 (FIG. 10B), bevacizumab as a positive control and the bispecific antibody (anti-PD-1-TBN-P) as a negative control. In each case, a side by side comparison was conducted against the negative control, as indicated. Anti-human Fc antibody (goat-IgG) was then added to the wells and incubated for 1 hour at room temperature followed by washing with Wash Buffer. Anti-goat IgG-HRP antibody were then added to the wells and incubated for 1 hour at room temperature. TMB substrate was used to detect binding signals by measurement of light absorbance at 650 nM.

Figures 18E, 18F:
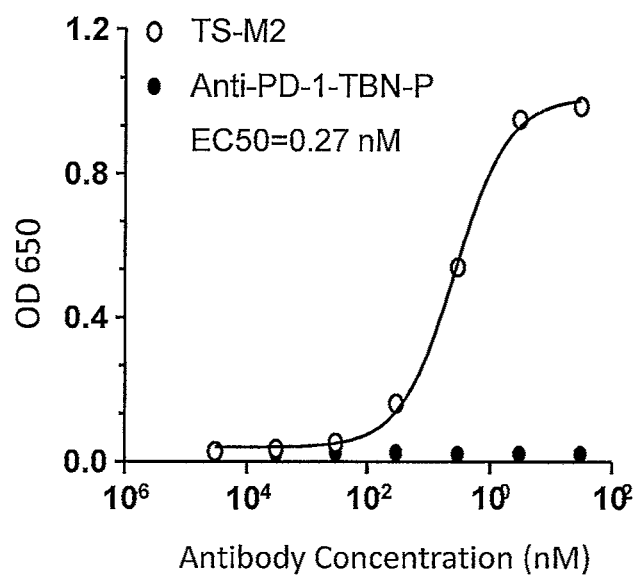

The results of this analysis are shown in FIG. 18, where each curve corresponds to a different VEGF binding activity tested. In each case, the negative control anti-PD-1-TBN-P antibody antibody did not show any appreciable binding as reflected in its lack of absorbance. Consistent with the blocking data in Example 6, TS-M3 (FIG. 18C; EC50=1.5 nM) and TS-M4 (FIG. 18D; EC50=0.34 nM) were found to exhibit comparable binding to VEGF as bevacizumab, the positive control (FIG. 18A, EC50=0.12 nM). In addition, the VEGF binding activities of TS-M2 (FIG. 18E, EC50=0.27 nM) and TS-M10 (FIG. 18F, EC50=0.34 nM) were also found to exhibit comparable binding to VEGF as bevacizumab, the positive control (FIG. 18A, EC50=0.12 nM). Thus, each of the trispecific antibody configurations in TS-M2, TS-M3, TS-M4 and TS-M10 retain binding to each of their 3 targets (PD-1, Ang2 and VEGF), albeit weaker binding to PD-1 by TS-M2 and TS-M10.

Example 8: Binding Kinetics of Trispecific Antibody Binding to VEGF

Bio-Layer Interferometry (BLI) was performed using the Octet system (Pall ForteBio LLC) to characterize the binding kinetics of antibodies against His tagged human PD-1 (in house produced) or VEGF 165 (R&D). 20 nM of each mAb (TS-M3, TS-M4 and parental anti-PD-1 mAb) was loaded onto the anti-human IgG capture biosensors. Association of analyte (PD-1-His) was achieved by placing the biosensors in wells containing 3 fold serial dilution of analyte (0.3 to 235 nM) for 5 mins. Dissociation of bound complexes was measured after transfer of the biosensors into kinetic buffer alone and monitoring of the interferometry signal for 10 minutes. The observed on and off rates ($K_a$ and $K_d$) were fit using a 1:1 binding global fit model comprising all concentrations tested, and the equilibrium binding constants ($K_D$) were calculated. The results of this analysis are shown in Table 2 below.

Figure 19A:
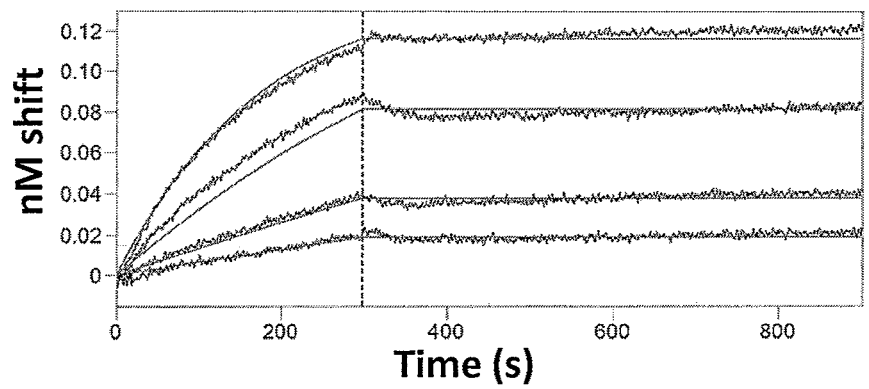
FIGS. 19A-19C depicts the results of a binding kinetics study of TS-M3 (FIG. 19A), TS-M4 (FIG. 19B) and bevacizumab positive control (FIG. 19C) binding to VEGF. Bio-layer interferometry on the Octet system (ForteBio) was used to characterize the binding kinetics of TS-M3 and TS-M4 to VEGF 165 using Bevacizumab as a reference. TS-M3, TS-M4 or Bevacizumab was captured onto the anti-human IgG biosensor. Association and dissociation of VEGF165 were followed for fifteen minutes to generate the sensorgrams depicted.
Figure 19B:
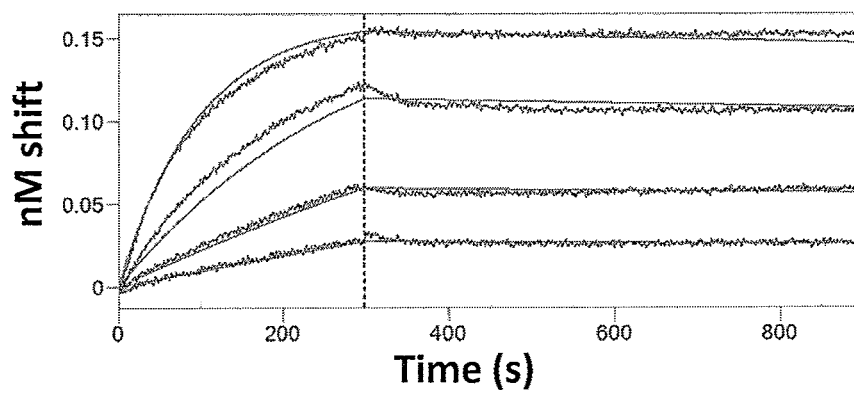

Bio-Layer Interferometry (BLI) was performed using the Octet system (Pall ForteBio LLC) to characterize the binding kinetics of antibodies against His tagged human VEGF 165 (R&D). 20 nM of each mAb (TS-M3, TS-M4 and bevacizumab) was loaded onto the anti-human IgG capture biosensors. Association of VEGF 165-His was achieved by placing the biosensors in wells containing 3 fold serial dilution of analyte (0.3 to 235 nM) for 5 mins. Dissociation of bound complexes was measured after transfer of the biosensors into kinetic buffer alone and monitoring of the interferometry signal for 10 minutes. The resulting sensorgrams show the interactions of TS-M3, TS-M4 or Bevacizumab with VEGF 165 (R&D Systems). The fits are indicated by the red lines whereas the sensorgrams are shown in blue for each concentration. Dotted lines demarcate the association and dissociation phases. In FIG. 19, the X axis depicts the time (in seconds) of the association (rapid on) and disassociation (very slow) phases, while the Y axis depicts the binding signal in nM on the sensor.

Figure 19C:
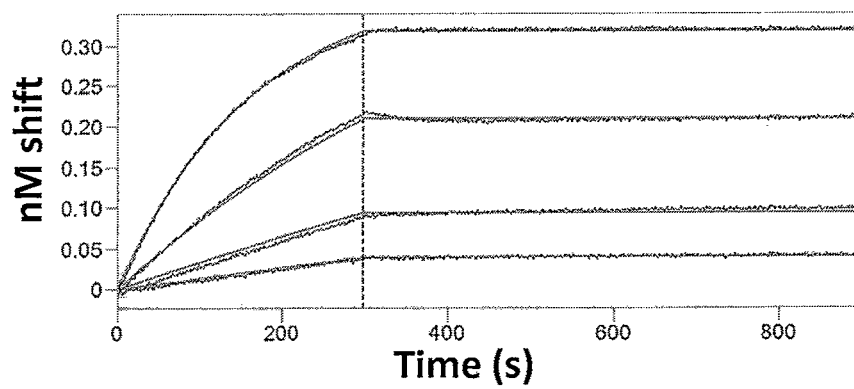

Consistent with the blocking data in Example 6 and the binding data in Example 7, TS-M3 (FIG. 19A) and TS-M4 (FIG. 19B) were found to exhibit similar sensorgrams of association and dissociation kinetics, suggesting comparable binding affinities to human VEGF as the positive control bevacizumab mAb (FIG. 19C).

Figure 20A:
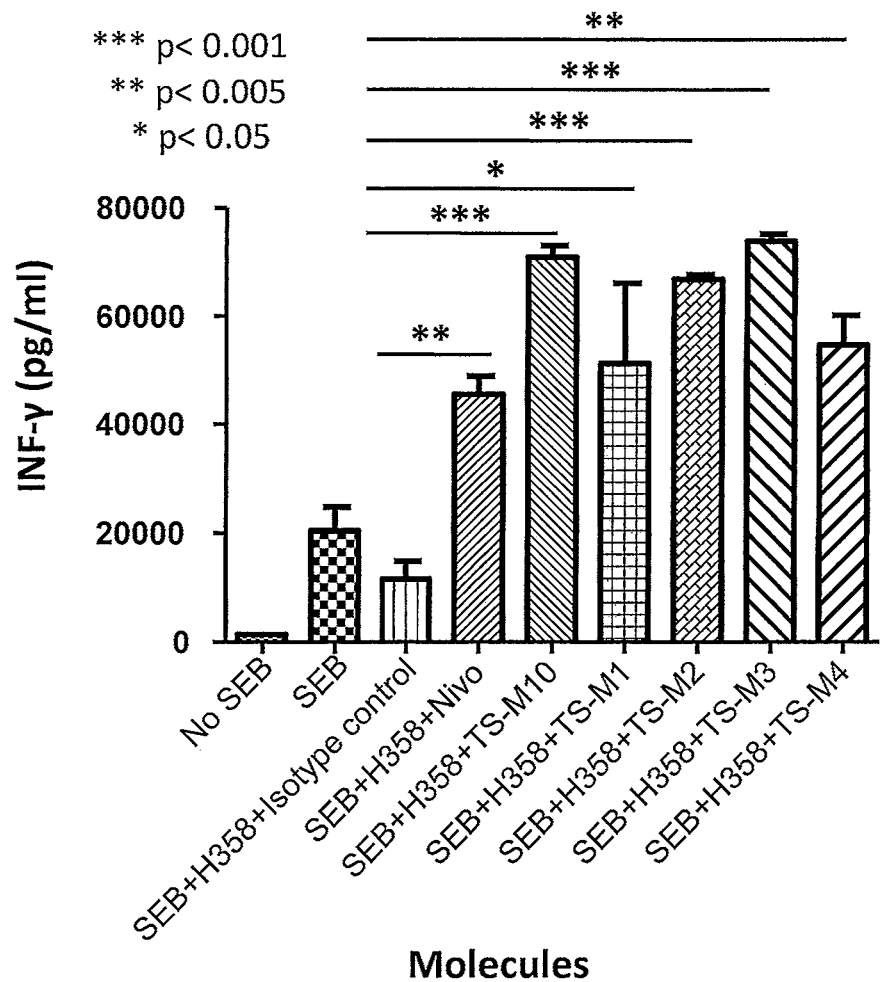
FIGS. 20A and 20B show the ability of trispecific antibodies to rescue PD-L1 mediated inhibition of human T cell function as function of IFN-γ production (FIG. 20A) or as a function of T cell proliferation index (FIG. 20B).
Figure 20B:
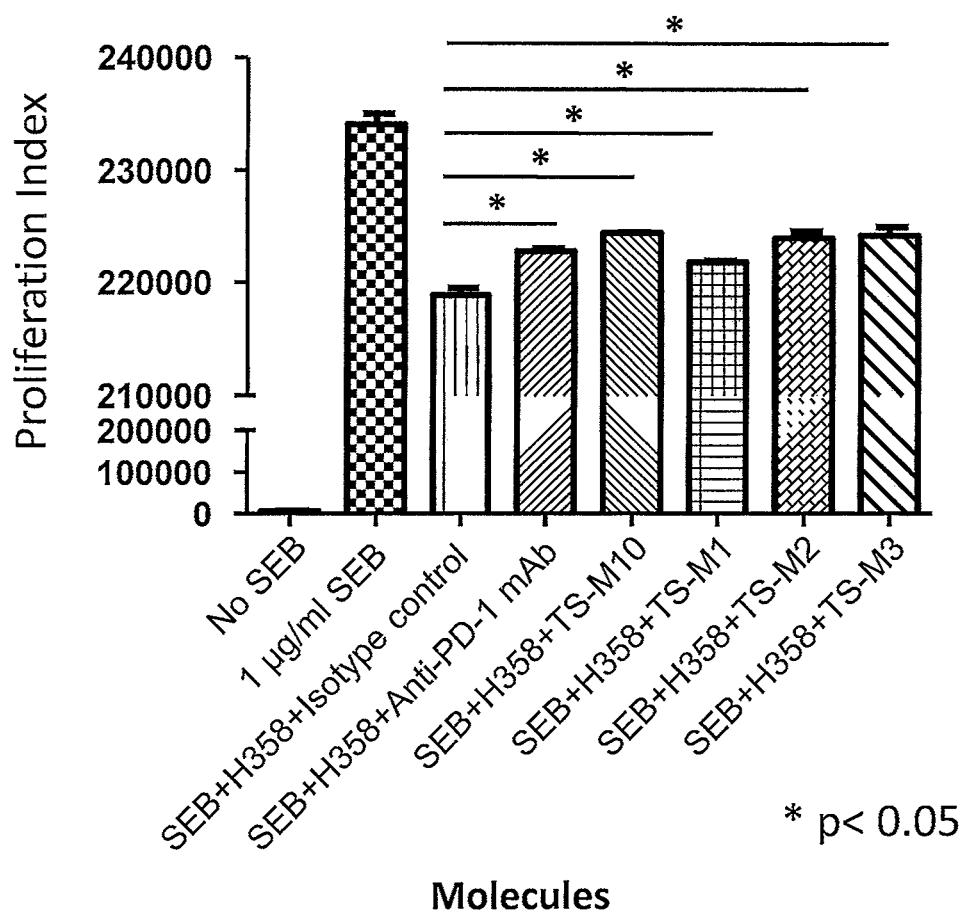

Example 9: Trispecific Antibodies Rescue PD-L1 Mediated Inhibition of Human T Cell Function Trispecific antibodies were tested for their ability to rescue PD-L1 mediated inhibition of human T cell function as function of IFN-7 production (FIG. 20A) or as a function of T cell proliferation index (FIG. 20B). In FIG. 20A, fresh PBMCs (Bioreclamation Inc.) were incubated with 2 µg/ml Staphylococcal Enterotoxin B (SEB, Toxin Technology Inc.) for 3 days. 30,000 of NCI-H358 human lung adenocarcinoma cells (ATCC) were added to provide an inhibitory PD-L1 signal. 64 nM of anti-PD-1 mAb (Nivolumab, "Nivo"), trispecific antibodies (TS10, TS1, TS2, TS3 and TS4) or isotype control Ab were added to block the inhibitory PD-L1 activities, hence activation of T cells. Supernatants were collected to measure the production of IFN-γ by ELISA. In FIG. 20B, fresh PBMC (Bioreclamation Inc.) were pre-activated by anti-CD3 (Bio-X-cell) and anti-CD28 (Biolegend) for 6 days. After resting, 100,000 of CellTrace Far Red (ThermoFisher) labeled PBMC were activated by 1 µg/ml SEB for 4 days. 20,000 NCI-H358 cells were added to provide an inhibitory PD-L1 signal. 64 nM of anti-PD-1 mAb (Nivolumab), trispecific antibodies (TS10, TS1, TS2 and TS3) or isotype control Ab were added to block the inhibitory PD-L1 signal. T cell proliferation index were calculated based on the reduction of mean fluorescence intensity reduction of CellTrace Far Red signal on gated CD3+ T cells.

The results of these analysis show that the trispecific antibodies rescue PD-L1 mediated inhibition of human T cell function as a function of IFN-γ production (FIG. 20A) and as a function of T cell proliferation index (FIG. 20B), suggesting that the trispecific antibodies share similar cell based functionality as the anti-PD-1 control antibodies.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A trispecific antibody, comprising:
   a first targeting domain that binds specifically to human PD 1;
   a second targeting domain that blocks binding of human VEGF-A to VEGFR-2; and
   a third targeting domain that binds specifically to human Tie2 tyrosine kinase receptor,
   wherein the trispecific antibody comprises a heavy chain/light chain combination selected from the group consisting of SEQ ID NOS:20 and 21, SEQ ID NOS:22 and 23, SEQ ID NOS:24 and 25, SEQ ID NOS:26 and 27, and SEQ ID NOS:38 and 39, and
   wherein the trispecific antibody exhibits a binding activity to human PD-1 within the same order of magnitude to that of nivolumab, a binding activity to VEGF within the same order of magnitude to that of bevacizumab and a binding activity to human Ang-2 within the same order of magnitude that of trebananib.

2. The trispecific antibody of claim 1, wherein the trispecific antibody comprises SEQ ID NO:24 and SEQ ID NO:25.

3. The trispecific antibody of claim 1, wherein the trispecific antibody comprises SEQ ID NO:26 and SEQ ID NO:27.

4. The trispecific antibody of claim 1, wherein the trispecific antibody comprises SEQ ID NO:38 and SEQ ID NO:39.

5. A method for treating a cell proliferative disorder, comprising:
   administering to a subject in need thereof the trispecific antibody of claim 1 in an amount effective to treat the proliferative disorder.

6. The trispecific antibody of claim 1, wherein the trispecific antibody comprises SEQ ID NO:20 and SEQ ID NO:21.

7. The trispecific antibody of claim 1, wherein the trispecific antibody comprises SEQ ID NO:22 and SEQ ID NO:23.

* * * * *